(12) United States Patent
Gajewski et al.

(10) Patent No.: US 6,716,422 B1
(45) Date of Patent: *Apr. 6, 2004

(54) VACCINE ADJUVANTS FOR IMMUNOTHERAPY OF MELANOMA

(75) Inventors: Thomas F. Gajewski, Chicago, IL (US); Francesca Fallarino, Peruga (IT)

(73) Assignees: ARCH Development Corporation, Chicago, IL (US); Genetics Institute Incorporated, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/168,832

(22) Filed: Oct. 8, 1998

Related U.S. Application Data

(63) Continuation-in-part of application No. 09/064,964, filed on Apr. 23, 1998, now Pat. No. 6,080,399.

(51) Int. Cl.⁷ .................. A61K 38/20; A61K 45/05; A61K 39/12; A61K 39/002; C07K 14/54

(52) U.S. Cl. ............ 424/85.2; 424/85.1; 424/93.7; 424/93.71; 424/184.1; 424/185.1; 424/204.1; 424/265.1; 424/277.1; 424/278.1; 514/2; 530/351; 530/300

(58) Field of Search ............ 424/85.2, 184.1, 424/278.1, 93.1, 93.7, 93.71, 85.1, 93.21, 204.1, 265.1, 277.1; 514/2; 530/351, 300

(56) References Cited

U.S. PATENT DOCUMENTS

| | | | |
|---|---|---|---|
| 4,554,101 A | 11/1985 | Hopp | 260/112.5 R |
| 5,571,515 A | 11/1996 | Scott et al. | 424/208.1 |
| 5,591,430 A | 1/1997 | Townsend et al. | 424/93.71 |
| 5,662,907 A | 9/1997 | Kubo et al. | 424/185.1 |
| 5,665,347 A | 9/1997 | Metzger et al. | 424/85.2 |
| 5,674,749 A * | 10/1997 | Chen et al. | 435/344.1 |
| 5,723,127 A | 3/1998 | Scott et al. | 424/184.1 |
| 5,744,132 A | 4/1998 | Warne et al. | 424/85.2 |
| 5,756,085 A | 5/1998 | Sykes et al. | 424/85.2 |
| 5,891,432 A * | 4/1999 | Hoo | 424/93.21 |

FOREIGN PATENT DOCUMENTS

| | | |
|---|---|---|
| WO | WO 95/29193 | 11/1995 |
| WO | WO 96/01557 | 1/1996 |
| WO | WO 96/29091 | 9/1996 |
| WO | WO 97/22349 | 6/1997 |

OTHER PUBLICATIONS

Shurin, M.R. et al. Antitumor activities of IL–12 and mechanisms of action. In: IL–12. Chemical Immunology, Adorini L. (ed): Basel, Karger, 68: 153–174, 1997.*

Wysocka, M. et al. Mechanism of the induction of anti-tumor immunity by B7.1 and interleukin–12. Annals of the New York Acadamey of Sciences, 795: 429–433, 1996.

Roitt, I.M. et al. Immunology, 3rd Edition. Mosty, St. Louis, pp. 2.15–2.16, 1993.

Fallarino et al., "Coadministration of IL–12 obviates the need to use dendritic cells in tumor antigen peptide–pulsed antigen–presenting cells (APC) vaccination," Abstract, *FASEB J.*, 12:A908, 1998.

Bhardwaj et al., "IL–12 conjunction with dendritic cells enhances antiviral CD8+ CTL responses in vitro," *J. Clin. Invest.*, 98(3):715–722, 1996.

Tuting et al., Autologous human monocyte–derived dendritic cells genetically modified to express melanoma antigens elicit primary cytotoxic T cell responses in vitro: enhancement by cotransfection of genes encoding the Th1–biasing cytokines IL–12 and IFN–α, *J. Immun.*, 160(3):1139–1147, 1998.

Bianchi et al., "IL–12 is both required and sufficient for initiating T cell reactivity to a class I–restricted tumor peptide (P815AB) following transfer of P815AB–pulsed dendritic cells," *J. Immunology*, 157:1589–1597, 1996.

Castelli et al., "Mass spectrometric identification of a naturally processed melanoma peptide recognized by CD8+ cytotoxic T lymphocytes," *J. Exp. Med.*, 181:363–368, 1995.

Chen et al., "Cross regulation by IL–10 and IL–2/IL–12 of the helper T cells and the cytolytic activity of lymphocytes from malignant effusions of lung cancer patients," *Chest*, 112:960–966, 1997.

Fallarino, Ashikari, Boon, Gajewski, "Antigen–specific regression of established tumors induced by active immunization with irradiated IL–12–but not B7–1–transfected tumor cells," *Inter. Immunol.*, 9(9):1259–1269, 1997.

Fallarino et al., "Endogenous IL–12 is necessary for rejection of P815 tumor variants in vivo," *J. Immunology*, 156:1095–1100, 1996.

Fleischhauer et al., Characterization of antigenic peptides presented by HLA–B44 molecules on tumor cells expressing the gene Mage–3, *Int. J. Cancer*, 68:622–628, 1996.

Gajewski, Renauld, Van Pel, Boon, "Costimulation with B7–1, IL–6, and IL–12 is sufficient for primary generation of murine anti–tumor cytolytic T lymphocytes in vitro," *J. Immunol.*, 154:5637–5648, 1995.

Gajewski, "B7–1 but not B7–2 efficiently costimulates CD8+ T lymphocytes in the P815 tumor system in vitro," *J. Immunol.*, 156: 465–472, 1996.

(List continued on next page.)

*Primary Examiner*—Anthony C. Caputa
*Assistant Examiner*—Anne L. Holleran
(74) *Attorney, Agent, or Firm*—Fulbright & Jaworski L.L.P.

(57) ABSTRACT

The invention provides methods of inducing the production of cytolytic T lymphocytes directed against malignancy or infectious agent by a mammal and treating such disease such that deleterious side effects are minimized and treatment of metastatic melanomas are surprisingly and dramatically improved.

43 Claims, 12 Drawing Sheets

OTHER PUBLICATIONS

Gajewski, Uyttenhove, Fallarino, Boon. "Tumor rejection requires a CTLA4 ligand provided by the host or expressed on the tumor: Superiority of B7–1 over B7–2 for active tumor immunization," *J. Immunol.* 156:2909–2917, 1996.

Grohmann et al., "Dendritic cells and interleukin 12 as adjuvants for tumor–specific vaccines," In: Dendritic cells in fundamental and clinical immunology, Ricciardi–Castagnoli (ed.), *Advances in Experimental Medicine and Biology*, 417:579–582, 1997.

Irvine et al., "Cytokine enhancement of DNA immunization leads to effective treatment of established pulmonary metastases," *J. Immunology*, 156:238–245, 1996.

Jäeger et al., "Generation of cytotoxic T–cell responses with synthetic melanoma–associated peptides in vivo: implications for tumor vaccines with melamona–associated antigens," *Int. J. Cancer*, 66:162–169, 1996.

Jäeger et al., "Granulocyte–macrophage–colony–stimulating factor enhances immune responses to melanoma–associated peptides in vivo," *Int. J. Cancer*, 67:54–62, 1996.

Kang et al., "Induction of melanoma reactive T cells by stimulator cells expressing melanoma epitope–major histocompatibility complex class I fusion proteins," *Cancer Res.*, 57:202–205, 1997.

Katayose et al., "MUC1–specific targeting immunotherapy with bispecific antibodies: inhibition of xenografted human bile duct carcinoma growth," *Cancer Res.*, 56:4205–4212, 1996.

Leonard et al., Effects of single–dose interleukin–12 exposure on interleukin–12 associated toxicity and interferon–γ production, *Blood*, 90(7):2541–2548, 1997.

Marchand et al., "Tumor regression responses in melamona patients treated with a peptide encoded by gene Mage–3," *Int. J. Cancer*, 63:883–885, 1995.

Reynolds et al., "A polyvalent melanoma vaccine induces a CD8 T cell response to Mart–1 and Mage–3 peptides," *87th Annual Meeting, Proceedings of the American Association for Cancer Research*, Washington, D.C., 37:3350, Abstract #3350, 1996.

Reynolds et al., "Stimulation of CD8+ T cell responses to Mage–3 and Melan–A/Mart–1 by immunization to a polyvalent melanoma vaccine," *Int. J. Cancer*, 72:972–976, 1997.

Ribas et al., "Genetic immunization for the melanoma antigen Mart–1/Melan–A using recombinant adenovirus–transduced murine dendritic cells," *Cancer Res.*, 57:2865–2869, 1997.

Romero et al., "Cytolytic T lymphocyte recognition of the immunodominant HLA–A*0201–restricted Malan–A/Mart–1 antigenic peptide in melanoma," *J. Immunology*, 159:2366–2374, 1997.

Tahara et al., "Fibroblasts genetically engineered to secrete interleukin 12 can suppress tumor growth and induce antitumor immunity to a murine melanoma in vivo," *Cancer Res.*, 54:182–189, 1994.

Tanaka et al., "Induction of antitumor cytotoxic T lymphocytes with a Mage–3 encoded synthetic peptide presented by human leukocytes antigen–A24," *Cancer Res.*, 57:4465–4468, 1997.

Valmori et al., "Analysis of Mage–3 specific cytolytic T lumphocytes in human leukocyte antigen–A2 melanoma patients," *Cancer Res.*, 57:735–741, 1997.

van der Bruggen et al., "A peptide encoded by human gene Mage–3 and presented by HLA–A2 induces cytolytic T lymphocytes that recognize tumor cells expressing Mage–3," *Eur. J. Immunol.*, 24:3038–3043, 1994.

Zajac et al., "Generation of tumoricidal cytotoxic T lymphocytes from healthy donors after in vitro stimulation with a replication–incompetent vaccina virus encoding Mart–1/Melan–A 27–35 epitope," *Int. J. Cancer*, 71:491–496, 1997.

Zitvogel et al., "IL–12–engineered dendritic cells serve as effective tumor vaccine adjuvants in vivo," *Interleikin 12: Cellular and MolecularImmunology of an Important Regulatory Cytokine*, Lotze et al.eds., Annals of the New York Academy of Sciences, 793:284–293, 1996.

Boon et al., "From defined human tumor antigens to effective immunization?," *Immunol. Today*, 16:334–336, 1995.

Brunda et al., "Antitumor and antimetastatic activity of interleukin 12 against murine tumors," *J. Exp. Med.*, 178:1223–1230, 1993.

Chen et al., "Tumor immunogenicity determines the effect of B7 costimulation on T cell–mediated tumor immunity," *J. Exp. Med.*, 179:523–532, 1994.

Fitch et al., "Differential regulation of murine T IVmphocyte subsets," *Annul. Rev. Immunol.*, 11:29–48, 1993.

Mukherji et al., "Induction of antigen–specific cytolytic T cells in situ in human melanoma by immunization with synthetic peptide–pulsed autologous antigen presenting cells," *Proc. Natl. Acad. Sci. USA*, 92:8078–8082, 1995.

Steinman et al., Identification of a novel cell type in peripheral lymphoid organs of mice. V. Purification of splenic dendritic cells, new surface markers, and maintenance in vitro., *J. Exp. Med.* 149:1–16, 1979.

Townsend and Allison, "Tumor rejection after direct costimulation of CD8+ T cells by B7–transfected melanoma cells," *Science*, 259:368–370, 1993.

Uyttenhove et al., "The expression of mouse gene P1A in testis does not prevent safe induction of cytolytic T cells against a P1A–encoded tumor antigen." *Int. J. Cancer.* 70:349–356, 1997.

Uyttenhove et al., "Immunogenic variants obtained by mutagenesis of mouse mastocytoma P815. I. Rejection by syngeneic mice," *J. Exp. Med.*, 152:1175–1183, 1990.

Fallarino et al., "Improved Efficacy of Dendritic cell vaccines and successful immunization with tumor antigen peptide–pulsed peripheral blood mononuclear cells by coadministration of recombinant murine interleukin–12". *Int. J. Cancer*, 80:324–333, 1999.

* cited by examiner

VACCINE ADJUVANTS FOR IMMUNOTHERAPY OF MELANOMA

The present application is a continuation-in-part of U.S. patent application Ser. No. 09/064,964 filed Apr. 23, 1998 now U.S. Pat. No. 6,080,399.

The government owns rights in the present invention pursuant to GCRC-CAP Award number 3M01RR00055-3651 from National Institutes of Health.

BACKGROUND OF THE INVENTION

1. Field of the Invention

The present invention relates generally to the fields of immunotherapy, oncology and infectious disease control. More particularly, it concerns novel methods of treating infectious diseases and cancers, in particular melanomas, with a combinatorial adjuvant or adjuvants in such a manner that an unexpectedly strong immune response directed against the diseases or melanomas is induced without the deleterious side effects that have been previously observed with standard chemotherapy.

2. Description of Related Art

Melanoma is a cancer of the pigmented cell of the skin, the melanocyte. Patients with metastatic (Stage IV) malignant melanoma have a median survival of approximately one year (Balch et al., 1993; Koh, 1991). Current standard treatment consists of combination chemotherapy with agents such as cisplatin, DTIC, and BCNU, with or without cytokines such as interleukin-2 (IL-2) or interferon-α (IFN-α) (Balch et al., 1993; Koh, 1991; Legha and Buzaid, 1993). Response rates to chemotherapy have been reported to be as high as 60%, yet only approximately 5% of patients experience long term survival, regardless of the therapeutic regimen employed. Clearly, new approaches to the treatment of metastatic melanoma are needed.

Conventional chemotherapy aims to control the growth of cancer by targeting rapidly growing cells. However, this function is not specific, as many normal cells, such as those of the bone marrow and the intestinal epithelium, also have a basal level of proliferation. Therefore, many normal cells of the body also are susceptible to the toxic effects of chemotherapy, and conventional chemotherapy can impart a substantial degree of morbidity to the patient.

The attractiveness of immunotherapy is its specificity. If antigens were expressed on the tumor cells that were not expressed by normal cells of the host, then specific cytolytic T lymphocytes (CTL) could theoretically be activated to selectively kill the tumor cells while sparing the normal tissues of the patient. To this end, considerable effort has been made in the last decade to identify such tumor-specific antigens which may serve as targets for specific tumor cell killing (Boon et al., 1994; Boon et al., 1995).

Initial approaches to the immunotherapy of cancer have met with limited success. Vaccinations with irradiated tumor cells, with or without adjuvants, have generated response rates of 10–20% (Berd et al., 1990). Non-specific immune potentiators such as Bacillus Calmette-Guerin (BCG) also have given low but detectable response rates (Eilber et al., 1976). Treatment of patients with metastatic renal cell carcinoma with the T cell growth factor IL-2 has resulted in response rates of 15–20%, with several percent of patients experiencing a significant long-term survival (Hawkins, 1996). Similarly, the addition of IL-2 to standard chemotherapy for metastatic melanoma may result in increased response rates (Eilber et al., 1976). Collectively, these observations support the concept that immune manipulation has the potential to benefit patients with certain types of cancer, but clearly indicate that the current approaches are suboptimal. One hypothesis to explain the low overall response rates to these therapies is that the approaches up to now have aimed to amplify an immune response that has already been initiated by the host. In fact, the fundamental problem may be that most patients do not appropriately initiate an anti-tumor immune response at all. Further, tumor antigen-specific immunization will require induction of cytolytic T cell activity, and little is known regarding the optimal method of achieving this goal.

The molecular characterization of antigens specifically expressed on tumor cells but not on most normal cells of host origin has opened the possibility of tumor-specific vaccination in the immunotherapy of cancer. The last several years have witnessed a rapid expansion in the identification of human tumor antigens and their genes, chiefly in melanoma cell lines, that comprise several distinct categories: 1) point mutations in normal cellular genes; 2) differentiation antigens restricted to the melanocyte lineage; 3) intron sequences that become included in the coding region of a gene; 4) viral gene products; 5) underglycosylated normal gene products; and 6) developmentally regulated, non-mutated genes that. are not normally expressed in most adult tissues (Chen et al., 1993). Immune recognition of these antigens occurs via specific $CD8^+$ CTL that interact with antigenic peptides bound to a groove in class I MHC (HLA) molecules. Class II MHC-binding epitopes recognized by $CD4^-$ T cells also have been described.

Under optimal circumstances, initiation of an immune response is triggered by peptide/MHC complexes expressed by host antigen-presenting cells (APC), and additionally requires multiple cofactors provided by APC. Several cell types appear to be capable of serving as "professional" APC, including dendritic cells (DC), activated B cells, and activated macrophages. After initial activation, CTL induced by APC interactions are thought to migrate throughout the host, recognize the same MHC/peptide complex on the tumor cells, and are triggered to kill them. This antigen-specific cytolysis is mediated largely via induction of apoptosis. It is hypothesized that one or several steps along this pathway of T cell activation and target cell recognition may be defective in tumor-bearing individuals.

MAGE-1 was the first human tumor antigen gene to be cloned and characterized (Van der Bruggen et al., 1991). It is expressed by several melanoma cell lines but not by any adult tissues except the testis. Therefore, it falls into category 6 listed above, being a normal gene that is abnormally expressed. MAGE-1 belongs to a family of at least 12 related genes, many of which also are expressed in various tumor cell types (De Plaen et al., 1994). One of these, MAGE-3, has been found to be expressed in approximately two-thirds of all melanoma samples tested. Peptides derived from the MAGE-3 protein have been identified that bind to the grooves of HLA-A1, HLA-A2, and HLA-B44 MHC molecules (Van der Bruggen et al., 1991; Van Pel et al., 1995; Van der Bruggen et al., 1994), and CTL recognizing each of these peptide/HLA combinations also have been observed. HLA-A2 is the most frequently expressed HLA allele in humans, present in about 50% of individuals.

Recently, 12 patients with MAGE-3$^+$ metastatic melanoma were injected in Europe at monthly intervals with the MAGE-3 peptide that binds to HLA-A1 (Marchand et al., 1995). Either 100 or 300 μg of peptide was injected in phosphate-buffered saline (PBS) at 2 subcutaneous sites distant from any tumor location. There were no major toxicities, and 3 patients experienced mild discomfort from inflammation at tumor locations or lymph nodes. Six patients were well enough to complete 3 monthly injections. Rather surprisingly, 3 of those 6 demonstrated major partial responses, giving an overall response rate of 25%.

Since the identification of the MAGE family, several additional melanoma antigens have been characterized including Melan-A, gp100 and tyrosinase (Old et al., 1996). One of these, Melan-A, is expressed by nearly all melanoma cell lines tested (Coulie et al., 1994), as well as in normal melanocytes. It therefore falls into category 2 above, encoding a melanocyte differentiation antigen. A peptide encoded by Melan-A has been defined that binds to HLA-A2.

Eighteen HLA-A2$^+$ patients with metastatic melanoma were immunized with a peptide derived from Melan-A emulsified in incomplete Freund's adjuvant (Cormier et al., 1997). No major toxicities were observed, and evidence of immunization was demonstrated in 12 patients. However, no tumor regression responses were seen, indicating that this rather straightforward vaccination strategy was not sufficient to generate a therapeutic effect. Collectively, these results support the general safety of tumor antigen peptides in humans, especially compared to the toxicities of conventional chemotherapy.

Recent advances in the understanding of T lymphocyte activation and differentiation have indicated several key costimulatory factors provided by APC that are vital for the optimal generation of CD8$^+$ CTL. In fact, stimulation of T cells via the T cell receptor for antigen (TCR) in the absence of additional costimulatory factors has been shown to induce not activation, but rather an unresponsive state termed clonal anergy (Schwartz, 1990; Tan et al., 1993). Thus, participation of costimulator molecules is an essential component to initiating productive T cell differentiation. The specific cofactors present during and immediately after initial T-cell encounter with antigen determine the functional phenotype of the cells that emerge. For CD8$^+$ T cells, the principal functional phenotypes fall into two subsets designated Tc1 and Tc2 (Sad et al, 1995). Tc1 cells produce high levels of IFN-$\gamma$ and TNF and have high lytic activity, whereas Tc2 cells produce IL4 and IL-5 and are poorly lytic (Cronin et al., 1995). It has been suggested that a Tc1-type response might be superior at mediating tumor rejection.

The B7-family of costimulator molecules, comprised of B7-1 and B7-2, appears to be important for instructing developing T cells to produce IL-2, and for preventing induction of T cell unresponsiveness or anergy (Linsley et al., 1991; Harding et al., 1992; Gimmi et al., 1993). B7-1/B7-2 interact with two counter-receptors, designated CD28 and CTLA4, on the surface of T lymphocytes. Provision of B7 during the activation of naive T cells is the trigger that gets the initial response going. At that point, the particular exogenous cytokines present determine the functional phenotype of the resulting activated effector cells. IL-12 appears to induce a high IFN-$\gamma$-producing Tc1 phenotype, whereas IL4 favors development of Tc2 cells (Sad et al., 1995). These characteristics parallel those of CD4$^+$ helper T lymphocytes (Fitch et al., 1993). Provision of both B7 and IL-12 allows generation of potent tumor antigen-specific CTL in vitro (Gajewski et al, 1995). In several murine models in vivo, transfection of immunogenic tumors to express B7 has resulted in CD8$^+$ T cell-dependent rejection by syngeneic mice (Townsend and Allison, 1993, Chen et al., 1994). IL-12 also can facilitate the regression of murine tumors in a T cell-dependent fashion (Brunda et al., 1993). Blockade of host B7 or IL-12 in vivo prevents the rejection of otherwise very immunogenic tumors (Gajewski et al., 1996; Fallarino et al., 1996), indicating that these two factors are normally employed by the immune response mediating tumor rejection.

SUMMARY OF THE INVENTION

The present invention provides methods of overcoming shortcomings of the prior art by providing improved methods of treating diseases and infections that are unexpectedly effective in inducing immune responses directed against diseases and infections. In some preferred embodiments the invention relates to treating melanomas, such as metatstatic melanomas, and viral infections. The inventors have discovered that administration of the adjuvants in the described manner are far more effective than would have been predicted based on the prior art or when the adjuvants are administered either alone or in a different combination or order. The invention provides the further advantage of reducing deleterious side effects that have been previously associated with cancer therapies.

As used in this specification and the appended claims and in accordance with long-standing patent law practice, the singular forms "a" "an" and "the" generally mean "at least one", "one or more", and other plural references unless the context clearly dictates otherwise. Thus, for example, references to "a cell", "a peptide" and "an adjuvant" include mixtures of cells, one or more peptides and a plurality of adjuvants of the type described; and reference to "IL-12" includes different species of such IL-12, for example, recombinant human IL-12, and so forth.

As used herein, the term "a recombinant peptide", unless otherwise expressly stated, is used to succinctly refer to a recombinant peptide which is derived from an antigen that can be recognized by T-lymphocytes. "Recombinant peptides" are generally peptide molecules that may be provided to cells (or animals) by the hand of man. The term "recombinant" peptide does not generally extend to amino acid sequence, peptides and proteins that may have been moved by a process of nature such that they have "recombined" in a sequence or order different to the parent cell or organism from which they were derived without intervention by man.

The invention provides a method of inducing a mammalian immune response comprising: providing a composition comprising IL-12 and antigen-presenting cells pulsed with peptide and administering the composition to a mammal in an amount effective to induce an immune response. In one illustrative system the composition, or adjuvant, comprises peptide-pulsed, or loaded, antigen-presenting cells (APCs) and IL-12.

The invention further provides that the APCs comprise autologous cells and in some illustrative embodiments the antigen-presenting cells may comprise B cells activated by lipopolysaccharide, whole spleen cells, dendritic cells, fibroblasts or non-fractionated peripheral blood mononuclear cells (PMBC). Of course, it is understood that one of skill in the art will recognize that other antigen-presenting cells may be useful in the invention and that the invention is not limited to the exemplary cell types which are described herein.

The APCs are pulsed, or loaded, with antigenic peptide or recombinant peptide derived from at least one antigen. In one embodiment the peptide comprises an antigenic fragment capable of inducing an immune response that is characterized by the production of cytolytic T lymphocytes (cytolytic T cells or CTLs) which are directed against a malignancy or infection by a mammal. In a particular exemplary embodiment the peptide comprises one or more fragments of an antigen binding to class I MHC or class II MHC molecules (see Tables 1 and 2 for lists of exemplary tumor antigens). It is understood that the antigens listed in Tables 1 and 2 are provided for illustrative purposes and the skilled artisan will recognize that the described invention is not limited to these illustrative antigens.

In an illustrative system, the peptides comprise one or more fragments of one or more antigens expressed by melanoma tumors or other cancers, or infectious agents such as viruses, bacteria, parasites and the like. In some illustrative embodiments of the invention the peptide comprises MAGE-1, MAGE-3, Melan-A, P198, PIA, gp100 or tyrosinase. Of course, it is understood that one of skill in the art will recognize that peptides comprising one or more fragments of other antigens may be useful in the invention and that the invention is not limited to the exemplary peptides and antigens which are described herein.

APCs may be pulsed with any effective concentration of peptide. In a particular illustrative system, the APCs comprise cells pulsed with about 0.1 $\mu$M–1 $\mu$mM peptide. In a preferred illustrative system, the APCs comprise cells pulsed with about 1 $\mu$M–100 $\mu$M peptide, with a further preferred embodiment with about 10 $\mu$M–50 $\mu$M.

In a further embodiment the malignancy comprises a melanoma or other cancer, such as cancer of the prostate, ovary, kidney, lung, brain, breast, colon, bone, skin, testes or uterus, and the virus comprises a retrovirus, adenovirus, vaccinia virus, herpesvirus, adeno-associated virus, lentivirus, human immunodeficiency virus (HIV), or an arbovirus (arthropod-borne virus) (comprehensive lists and descriptions of arboviruses are provided in *Entomology in Human and Animal Health*, 7th ed., 1979 and *The Biology of Disease Vectors*, University Press Colorado, 1996, both of which are incorporated herein by reference). In another embodiment the infection comprises a bacterial or parasitic infection.

Mammals include, but are not limited to, equines, cattle, felines, canines, rats, mice and humans.

In a particular embodiment, the invention provides a method of inducing a mammalian immune response, wherein the peptide-pulsed APCs are administered to a mammal in need thereof, in a single therapeutic dose in combination with a single therapeutic dose of IL-12 followed by multiple therapeutic doses of IL-12.

Dosages may be any that induce an immune response. In certain embodiments, the amount of APCs administered comprises $1\times10^6$–$1\times10^9$ per dose. In exemplary preferred embodiments the amount of APCs administered comprises about $1\times10^8$ per dose. In other embodiments the amount of IL-12 administered comprises 1 ng/kg–1000 ng/kg. In certain preferred exemplary embodiments the amount of IL-12 administered comprises 30–50 ng/kg per dose. Of course, it will be understood by the skilled artisan that the preferred dosage should be individualized to the patient following good laboratory practices and standard medical practices.

In another aspect the invention provides a method of treating a patient with a malignancy or infection comprising administering an adjuvant or composition comprising peptide-pulsed antigen-presenting cells and IL-12.

In a particular embodiment, the invention provides a composition using tumor antigen peptide pulsed autologous PBMC with and without rhIL-12 to produce an immune response in humans. In preferred embodiments, the tumor antigen peptide is Mage3 or MelanA. In further preferred embodiments, rhIL-12 is provided in addition to the Mage3 or MelanA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
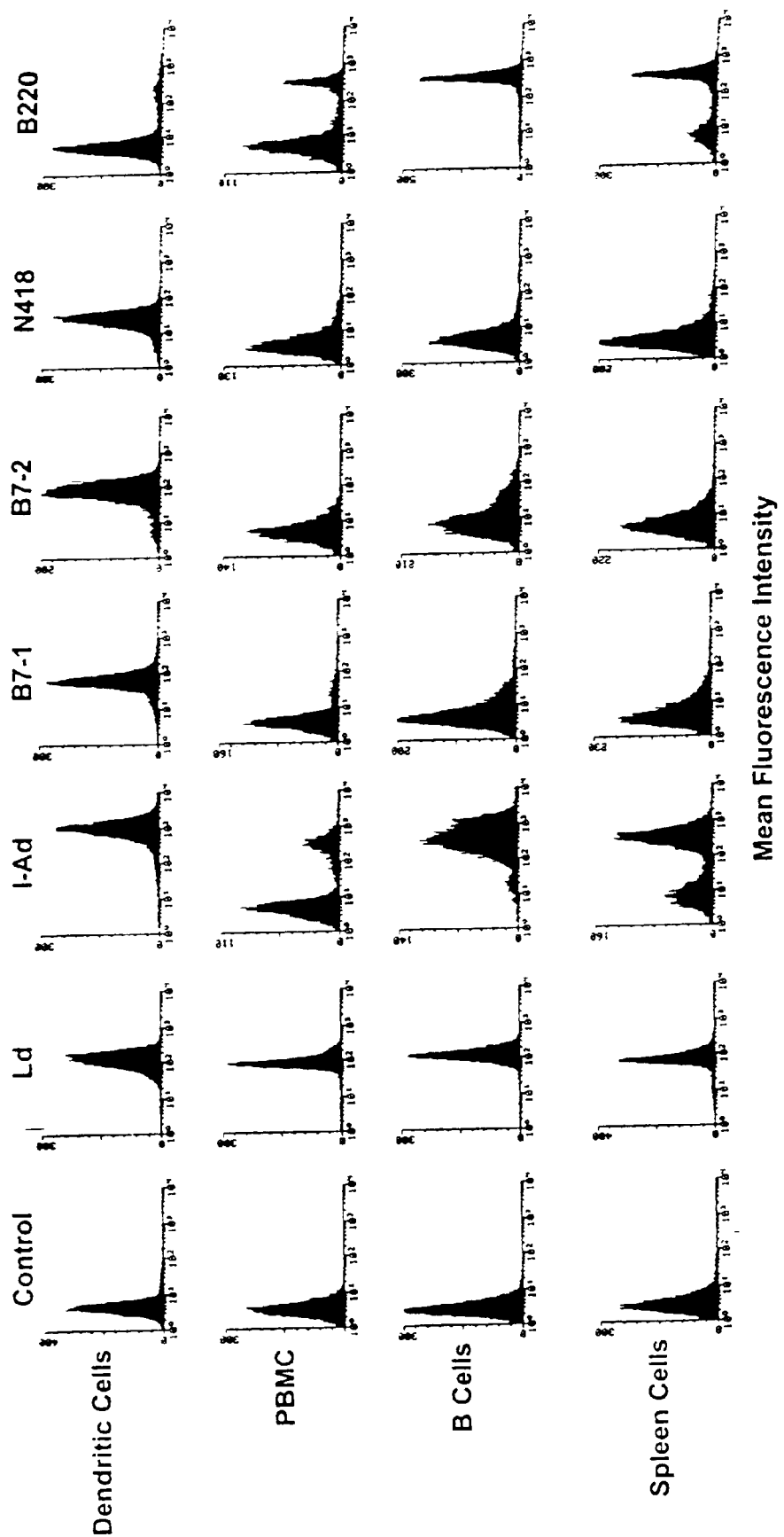
FIG. 1. Expression of surface markers by the various APCs used in this study. Splenic DC (sDC), unfractionated PBMC, purified B cells, and unfractionated splenocytes were prepared from naive DBA/2 mice as described in Example 1. The cells were then stained with the indicated FITC-conjugated mAbs and analyzed by flow cytometry. The data are representative of at least two separate replicates.

The invention discloses novel methods of using a vaccine adjuvant which specifically induces antigen-specific immune stimulation against an antigen derived from a tumor or infectious agent. Mammalian blood cells that are pulsed by this innovative method have been demonstrated to induce specific cytolytic T lymphocyte (CTL) production and protect from tumorgensis. In general, the method admixes the tumor or disease antigen with autologous peripherial blood cells which are then irradiated and injected back into the animal or patient. The injection is co-administered with IL-12 which helps to stimulate the immune system to promote an anti-neoplastic or anti-disease response in the animal or patient. In exemplary systems, this method has been applied to mice using the mastocytoma tumor antigens P198 and P1A, and to humans using the melanoma antigens MAGE-3 and Melan-A. The use of autologous peripherial blood cells, which can be readily harvested and rapidly prepared in a few hours, provides a significant improvement over other therapies which require lengthy purification and culturing techniques of several weeks thus causing a critical delay in treatment. Further, the combination of autologous peripherial blood cells with antigen and IL-12 yields an unexpectedly high inhibition of tumor growth such that tumor regression or even disappearance occurs, and extraordinarily, living tumor challenges may not result in tumor occurrence.

CTLs are involved directly in the body's defense against any infection and are well-known to kill virus-infected cells. Further, as CTLs recognize foreign antigens in the context of class I MHC molecules, the invention is not restricted to the treatment of cancers but can be useful in the treatment of infectious diseases, especially viral diseases, for which an antigenic peptide that binds to class I MHC molecules can be admixed with autologous peripheral blood cells. It is not necessary for the practice of the invention that the antigenic peptide be provided in a purified or isolated state.

It is envisioned that the methods of the invention will be useful in the treatment of infectious, viral or parasitic diseases that are resistant to other therapies, such as arboviruses or malaria, or for which effective vaccines are not known, such as human immunodeficiency virus (HIV) and herpes viruses and certain arboviruses.

It is further envisioned that this invention can be useful surveillance therapies designed to prevent the recurrence of disease, such as tumor regeneration, and in preventative therapies such as vaccinations against viral or parasitic diseases, such as encephalitis or malaria.

Thus this invention provides novel methodology and immunization protocols which are surprisingly more effective in the generation of CTLs than conventional approaches and have the additional improvement of requiring less time to prepare the vaccine adjuvant or adjuvants compared to other therapies.

A further advantage of this invention is that few, if any, deleteriores side effects occur in the animal or patient through the administration of the vaccine adjuvant.

Peptide-based Immunization Strategies

In order to move towards immunization of melanoma patients, a methodology for peptide-based vaccination was required. Using the well-defined murine P815 system as a preclinical model (Brichard et al., 1995; Van den Eynde et al., 1991; Uyttenhove et al., 1980; Van Pel et al., 1985) and detection of specific CTL in peripheral blood as a surrogate readout, multiple immunization strategies were examined. Three weekly subcutaneous immunizations with peptide alone, peptide in several different adjuvants, or peptide plus IL-12 failed to induce detectable CTL. Next, in order to focus peptide delivery on APC, ex vivo pulsing of purified dendritic cells (DC) followed by their reinjection was attempted. This approach yielded CTL generation in 10–20% of mice. However, injection of peptide-pulsed DC plus IL-12 unexpectedly induced specific CTL in 100% of mice. Although a single injection of peptide-loaded DC on day 1 was sufficient, the IL-12 needed to be given during the several days after the immunization in order to be efficacious.

Generation of purified DC from each melanoma patient would be a cumbersome task, requiring several weeks of cell culture. Therefore, three additional sources of APC were examined: B cells activated by lipopolysaccharide, whole spleen cells, and non-fractionated peripheral blood mononuclear cells (PBMC). Interestingly, each of these cell populations pulsed with tumor antigen peptide also generated CTL in 100% of mice, but only if IL-12 was provided as well. The fact that pulsed PBMC plus IL-12 were sufficient simplifies considerably the procedure required for preparing the tumor antigen peptide-based vaccine. Successful immunization was achieved with two antigenic peptides P198 and P1A.

In order to determine whether peptide-pulsed APC could induce the generation of specific CTL in the human system, activated B cells or dendritic cells were isolated from a normal individual expressing HLA-A2. These cells were incubated with a peptide derived from MAGE-3 predicted to bind HLA-A2, and were used to stimulate $CD8^+$ T cells from the same individual. Only if IL-12 was included during the initial stimulation were specific CTL induced after expansion which could lyse melanoma cell lines expressing MAGE-3 (Van der Bruggen et al., 1994). Inasmuch as HLA-A2 is the most frequently expressed HLA allele and MAGE-3 is the most frequently expressed MAGE gene among melanoma samples examined, this peptide/HLA combination is suggested for human immunizations. A peptide derived from another tumor antigen, Melan A, also has been identified that binds to HCA-A2 and can be recognized by CTLs.

Tumor Antigen-Specific Immunization in a Murine Model

It is understood that the skilled artisan will recognize that the described system can be applicable to any number of cancers. Thus an illustrative list of tumors, tumor antibodies, etc. is provided in Tables 1 and 2 for which the described invention may be used. But for the purposes of providing an exemplary illustration, the tumor antigen P815 will be used.

TABLE 1

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| A: Gynecological GY | 'CA 125'>200 kD mucin GP | OC 125 | Kabawat et al., 1983; Szymendera, 1986 |
| ovarian | 80 Kd GP | OC 133 | Masuko et al, Cancer Res., 1984 |
| ovarian | 'SGA' 360 Kd GP | OMI | de Krester et al., 1986 |
| ovarian | High $M_r$ mucin | Mo v1 | Miotti et al, Cancer Res., 1985 |
| ovarian | High $M_r$ mucin/ glycolipid | Mo v2 | Miotti et al, Cancer Res., 1985 |
| ovarian | NS | 3C2 | Tsuji et al., Cancer Res., 1985 |
| ovarian | NS | 4C7 | Tsuji et al., Cancer Res., 1985 |
| ovarian | High $M_r$ mucin | $ID_3$ | Gangopadhyay et al., 1985 |
| ovarian | High $M_r$ mucin | DU-PAN-2 | Lan et al., 1985 |
| GY | 7700 Kd GP | F 36/22 | Croghan et al., 1984 |
| ovarian | 'gp 68' 48 Kd GP | $4F_7/7A_{10}$ | Bhattacharya et al., 1984 |
| GY | 40, 42kD GP | OV-TL3 | Poels et al., 1986 |
| GY | 'TAG-72' High $M_r$ mucin | B72.3 | Thor et al., 1986 |
| ovarian | 300-400 Kd GP | $DF_3$ | Kufe et al., 1984 |
| ovarian | 60 Kd GP | $2C_8/2F_7$ | Bhattacharya et al., 1985 |
| GY | 105 Kd GP | MF 116 | Mattes et al., 1984 |
| ovarian | 38-40 kD GP | MOv18 | Miotti et al., 1987 |
| GY | 'CEA' 180 Kd GP | CEA 11-H5 | Wagener et al., 1984 |
| ovarian | CA 19-9 or GICA | CA 19-9 (1116NS 19-9) | Atkinson et al., 1982 |
| ovarian | 'PLAP' 67 Kd GP | H17-E2 | McDicken et al., 1985 |
| ovarian | 72 Kd | 791T/36 | Perkins et al., 1985 |
| ovarian | 69 Kd PLAP | $NDOG_2$ | Sunderland et al., 1984 |
| ovarian | unknown $M_r$ PLAP | H317 | Johnson et al., 1981 |
| ovarian | $p185^{HER2}$ | 4D5, 3H4, 7C2, 6E9, 2C4, 7F3, 2H11, 3E8, 5B8, 7D3, SB8 | Shepard et al., 1991 |
| uterus ovary | HMFG-2 | HMFG2 | Epenetos et al., 1982 |
| GY | HMFG-2 | 3.14.A3 | Burchell et al., 1983 |
| B: BREAST | 330-450 Kd GP | DF3 | Hayes et al., 1985 |
| | NS | NCRC-11 | Ellis et al., 1984 |
| | 37kD | 3C6F9 | Mandeville et al., 1987 |
| | NS | MBE6 | Teramoto et al., 1982 |
| | NS | CLNH5 | Glassy et al., 1983 |
| | 47 Kd GP | MAC 40/43 | Kjeldsen et al., 1986 |
| | High $M_r$ GP | EMA | Sloane et al., 1981 |
| | High $M_r$ GP | HMFG1 HFMG2 | Arklie et al., 1981 |

TABLE 1-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | NS | 3.15.C3 | Arklie et al., 1981 |
| | NS | M3, M8, M24 | Foster et al., 1982 |
| | 1 (Ma) blood group Ags | M18 | Foster et al., 1984 |
| | NS | 67-D-11 | Rasmussen et al., 1982 |
| | oestrogen receptor | D547Sp, D75P3, H222 | Kinsel et al., 1989 |
| | EGF Receptor | Anti-EGF | Sainsbury et al., 1985 |
| | Laminin Receptor | LR-3 | Horan Hand et al., 1985 |
| | erb B-2 p185 | TA1 | Gusterson et al., 1988 |
| | NS | H59 | Hendler et al., 1981 |
| | 126 Kd GP | 10-3D-2 | Soule et al., 1983 |
| | NS | HmAB1,2 | Imam et al., 1984; Schlom et al., 1985 |
| | NS | MBR 1,2,3 | Menard et al., 1983 |
| | 95 Kd | 24.17.1 | Thompson et al., 1983 |
| | 100 Kd | 24.17.2 (3E1.2) | Croghan et al., 1983 |
| | NS | F36/22.M7/105 | Croghan et al., 1984 |
| | 24 Kd | C11, G3, H7 | Adams et al., 1983 |
| | 90 Kd GP | B6.2 | Colcher et al., 1981 |
| | CEA & 180 Kd GP | B1.1 | Colcher et al., 1983 |
| | colonic & pancreatic mucin similar to Ca 19-9 | Cam 17.1 | Imperial Cancer Research Technology MAb listing |
| | milk mucin core protein | SM3 | Imperial Cancer Research Technology Mab listing |
| | milk mucin core protein | SM4 | Imperial Cancer Research Technology Mab listing |
| | affinity-purified milk mucin | C-Mul (566) | Imperial Cancer Research Technology Mab listing |
| | p185$^{HER2}$ | 4D5 3H4, 7C2, 6E9, 2C4, 7F3, 2H11, 3E8, 5B8, 7D3, 5B8 | Shepard et al., 1991 |
| | CA 125 >200 Kd GP | OC 125 | Kabawat et al., 1985 |
| | High $M_r$ mucin/ glycolipid | MO v2 | Miotti et al., 1985 |
| | High $M_r$ mucin | DU-PAN-2 | Lan et al., 1984 |
| | 'gp48' 48 Kd GP | $4F_7/7A_{10}$ | Bhattacharya et al., 1984 |
| | 300-400 Kd GP | $DF_3$ | Kufe et al., 1984 |
| | 'TAG-72' high $M_r$ mucin | B72.3 | Thor et al., 1986 |
| | 'CEA' 180 Kd GP | cccccCEA 11 | Wagener et al., 1984 |
| | 'PLAP' 67 Kd GP | H17-E2 | McDicken et al., 1985 |
| | HMFG-2 >400 Kd GP | 3.14.A3 | Burchell et al., 1983 |
| | NS | FO23C5 | Riva et al., 1988 |
| C: COLORECTAL | TAG-72 High $M_r$ mucin | B72.3 | Colcher et al., 1987 |
| | GP37 | (17-IA) 1083-17-IA | Paul et al., 1986 |
| | Surface GP | C017-1A | LoBuglio et al., 1988 |
| | CEA | ZCE-025 | Patt et al., 1988 |
| | CEA | AB2 | Griffin et al., 1988a |
| | cell surface AG | HT-29-15 | Cohn et al., 1987 |
| | secretory epithelium | 250-30.6 | Leydem et al., 1986 |
| | surface glycoprotein | 44X14 | Gallagher et al., 1986 |
| | NS | A7 | Takahashi et al., 1988 |
| | NS | GA73.3 | Munz et al., 1986 |
| | NS | 791T/36 | Farrans et al., 1982 |
| | cell membrane & cytoplasmic Ag | 28A32 | Smith et al., 1987 |
| | CEA & vindesine | 28.19.8 | Corvalen, 1987 |
| | gp72 | X MMCO-791 | Byers et al., 1987 |
| | high $M_r$ mucin | DU-PAN-2 | Lan et al., 1985 |
| | high $M_r$ mucin | $ID_3$ | Gangopadhyay et al., 1985 |
| | CEA 180 Kd GP | CEA 11-H5 | Wagener et al., 1984 |
| | 60 Kd GP | $2C_8/2F_7$ | Bhattacharya et al., 1985 |
| | CA-19-9 (or GICA) | CA-19-9 (1116NS 19-9) | Atkinson et al., 1982 |
| | Lewis a | PR5C5 | Imperial Cancer Research Technology Mab Listing |
| | Lewis a | PR4D2 | Imperial Cancer Research Technology Mab Listing |
| | colonic mucus | PR4D1 | Imperial Cancer Research Technology Mab Listing |
| D: MELANOMA | p97$^a$ | 4.1 | Woodbury et al., 1980 |
| | p97$^a$ | 8.2 $M_{17}$ | Brown, et al., 1981a |
| | p97$^b$ | 96.5 | Brown, et al., 1981a |
| | p97$^c$ | 118.1, 133.2, (113.2) | Brown, et al., 1981a |
| | p97$^c$ | $L_1, L_{10}, R_{10}(R_{19})$ | Brown et al., 1981b |
| | p97$^d$ | $I_{12}$ | Brown et al., 1981b |
| | p97$^e$ | $K_5$ | Brown et al., 1981b |

TABLE 1-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
| --- | --- | --- | --- |
| | p155 | 6.1 | Loop et al., 1981 |
| | $G_{D3}$ disialoganglioside | R24 | Dippold et al., 1980 |
| | p210, p60, p250 | 5.1 | Loop et al., 1981 |
| | p280 p440 | 225.28S | Wilson et al., 1981 |
| | GP 94, 75, 70 & 25 | 465.12S | Wilson et al., 1981 |
| | P240–P250, P450 | 9.2.27 | Reisfeld et al., 1982 |
| | 100, 77, 75 Kd | F11 | Chee et al., 1982 |
| | 94 Kd | 376.96S | Imai et al., 1982 |
| | 4 GP chains | 465.12S | Imai et al., 1982; Wilson et al., 1981 |
| | GP 74 | 15.75 | Johnson & Reithmuller, 1982 |
| | GP 49 | 15.95 | Johnson & Reithmuller, 1982 |
| | 230 Kd | Me1-14 | Carrel et al., 1982 |
| | 92 Kd | Me1-12 | Carrel et al., 1982 |
| | 70 Kd | Me3-TB7 | Carrel et al., 1:387, 1982 |
| | HMW MAA similar to 9.2.27 AG | 225.28SD | Kantor et al., 1982 |
| | HMW MAA similar to 9.2.27 AG | 763.24TS | Kantor et al., 1982 |
| | GP95 similar to 376.96S 465.12S | 705F6 | Stuhlmiller et al., 1982 |
| | GP125 | 436910 | Saxton et al., 1982 |
| | CD41 | M148 | Imperial Cancer Research Technology Mab listing |
| E: GASTROINTESTINAL pancreas, stomach | high $M_r$ mucin | ID3 | Gangopadhyay et al., 1985 |
| gall bladder, pancreas, stomach | high $M_r$ mucin | DU-PAN-2 | Lan et al., 1985 |
| pancreas | NS | OV-TL3 | Poels et al., 1984 |
| pancreas, stomach, oesophagus | 'TAG-72' high Mr mucin | B72.3 | Thor et al., 1986 |
| stomach | 'CEA' 180 Kd GP | CEA 11-H5 | Wagener et al., 1984 |
| pancreas | HMFG-2 >400 Kd GP | 3.14.A3 | Burchell et al., 1983 |
| G.I. | NS | C COLI | Lemkin et al., 1984 |
| pancreas, stomach | CA 19-9 (Or GICA) CA50 | CA-19-9 (1116NS 19-9) and | Szymendera, 1986 |
| pancreas | CA125 GP | OC125 | Szymendera, 1986 |
| F: LUNG | p185$^{HER2}$ | 4D5 3H4, 7C2, 6E9, 2C4, 7F3, 2H1 1, 3E8, 5B8, 7D3, SB8 | Shepard et al., 1991 |
| non-small cell lung carcinoma | | | |
| | high $M_r$ mucin/ glycolipid | MO v2 | Miotti et al., 1985 |
| | 'TAG-72' high$M_r$ mucin | B72.3 | Thor et al., 1986 |
| | high Mr mucin | DU-PAN-2 | Lan et al., 1985 |
| | 'CEA' 180 kD GP | CEA 11-H5 | Wagener et al., 1984 |
| Malignant Gliomas | cytoplasmic antigen from 85HG-22 cells | MUC 8-22 | Stavrou, 1990 |
| | cell surface Ag from 85HG-63 cells | MUC 2-3 | Stavrou, 1990 |
| | cell surface Ag from 86HG-39 cells | MUC 2-39 | Stavrou, 1990 |
| | cell surface Ag from 86HG-39 cells | MUC 7-39 | Stavrou, 1990 |
| G: MISCELLANEOUS | p53 | PAb 240 PAb 246 PAb 1801 | Imperial Cancer Research Technology MaB Listing |
| small round cell tumors | neural cell adhesion molecule | ERIC.1 | Imperial Cancer Research Technology MaB Listing |
| medulloblastoma neuroblastoma rhabdomyosarcoma | | M148 | Imperial Cancer Research Technology MaB Listing |
| neuroblastoma | | FMH25 | Imperial Cancer Research Technology MaB Listing |
| renal cancer & glioblastomas | p155 | 6.1 | Loop et al., 1981 |
| bladder & laryngeal cancers | "Ca Antigen" 350–390 kD | CA1 | Ashall et al., 1982 |
| neuroblastoma | GD2 | 3F8 | Cheung et al., 1986 |

TABLE 1-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| Prostate | gp48 48 kD GP | $4F_7/7A_{10}$ | Bhattacharya et al., 1984 |
| Prostate | 60 kD GP | $2C_8/2F_7$ | Bhattacharya et al., 1985 |
| Thyroid | 'CEA' 180 kD GP | CEA 11-H5 | Wagener et al., 1984 | abbreviations: Abs, antibodies; Ags, antigens; EGF, epidermal growth factor; GI, gastrointestinal; GICA, gastrointestinal-associated antigen; GP, glycoprotein; GY, gynecological; HMFG, human milk fat globule; Kd, kilodaltons; Mabs, monoclonal antibodies; $M_r$, molecular weight; NS, not specified; PLAP, placental alkaline phosphatase; TAG, tumor-associated glycoprotein; CEA, carcinoembryonic antigen.

footnotes: the CA 19-9 Ag (GICA) is sialosylfucosyllactotetraosylceramide, also termed sialylated Lewis pentaglycosyl ceramide or sialyated lacto-N-fucopentaose II; p97 Ags are believed to be chondroitin sulphate proteoglycan; antigens reactive with Mab 9.2.27 are believed to be sialylated glycoproteins associated with chondroitin sulphate proteoglycan; unless specified, GY can include cancers of the cervix, endocervix, endometrium, fallopian tube, ovary, vagina or mixed Mullerian tumor; unless specified GI can include cancers of the liver, small intestine, spleen, pancreas, stomach and oesophagus.

TABLE 2

HUMAN TUMOR CELL LINES AND SOURCES

| ATTC HTB NUMBER | CELL LINE | TUMOR TYPE |
|---|---|---|
| 1 | J82 | Transitional-cell carcinoma, bladder |
| 2 | RT4 | Transitional-cell papilloma, bladder |
| 3 | ScaBER | Squamous carcinoma, bladder |
| 4 | T24 | Transitional-cell carcinoma, bladder |
| 5 | TCCSUP | Transitional-cell carcinoma, bladder, primary grade IV |
| 9 | 5637 | Carcinoma, bladder, primary |
| 10 | SK-N-MC | Neuroblastoma, metastasis to supra-orbital area |
| 11 | SK-N-SH | Neuroblastoma, metastasis to bone marrow |
| 12 | SW 1088 | Astrocytoma |
| 13 | SW 1783 | Astrocytoma |
| 14 | U-87 MG | Glioblastoma, astrocytoma, grade III |
| 15 | U-118 MG | Glioblastoma |
| 16 | U-138 MG | Glioblastoma |
| 17 | U-373 MG | Glioblastoma, astrocytoma, grade III |
| 18 | Y79 | Retinoblastoma |
| 19 | BT-20 | Carcinoma, breast |
| 20 | BT-474 | Ductal carcinoma, breast |
| 22 | MCF7 | Breast adenocarcinoma, pleural effusion |
| 23 | MDA-MB-134-VI | Breast, ductal carcinoma, pleural effusion |
| 24 | MDA-MD-157 | Breast medulla, carcinoma, pleural effusion |
| 25 | MDA-MB-175-VII | Breast, ductal carcinoma, pleural effusion |
| 27 | MDA-MB-361 | Adenocarcinoma, breast, metastasis to brain |
| 30 | SK-BR-3 | Adenocarcinoma, breast, malignant pleural effusion |
| 31 | C-33 A | Carcinoma, cervix |
| 32 | HT-3 | Carcinoma, cervix, metastasis to lymph node |
| 33 | ME-180 | Epidermoid carcinoma, cervix, metastasis to omentum |
| 34 | MS751 | Epidermoid carcinoma, cervix, metastasis to lymph node |
| 35 | SiHa | Squamous carcinoma, cervix |
| 36 | JEG-3 | Choriocarcinoma |
| 37 | Caco-2 | Adenocarcinoma, colon |
| 38 | HT-29 | Adenocarcinoma, colon, moderately well-differentiated grade II |
| 39 | SK-CO-1 | Adenocarcinoma, colon, ascites |
| 40 | HuTu 80 | Adenocarcinoma, duodenum |
| 41 | A-253 | Epidermoid carcinoma, submaxillary gland |
| 43 | FaDu | Squamous cell carcinoma, pharynx |
| 44 | A-498 | Carcinoma, kidney |
| 45 | A-704 | Adenocarcinoma, kidney |
| 46 | Caki-1 | Clear cell carcinoma, consistent with renal primary, metastasis to skin |
| 47 | Caki-2 | Clear cell carcinoma, consistent with renal primary |
| 48 | SK-NEP-1 | Wilms' tumor, pleural effusion |
| 49 | SW 839 | Adenocarcinoma, kidney |
| 52 | SK-HEP-1 | Adenocarcinorna, liver, ascites |
| 53 | A-427 | Carcinoma, lung |
| 54 | Calu-1 | Epidermoid carcinoma grade III, lung, metastasis to pleura |
| 55 | Calu-3 | Adenocarcinoma, lung, pleural effusion |
| 56 | Calu-6 | Anaplastic carcinoma, probably lung |
| 57 | SK-LU-1 | Adenocarcinoma, lung consistent with poorly differentiated, grade III |
| 58 | SK-MES-1 | Squamous carcinoma, lung, pleural effusion |
| 59 | SW 900 | Squamous cell carcinoma, lung |
| 60 | EB1 | Burkitt lymphoma, upper maxilla |

TABLE 2-continued

HUMAN TUMOR CELL LINES AND SOURCES

| ATTC HTB NUMBER | CELL LINE | TUMOR TYPE |
|---|---|---|
| 61 | EB2 | Burkitt lymphoma, ovary |
| 62 | P3HR-1 | Burkitt lymphoma, ascites |
| 63 | HT-144 | Malignant melanoma, metastasis to subcutaueous tissue |
| 64 | Malme-3M | Malignnt melanoma, metastasis to lung |
| 66 | RPMI-7951 | Malignant melanoma, metastasis to lymph node |
| 67 | SK-MEL-1 | Malignant melanoma, metastasis to lymphatic system |
| 68 | SK-MEL-2 | Malignant melanoma, metastasis to skin of thigh |
| 69 | SK-MEL-3 | Malignant melanoma, metastasis to lymph node |
| 70 | SK-MEL-5 | Malignant melanoma, metastasis to axillary node |
| 71 | SK-MEL-24 | Malignant melanoma, metastasis to node |
| 72 | SK-MEL-28 | Malignant melanoma |
| 73 | SK-MEL-31 | Malignant melanoma |
| 75 | Caov-3 | Adenocarcinoma, ovary, consistent with primary |
| 76 | Caov-4 | Adenocarcinoma, ovary, metastasis to subserosa of fallopian tube |
| 77 | SK-OV-3 | Adenocarcinoma, ovary, malignant ascites |
| 78 | SW 626 | Adenocarcinoma, ovary |
| 79 | Capan-1 | Adenocarcinoma, pancreas, metastasis to liver |
| 80 | Capan-2 | Adenocarcinoma, pancrease |
| 81 | DU 145 | Carcinoma, prostate, metastasis to brain |
| 82 | A-204 | Rhabdomyosarcoma |
| 85 | Saos-2 | Osteogenic sarcoma, primary |
| 86 | SK-ES-1 | Anaplastic osteosarcoma versus Ewing sarcoma, bone |
| 88 | SK-LMS-1 | Leiomyosarcoma, vulva, primary |
| 91 | SW 684 | Fibrosarcoma |
| 92 | SW 872 | Liposarcoma |
| 93 | SW 982 | Axilla synovial sarcoma |
| 94 | SW 1353 | Chondrosarcoma, humerus |
| 96 | U-2 OS | Osteogenic sarcoma, bone primary |
| 102 | Malme-3 | Skin fibroblast |
| 103 | KATO III | Gastric carcinoma |
| 104 | Cate-1B | Embryonal carcinoma, testis, metastasis to lymph node |
| 105 | Tera-1 | Embryonal carcinoma, malignancy consistent with metastasis to lung |
| 106 | Tera-2 | Embryonal carcinoma, malignancy consistent with, metastasis to lung |
| 107 | SW579 | Thyroid carcinoma |
| 111 | AN3 CA | Endometrial adenocarcinoma, metastatic |
| 112 | HEC-1-A | Endometrial adenocarcinoma |
| 113 | HEC-1-B | Endometrial adenocarcinoma |
| 114 | SK-UT-1 | Uterine, mixed mesodermal tumor, consistent with leiomyosarcoma grade III |
| 115 | SK-UT-1B | Uterine, mixed mesodermal tumor, consistent with leiomyosarcoma grade III |
| 117 | SW 954 | Squamous cell carcinoma, vulva |
| 118 | SW 962 | Carcinoma, vulva, lymph node metastasis |
| 119 | NCI-H69 | Small cell carcinoma, lung |
| 120 | NCI-H128 | Small cell carcinoma, lung |
| 121 | BT-483 | Ductal carcinoma, breast |
| 122 | BT-549 | Ductal carcinoma, breast |
| 123 | DU4475 | Metastatic cutaneous nodule, breast carcinoma |
| 124 | HBL-100 | Breast |
| 125 | Hs 578Bst | Breast, normal |
| 126 | Hs 578T | Ductal carcinoma, breast |
| 127 | MDA-MB-330 | Carcinoma, breast |
| 128 | MDA-MB-415 | Adenocarcinoma, breast |
| 129 | MDA-MB-435S | Ductal carcinoma, breast |
| 130 | MDA-MB-436 | Adenocarcinoma, breast |
| 131 | MDA-MB-453 | Carcinoma, breast |
| 132 | MDA-MB-468 | Adenocarcinoma, breast |
| 133 | T-47D | Ductal carcinoma, breast, pleural effusion |
| 134 | Hs 766T | Carcinoma, pancreas, metastatic to lymph node |
| 135 | Hs 746T | Carcinoma, stomach, metastatic to left leg |
| 137 | Hs 695T | Amelanotic melanoma, metastatic to lymph node |
| 138 | Hs 683 | Glioma |
| 140 | Hs 294T | Melanoma, metastatic to lymph node |
| 142 | Hs 602 | Lymphoma, cervical |
| 144 | JAR | Choriocarcinoma, placenta |
| 146 | Hs 445 | Lymphoid, Hodgkin's disease |
| 147 | Hs 700T | Adenocarcinoma, metastatic to pelvis |
| 148 | H4 | Neuroglioma, brain |
| 151 | Hs 696 | Adenocarcinoma primary, unknown, metastatic to bone-sacrum |
| 152 | Hs 913T | Fibrosarcoma, metastatic to lung |
| 153 | Hs 729 | Rhabdomyosarcoma, left leg |
| 157 | FHs 738Lu | Lung, normal fetus |

TABLE 2-continued

HUMAN TUMOR CELL LINES AND SOURCES

| ATTC HTB NUMBER | CELL LINE | TUMOR TYPE |
|---|---|---|
| 158 | FHs 173We | Whole embryo, normal |
| 160 | FHs 738B1 | Bladder, normal fetus |
| 161 | NIH:OVCAR-3 | Ovary, adenocarcinoma |
| 163 | Hs 67 | Thymus, normal |
| 166 | RD-ES | Ewing's sarcoma |
| 168 | ChaGo K-1 | Bronchogenic carcinoma, subcutaneous metastasis, human |
| 169 | WERI-Rb-1 | Retinoblastoma |
| 171 | NCI-H446 | Small cell carcinoma, lung |
| 172 | NCI-H209 | Small cell carcinoma, lung |
| 173 | NCI-H146 | Small cell carcinoma, lung |
| 174 | NCI-H441 | Papillary adenocarcinoma, lung |
| 175 | NCI-H82 | Small cell carcinoma, lung |
| 176 | H9 | T-cell lymphoma |
| 177 | NCI-H460 | Large cell carcinoma, lung |
| 178 | NCI-H596 | Adenosquamous carcinoma, lung |
| 179 | NCI-H676B | Adenocarcinoma, lung |
| 180 | NCI-H345 | Small cell carcinoma, lung |
| 181 | NCI-H820 | Papillary adenocarcinoma, lung |
| 182 | NCI-H520 | Squamous cell carcinoma, lung |
| 183 | NCI-H661 | Large cell carcinoma, lung |
| 184 | NCI-H510A | Small cell carcinoma, extra-pulmonary origin, metastatic |
| 185 | D283 Med | Medulloblastoma |
| 186 | Daoy | Medulloblastoma |
| 187 | D341 Med | Medulloblastoma |
| 188 | AML-193 | Acute monocyte leukemia |
| 189 | MV4-11 | Leukemia biphenotype |

Although P815 is a mastocytoma and not a melanoma cell line, it is likely that the principles of tumor antigen immunity defined with this model system are generally applicable to other tumor types. The advantages of the system are multiple. Five tumor antigens expressed by P815 have been identified according to recognition by CTL clones (Brichard et al., 1995), and the gene P1A encoding two of these antigens has been cloned and characterized (Van den Eynde et al., 1991). The genomic sequence of P1A in P815 tumor cells is identical to that in normal mouse cells, indicating that it is a normal gene that is abnormally expressed. It is expressed by several mastocytoma cell lines but not in normal tissues except for testis and placenta, and in this way mirrors the expression of the human tumor antigen genes of the MAGE family (Van Pel et al., 1995). In addition, immunogenic tum⁻ variants have been generated by mutagenesis of P815 (Uyttenhove et al., 1980). These variants express at least one neoantigen as a result of point mutations in normally expressed genes (Sibille et al., 1990; Wolfel et al., 1987; De Plaen et al., 1988), resulting in their being rejected by the majority of syngeneic mice. The description of a point mutation generating a human melanoma antigen (Coulie et al., 1995) adds yet another parallel between the P815 system and human tumors. A highly transfectable variant of P815, P1.HTR, also has been generated that facilitates transfection by calcium phosphate precipitation (Van Pel et al., 1995). This variant has been used for all the studies requiring transfection.

Peptides encoded by several of the unique tumor antigens of the tum⁻ variants have been defined, such as the P198 peptide used in one of the examples herein. The P198 peptide is more hydrophilic than the P1A peptide. Therefore, initial peptide-based immunization studies were performed using the more soluble P198 peptide. Information gained was then examined using P1A peptide as well. Studies with P1A are important in order to measure efficacy of immunization in vivo in terms of protection against living tumor challenge and regression of pre-established tumors. These types of studies would not be possible with P198 because that tumor is rejected spontaneously.

The studies described herein provide convincing evidence that both B7 and IL-12 should be provided during active tumor antigen immunization. Although B7 apparently can be recruited under some circumstances from host immune cells, IL-12 apparently cannot.

Groups of 6–10 female DBA/2 mice were treated for each condition examined. In the first studies, naive (non-tumor-bearing) mice were immunized. The studies were performed by pulsing different APC with P198 peptide at 1 $\mu$g/ml. These procedures were performed next using P1A peptide in an identical fashion, with peptide-specific CTL activity from peripheral blood measured as a surrogate readout. Cytokine production, particularly IFN-$\gamma$ and TNF-$\alpha$, were assessed in parallel studies following restimulation of effector T cells with peptide-pulsed syngeneic APCs or antigen-expressing tumor cell lines.

The optimal dose of peptide for immunization was determined. Whole syngeneic splenocytes are pulsed with 10 or 1 $\mu$g/ml of P1 A peptide, washed, irradiated (2,000 rad), and injected into the mice. The optimal number of injections was assessed. One advantage of using peripheral blood as a source of T lymphocytes to assay is that the mice do not need to be sacrificed in order to measure CTL activity. In this way, levels of CTL activity were examined at weekly intervals prior to each immunization. This approach is analogous to that which is used for patient studies. A general goal of the pre-clinical model was to construct a specific procedure that was then transferred to patient use. The optimal location of immunization is not yet known. Pulsed APC were injected subcutaneously, intradermally, intravenously, and intraperitoneally, and CTL activity were measured as before.

Although non-fractionated lymphoid cell populations can function for immunization, it was not clear whether the few DC present in the mixture were actually responsible for the effect. Both spleen cells and PBMC contain a population of DC precursors. Nonetheless, the inventors reasoned that many cell types can serve as APC for immunization, provided IL-12 is administered as well. The hypothesis was tested rigorously by comparing pulsed purified resting B cells, activated B cells, DC, and fibroblasts. If each of these class I MHC$^+$ APC populations induced specific CTL when pulsed with peptide and co-injected with IL-12, then the conclusion that provision of IL-12 makes the nature of the APC irrelevant could be made. Finally, PBMC were isolated from mice and used for immunization in a similar fashion. Isolation of sufficient numbers of mouse PBMC is difficult, but success using this cell population as a source of APC bridges even more closely to the clinical situation, as PBMC constitute the easiest APC population to isolate from humans.

Conditions that generated positive results using CTL induction as a readout were then explored by challenging immunized mice with living P815 or P1.HTR cells to assess for tumor protection. A related tumor, L1210, that has been transfected with the tumor antigen gene P1A was also used. A comparison between the ability to protect against L1210 versus L1210.P1A served as a measure of the antigen specificity of the immune response. The optimal conditions observed in the tumor protection assays were then transferred to the immunization of mice bearing pre-established tumors. Tumors were established subcutaneously or intraperitoneally. Beginning 4, 7, 10, or 14 days later, immunization with P1A-pulsed APC plus EL-12 was initiated. The rate of regression of tumor growth was determined. The inventors deduced that the protocols that are most efficacious at inducing rejection of pre-established tumors in the mouse model may be the most important to apply to human patients, as these individuals will possess pre-established tumors as well.

Peptide-pulsed APC in Humans

Peripheral blood macrophages as a source of APC have been cultured from the blood of melanoma patients, pulsed with a peptide derived from MAGE-1, and injected back into the patients subcutaneously and intravenously (Mukheiji et al., 1995), No major toxicities were observed. Biopsy of the immunization sites revealed the presence of MAGE-1-specific CTL, suggesting that a specific immune response was initiated. Based on the success in the mouse model using non-fractionated PBMC as a source of APC, the inventors reasoned that it may not be necessary to carry out a procedure for in vitro expansion of macrophages or DC to obtain a successful immunization. The use of non-fractionated PBMC would simplify considerably the preparation of the vaccine, and avoid potential sources of toxicity.

Phase I/Phase II Experience with IL-12 in Humans

A Phase I clinical study of recombinant human IL-12 (rhIL-12) in patients with various malignancies was performed. A single test dose of rhIL-12 was administered intravenously, followed in 2 wk by a daily dose for 5 days, every 3 wk. Cohorts of at least 4 patients received rhIL-12 at dose levels of 3, 10, 30, 100, 250, 500, or 1000 ng/kg/day. Toxicities included transient cytopenias (nadirs occurring 2–5 days after treatment), reversible increases of transaminases and bilirubin, transient hyperglycemia, stomatitis, and capillary leak syndrome. The maximally tolerated dose at this schedule was 500 ng/kg/day, and there were several tumor responses observed.

A second Phase I clinical study of rhIL-12 was conducted, employing subcutaneous administration 3 times a wk for 2 wk, followed by one wk off. Patients were treated at dose levels of 3, 10, 30, 100, and 300 ng/kg/day. The maximally tolerated dose was not achieved as the trial was suspended after a clinical hold was placed on the Phase II renal cell carcinoma studies described below.

Two Phase II studies of rhIL-12 administered intravenously to patients with advanced renal cell carcinoma were initiated. The dose of 500 ng/kg/day was administered intravenously 5 times per wk followed by a 16 day rest period. Unexpectedly, 12 of the 17 patients enrolled required hospitalization for adverse events, and there were 4 patient deaths. Two of these were attributed to rhIL-12 and 2 were related to progressive disease. Therefore, the trial was suspended. After lengthy investigation into the potential differences between the Phase I and Phase II trials, it appeared that the toxicity profile was highly dependent on the schedule of administration of rhIL-12. The toxicity in the Phase I study apparently was attenuated by the single test dose given prior to the daily dosing.

Based on these observations, a third Phase I study of rhIL-12 was completed. Cohorts of 6 patients were treated by subcutaneous injection 3 times per wk for 2 wk followed by a 9 day rest period, at doses of 30, 100, and 300 ng/kg/day. There were no major toxicities, and 3 patients were then treated at a 500 ng/kg/day dose. Two renal cell carcinoma patients appeared to have a minor response. This dose range and schedule of rhIL-12 appear to be well tolerated in patients with advanced malignancies.

Overview of the Approach to Tumor Antigen-Specific Immunization

Based on the above preclinical and Phase I results, the inventors conceived of a strategy for tumor antigen-specific immunization of melanoma patients. A Phase I/Phase II study in metastatic melanoma patients was undertaken. Patients were first HLA-typed. HLA-A2-positive patients underwent a tumor biopsy to screen for expression of MAGE-3 and Melan-A using RT-PCR™. Patients with MAGE-3$^+$ tumors were eligible for vaccination with MAGE-3 peptide. Patients with tumors that were MAGE-3-negative but Melan-A-positive were eligible for immunization with Melan-A peptide.

Peripheral blood was collected and fractionated by density centrifugation to isolate PBMC as a source of APC. Cells were incubated with the appropriate MAGE-3 or Melan-A peptide, washed, resuspended in PBS, and lethally irradiated. Pulsed cells (50–100×10$^6$) were injected subcutaneously at 2 sites, near lymph node locations but not adjacent to a tumor mass. The subcutaneous route was preferred for the reasons of safety, efficacy in the preclinical model, and the goal of targeting the vaccine to a draining lymph node.

Eligible patients were assigned to the respective cohorts as they came, whether being immunized with MAGE-3 or Melan-A peptide. Three to six patients were treated with peptide-pulsed PBMC alone, using either MAGE-3 or Melan-A peptide as indicated. For the remaining cohorts, rhIL-12 was administered subcutaneously near one of the immunization sites on days 1, 3, and 5. The dose of rhIL-12 was escalated in groups of 3–6 patients each, to determine an optimal dose with respect to safety and successful immunization. The dosing schedule was based on the most recent phase I data. Reimmunization was performed at 3 wk intervals, with rhIL-12 administration on days 1, 3, and 5 of each cycle. Prior to each immunization, peripheral blood was collected to assay for peptide-specific CTL activity and production of IFN-γ and TNF-α. Injection sites also were examined for local inflammation indicative of a delayed-type hypersensitivity reaction. Clinical response was assessed as a secondary outcome.

One major advantage of the tumor antigen-specific immunization approach is the ability to measure a specific immune response independently of an effect on tumor regression which has not been possible with more generic immunotherapies, such as injection of recombinant IL-2, because the antigens expressed by the patient's tumor are not normally analyzed. In addition, any successfully generated response might be directed against antigens that are not yet characterized and therefore would go undetected. A first step to improving upon immunotherapy of cancer is to determine whether or not successful immunization has occurred; only then can vaccination be improved upon in order to determine its true potential in cancer therapy.

The appropriate surrogate readout of immunization is not yet known. It is generally felt that induction of antigen-specific cytolytic activity is the desired endpoint. However, other properties of the effector cells induced might be just as critical. A likely candidate is the ability of the activated CTL to produce the cytokines IFN-γ and TNF-α, a characteristic of a Th1/Tc1 phenotype. Studies in the murine model have suggested that a Th1/Tc1 phenotype might be optimal for mediating rejection of pre-established tumors.

Three measures of successful immunization of patients are examined. First, the serum samples collected from each patient following each immunization are assayed for IFN-γ and TNF-α content. The inventors reasoned that effectively immunized patients have an increase in these cytokines after each inoculation, and that the magnitude of the increase is greater with each subsequent vaccination. These cytokines are measured by standard ELISA technique well known to those of skill in the art. Serial dilutions of the serum sample are compared to serial dilutions of a standard. The dilutions giving half-maximal absorption are compared and the concentration is determined based on the known concentration of the standard. This surrogate readout can be performed routinely, but the sensitivity of the assay might not be sufficient to detect the expected increases.

The second assay measures MAGE-3- or MelanA-specific cytolytic activity from the cryopreserved PBMC which is assessed by re-stimulating the T lymphocytes with peptide-pulsed APC, expanding the responding cells with IL-2, and measuring lysis of chromium-labeled target cells expressing the correct MHC molecules and pulsed with MAGE-3 or MelanA peptide. Controls include non-pulsed targets and the NK-sensitive target K562. Cold competition is performed with non-radiolabelled K562 cells to eliminate non-specific NK activity.

The third readout is a combination of the first and the second approaches. Because a Th1/Tc2 phenotype might be predictive of anti-tumor efficacy, the effector cells generated upon expansion of specific T cells in the second method are stimulated for 24 hours with peptide-pulsed APC, and the supernatants are assayed for the presence of IFN-γ and TNF-α. Even if the serum levels are undetectable, cytokine production by the antigen-specific T cells should be easily measurable.

Outline of a Specific Human Vaccination Study

Figure 10:
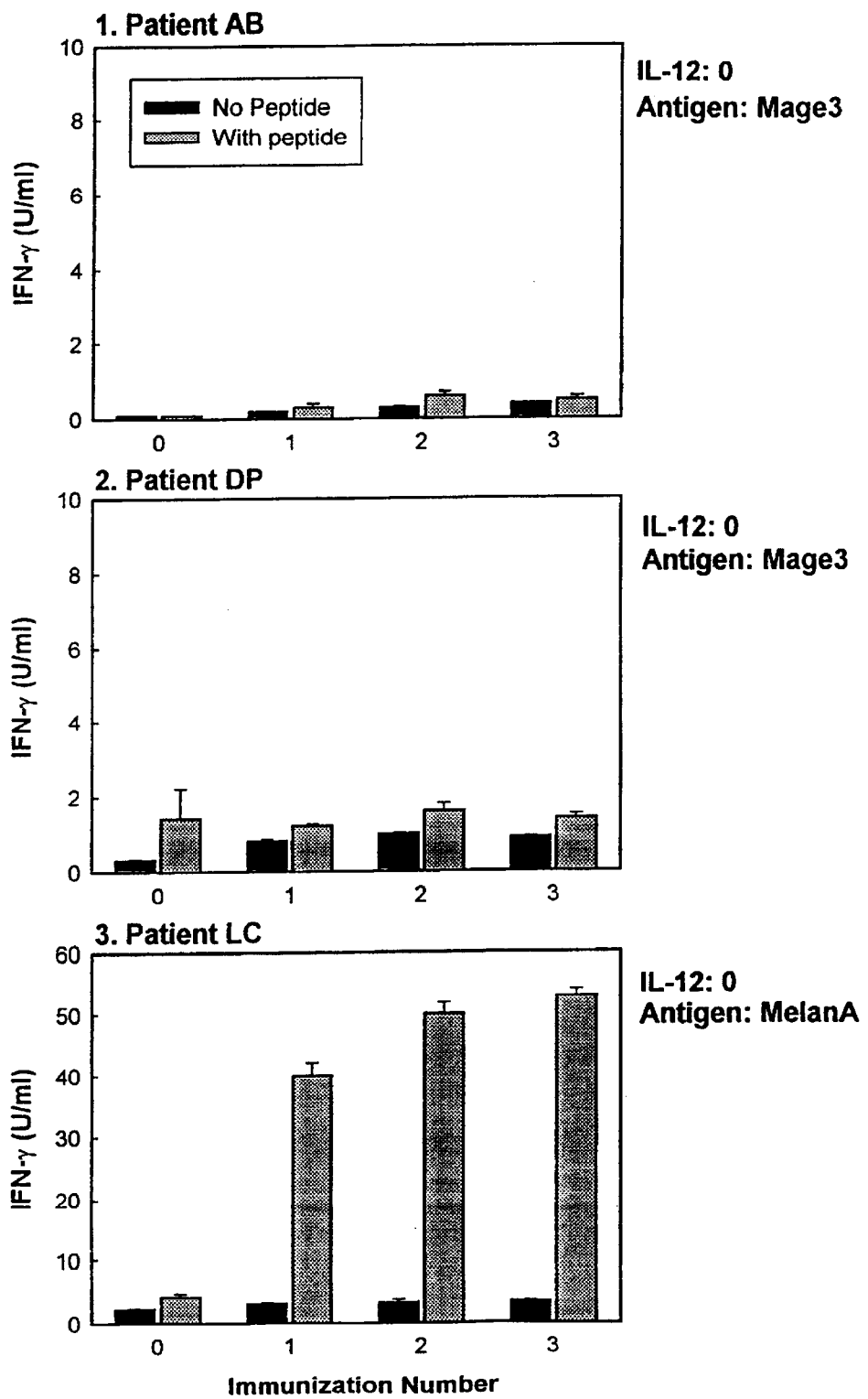
FIG. 10. Vaccination of melanoma patients with refractory metastatic disease was demonstrated using tumor antigen peptide-pulsed autologous PBMC without rhIL-12. Generation of peptide-specific, IFN-γ-producing $CD8^+$ T cells was detected after 1 to 3 immunizations with Mage3 (10 μm) or MelanA (50 μm). MelanA-specific responses appeared to be detected earlier than Mage3-specific responses.
Figure 11:
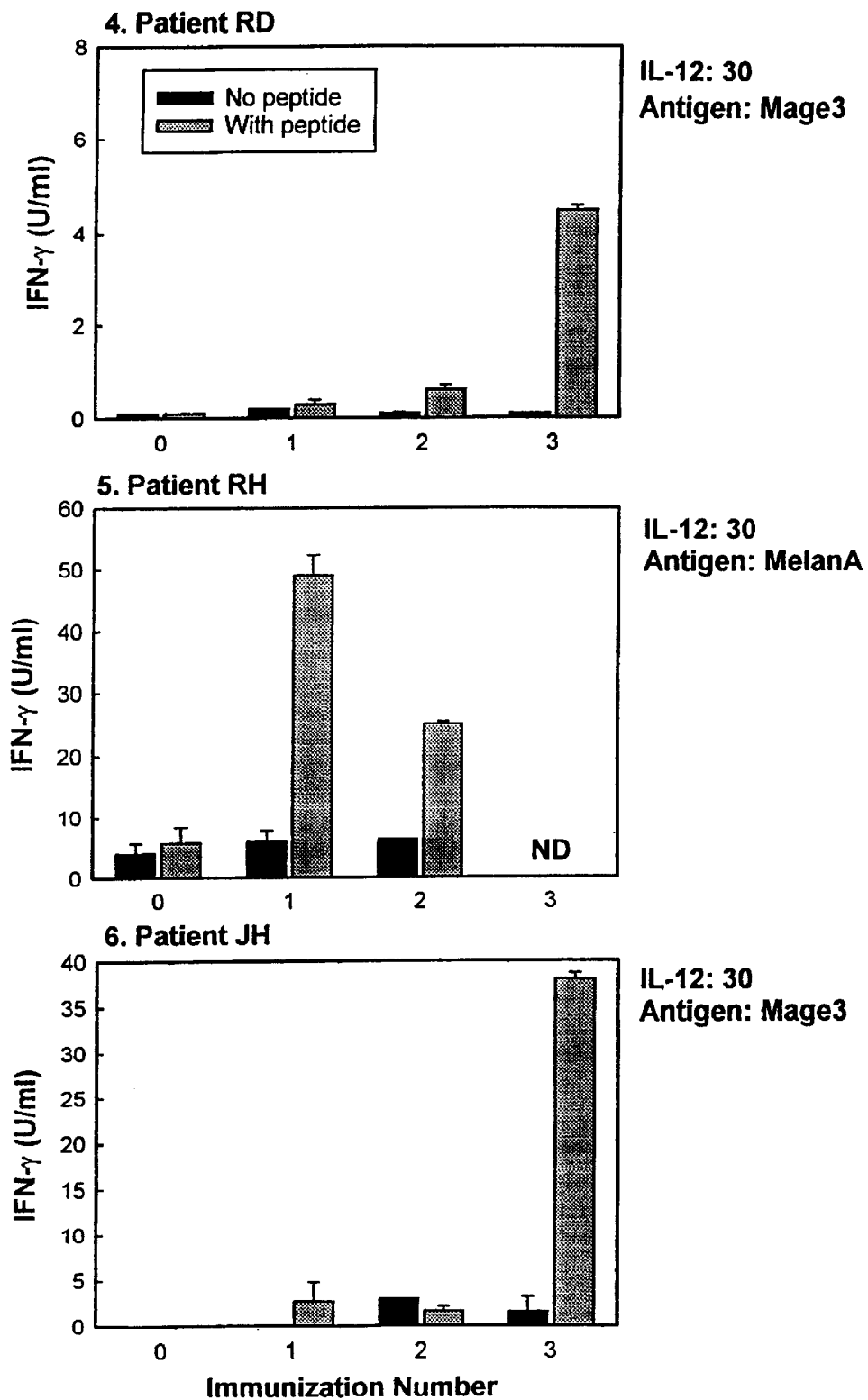
FIG. 11. Vaccination of melanoma patients with refractory metastatic disease was demonstrated using tumor antigen peptide-pulsed autologous PBMC with 30 ng/kg rhIL-12. Generation of peptide-specific, IFN-γ-producing $CD8^+$ T cells was detected after 1 to 3 immunizations with Mage3 (10 μm) or MelanA (50 μm). MelanA-specific responses appeared to be detected earlier than Mage3-specific responses.

A vaccination study of patients with refractory metastatic disease was conducted using tumor antigen peptide pulsed autologous PBMC with and without rhIL-12. In particular, using Mage3 and MelanA, generation of peptide-specific, IFN-γ-producing CD8$^+$ T cells was detected after 1 to 3 immunizations as shown in FIG. 10, FIG. 11. and FIG. 12.

Biological Functional Equivalents

It is understood that the therapeutic regimen described herein can be utilized with any antigenic peptide that binds to class I MHC molecules. For the MAGE-3 and Melan A peptides described, biological functional equivalents are described. As will be understood by those of skill in the art, modification and changes may be made in the structure of the recombinant peptide and still obtain a molecule having like or otherwise desirable characteristics. For example, certain amino acids may be substituted for other amino acids in a protein structure without appreciable loss of interactive binding capacity with structures such as, for example, antigen-binding regions of T cell antigen receptors or binding sites on HLA molecules of melanoma cells. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventor that various changes may be made in the sequence of recombinant proteins or peptides (or underlying DNA) without appreciable loss of their biological utility or activity.

In terms of functional equivalents, it is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the antigenic recognition region, such residues may not generally be exchanged.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.3±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

CODON TABLE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The term "functionally equivalent codon" is used herein to refer to codons that encode the same amino acid, such as the six codons for arginine or serine, and also refers to codons that encode biologically equivalent amino acids (see Codon Table, above).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Therapeutic Regimens and Dosage

A therapeutic regimen is described herein; however, the treatment with L-12 may precede or follow administration of peptide-pulsed APC by intervals ranging from seconds to hours to days to even weeks. In embodiments where peptide-pulsed APC and IL-12 are administered separately to the patient, one would generally ensure that a significant period of time did not expire between the time of each delivery, such that the combination of the two would still be able to exert an advantageously combined effect on the recipient. In such instances, it is contemplated that one would contact the patients with both agents within about 0.1 to 24 hours of each other and, even, within about 1 to 4 hours of each other, with a delay time of only about 1 hour to about 2 hours being preferred. In some situations, it is desirable to extend the time period for treatment significantly; where several days (1, 2, 3, 4, 5, 6 or 7) to several weeks (1, 2, 3, 4, 5, 6, 7 or 8) lapse between the respective administrations.

It also is conceivable that more than one administration of peptide-pulsed APC will be desired in certain circumstances in combination with IL-12. Various combinations may be employed, where peptide-pulsed APC is "A" and IL-12 is "B":

| | | | | |
|---|---|---|---|---|
| A/B/B | B/A/A | A/A/B | | |
| A/B/A | B/A/B | B/B/A | | |
| B/B/B/A | B/B/A/B | B/A/B/A | B/A/A/B | |
| A/A/B/B | A/B/A/B | A/B/B/A | B/B/A/A | |
| A/A/A/B | B/A/A/A | A/B/A/A | | |
| B/A/B/B | A/A/B/A | A/B/B/B | | |

To achieve tumor cell killing, both agents are delivered to a patient in a combined amount effective to kill the tumor cells. These treatment cycles can be repeated multiple times, or delivered only once.

The skilled artisan will recognize that factors that are well known to influence patient response to drug therapy include, but are not limited to, species, age, weight, gender, health, pregnancy, addictions, allergies, ethnic origin, prior medical conditions, current medical condition and length of treatment. Thus, the skilled artisan will be well acquainted with the need to individualize dosage(s) to each patient.

The skilled artisan will also consider the condition that is to be treated prior to selecting the appropriate dosage. For example, a dosage that is appropriate for the treatment of a cancer, may not be the desired dosage for subsequent surveillance therapy designed to prevent the recurrence of the cancer.

Thus it is recognized that in the practice of the invention a wide variety of dosages may be useful and that the desired dosage is individualized to the patient. In an illustrative case, 10–50 $\mu$M peptide is loaded onto APCs, 10×10$^8$ APCs are administered per injection and 30–50 ng/kg IL-12 is administered per injection.

Yet the amount of peptide loaded onto APCs may be as little as about 0.1 $\mu$M to as much as about 1 mM. It is understood that this range includes 0.1, 0.2, 0.3, 0.4, 0.5, 0.6, 0.7, etc.; 1, 2, 3, 4, 5, 6, 7, 8, 9, 10, 11, 12, 13, 14, 15, etc.; 20, 21, 22, 23, etc.; 25, 26, 27, 28 etc.; 30, 31, 32, 33, etc.;

35, 36, 37, etc.; 40, 41, 42 etc.; 45, 46, 47, etc.; 50, 51, 52, 53, etc.; 60, 61, 62, etc.; 70, 71, 72, etc.; 80, 81, 82, etc.; 90, 91, 92, etc.; 100, 110, 120, etc.; 150, 160, 170, etc.; 200, 210, 220, etc.; 250, 260, 270 etc.; 300, 310, 320, 330, etc.; 350, 360, 370, etc.; 400, 410, 420, etc.; 450, 460, 470, etc.; 500, 525, 550, 575, etc.; 600, 625, 650, etc.; 700, 725, 750, etc.; 800, 825, 850, etc.; 900, 925, 950, etc.; 1000 µm.

The number of APCs per injection may also be varied from $1\times10^6$–$1\times10^9$. It is understood that this range is inclusive of all doses between about $1\times10^6$ and $\times10^9$. Thus this range includes $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$ and $9\times10^8$ APCs per injection.

The amount of IL12 which can be administered ranges from 1 ng/kg–1000 ng/kg per injection. It is understood that this range is inclusive of all doses between about 1 ng/kg and about 1000 ng/kg. Thus this range includes 1, 2, 3, 4, 5, 6, 7, 8, 9, 10, 11, 12, 13, 14, 15, etc.; 20, 21, 22, 23, etc.; 25, 26, 27, 28 etc.; 30, 31, 32, 33, etc.; 35, 36, 37, etc.; 40, 41, 42 etc.; 45, 46, 47, etc.; 50, 51, 52, 53, etc.; 60, 61, 62, etc.; 70, 71, 72, etc.; 80, 81, 82, etc.; 90, 91, 92, etc.; 100, 110, 120, etc.; 150, 160, 170, etc.; 200, 210, 220, etc.; 250, 260, 270 etc.; 300, 310, 320, 330, etc.; 350, 360, 370, etc.; 400, 410, 420, etc.; 450, 460, 470, etc.; 500, 525, 550, 575, etc.; 600, 625, 650, etc.; 700, 725, 750, etc.; 800, 825, 850, etc.; 900, 925, 950, etc.; 1000 ng/kg.

Treatment Routes

Peptide-pulsed APC and IL-12 can be administered intravenously, intraarterially, intratumorally, parenterally or intraperitoneally. In the invention, the preferred routes of administration are subcutaneous (SC); however, intravenous (IV), intrarterial, and intraperitoneal (IP) can be used. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be m brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Although it is not envisioned as a preferred route, either or both peptide-pulsed APC and IL-12 may also be orally administered, for example, with an inert diluent or with an assimilable edible carrier, or enclosed in hard or soft shell gelatin capsule, or compressed into tablets, or incorporated directly with the food of the diet. For oral therapeutic administration, the active compound may be incorporated with excipients and used in the form of ingestible tablets, buccal tables, troches, capsules, elixirs, suspensions, syrups, wafers, and the like. Such compositions and preparations should contain at least 0.1% of the active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Screening and Monitoring Effectiveness of Therapy

It is contemplated that in the context of the present invention one may remove cells, either tumor, normal or both tumor and normal cells, from an individual in order to either monitor the progress of treatment or as a part of the treatment. It is expected that one may monitor the effectiveness of treatment by removing such cells and treating such cells with DAPI staining to determine the level of chromatin condensation, measuring the level of apoptosis, measuring the level of neutral sphingomyelinase production or other methods such as the following.

One particular method for determining induction of apoptosis is terminal deoxynucleotidyl transferase mediated dUTP-biotin nick end labeling (TUNEL) assays, which measure the integrity of DNA (Gorczyca, 1993). This assay measures the fragmentation of DNA by monitoring the incorporation of labeled UTP into broken DNA strands by the enzyme terminal transferase. The incorporation can be monitored by electroscopy or by cell sorting methodologies (e.g., FACS).

Another method with which it is expected that one may monitor the effectiveness of treatment is the use of enzyme linked immunosorbent assays (ELISAs).

ELISAs

Certain preferred immunoassays are the various types of ELISAs and radioimmunoassays (RIA) known in the art. Immunohistochemical detection using tissue sections is also particularly useful. However, it will be readily appreciated that detection is not limited to such techniques, and western blotting, dot blotting, ELISPOT, FACS analyses, and the like may also be used.

In one exemplary ELISA, an antibody against a cytokine, such as IFGγ, is immobilized onto a selected surface exhibiting protein affinity, such as a well in a polystyrene microtiter plate. Then, a composition containing the counterpart cytokine is added to the wells. After binding and washing to remove non-specifically bound complexes, the bound cytokine protein complex may be detected. Detection is generally achieved by the addition of an anti-cytokine or anti-tumor protein antibody that is linked to a detectable label. Detection may also be achieved by the addition of a first anti-cytokine or anti-tumor protein antibody, followed by a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immune complexes. These are described as follows:

In coating a plate with the primary antibody, one will generally incubate the wells of the plate with a solution of the agent, either overnight or for a specified period of hours. The wells of the plate will then be washed to remove incompletely adsorbed material. Any remaining available surfaces of the wells are then "coated" with a nonspecific protein that is neutral with regard to binding to the biological components. These include bovine serum albumin (BSA), casein, and solutions of milk powder. The coating allows for blocking of nonspecific adsorption sites on the immobilizing surface and thus reduces the background caused by nonspecific binding of proteins onto the surface.

In the ELISAs of the present invention it will probably be more customary to use a secondary or tertiary detection means. Thus, after binding of the first protein to the well, coating with a non-reactive material to reduce background, and washing to remove unbound material, the immobilizing surface is contacted with the second biological protein under conditions effective to allow protein complex formation. Detection of the complex then requires a labeled binding ligand or antibody.

"Under conditions effective to allow protein complex formation" means that the conditions preferably include diluting the tumor antigen and cytolkine proteins, with solutions such as BSA, bovine gamma globulin (BGG) and phosphate buffered saline (PBS)/Tween. These added agents also tend to assist in the reduction of nonspecific background. The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific complexes between the test sample and the originally bound material, and subsequent washing, the occurrence of even minute amounts of bound complexes may be determined.

To provide for detection, a first or second antibody will preferably be provided that has an associated label to allow detection. Preferably, the label will be an enzyme that will generate color development upon incubating with an appropriate chromogenic substrate. Thus, for example, one will desire to contact and incubate the bound complexes with a urease, glucose oxidase, alkaline phosphatase or hydrogen peroxidase-conjugated antibody for a period of time and under conditions that favor the development of immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethylbenzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Ex vivo Delivery

In the present invention, it is contemplated that systemic delivery of either or both peptide-pulsed APC and IL-12 may be used. It is further contemplated that in practicing the claimed invention that one will wish to alter the PBMC by ex vivo manipulation. Ex vivo gene therapy refers to the isolation of cells from an animal or patient, the delivery of a nucleic acid into the cells in vitro, and then the return of the modified cells back into an animal or individual. This may involve the surgical removal of tissue/organs from an animal or patient or the primary culture of cells and tissues.

APC can be prepared from PBMC isolated by density centrifugation of whole blood. Human mononuclear cells (MNC), prepared from bone marrow also can be used as APC. Bone marrow can be obtained from the tibiae, femora, spine, ribs, hips, sternum, as well as the humeri, radi, ulna, tibiae, and fibulae. Additionally, these cells also can be obtained from cord blood, peripheral blood, or cytokine-mobilized peripheral blood. Other sources of human hematopoietic stem cells include embryonic yolk sac, fetal liver, fetal and adult spleen, and blood. The marrow layer is centrifuged over a density gradient to produce a pellet of red cells at the bottom of the tube, a clear layer of media, an interface layer which contains the MNC and a plasma medium layer on top. The interface layer may then be removed using, for example, suction. Centrifugation of this layer at 1000 g ultimately yields a MNC pellet. This pellet may then be resuspended in a suitable buffer for cell sorting by FACS. The isolated MNC can be cultured in vitro to expand the immunologically active cells. The expanded, therapeutically active cells are then loaded with peptide and provided to the patient to obtain a therapeutic effect.

APC also can be dendritic cells, generated from bone marrow or peripheral blood. Fibroblasts can serve as APC, and then can be cultured from tissues such as the skin.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Successful Immunization with Peptide-pulsed PBMC plus rmIL-12 Obviates the Need to Use Dendritic Cells Materials and Methods Mice. DBA/2 mice were bred and housed in a pathogen-free facility. Female mice 8–10 weeks of age were used for studies.

Cell lines and transfectants. P815 mastocytoma cells were cultured in DMEM supplemented with 10% FCS and incubated at 37° C. in a 8% $CO_2$ atmosphere. Various clones of P815 were used in this study: P1.HTR, a highly transfectable variant of P815; P1, a tumorigenic clone of P815; P198 a tum⁻ clone of P815; P511, an azaguanine-resistant variant of P815; and P1204, a P815AB-negative variant carrying a deletion of gene P1A (Uyttenhove et al. 1983). P815.B7-1 and P198.B7-1 cells were obtained by electroporation respectively of P1 and P198 cells with the B7-1 cDNA cloned by PCR™ into plasmid pcDSRα and with the plasmid pRc/RSV (Invitrogen, San Diego, Calif.) conferring neomycin resistance. L1210 is a leukemia cell line derived from a DBA/2 mouse, which was cultured under the same conditions as P815 cells. L1210 transfectants expressing antigen P815AB (L1210.P1A) were generated by co-electroporation of the C1A.3.1 cosmid (Gajewski et al., 1995) with plasmid pSVtkneob conferring neomycin resistance. L1210.P1A.B71 cells were obtained by transfection of L1210.P1A cells with the murine B7-1 cDNA cloned into plasmid pEFBOS (Gajewski et al., 1995) (containing a puromycin resistance gene) by electroporation, and selection with puromycin and limiting dilution cloning. All transfectants were maintained in selection drug at least every second passage; for in vivo injections the cells were always cultured in the absence of the selection drug.

CTL clones. CTL P1:5, a clone specific for antigen P815A, and the P198.3 CTL clone specific for P198, were cultivated in 1 ml cultures containing $5 \times 10^6$ irradiated DBA/2 spleen cells and $10^5$ irradiated (10,000 rad) P1 cells (for clone P1:5) or P198 cells (for clone P198.3) as stimulators. In addition, cultures contained 50% of supernatant from secondary mixed lymphocyte culture (MLC) as a source of cytokines.

Tumor peptides. Peptides were synthesized and purified by reverse phase HPLC and characterized by amino acid analysis using standard techniques. The single letter code sequences of the peptides used are as follows: H-2K$^d$-restricted P198, KYQAVTTTL (SEQ ID NO: 1), and H-2L$^d$-restricted P815AB, LPYLGWLVF (SEQ ID NO:2).

rmIL-12. As source of rmIL-12, initial studies were performed using a hexahistidine-tagged IL-12 fusion protein expressed in and purified from transfected mammalian cells, as described (Fallarino et al., 1996). All the principal studies were repeated using highly purified rmIL-12.

Purification and preparation of antigen presenting cells. Splenocytes obtained from naive DBA/2 female mice were used as a source to prepare the following antigen presenting cells (APCs):

Dendritic cells (DC): Splenocytes were washed twice in medium contain 0.5% normal mouse serum (NMS) and were allowed to adhere for two hours at 37° C. (Steinman et al, 1979). Plates were washed three times with the same medium and incubated over night at 37° C. After this second incubation, non-adherent cells were pooled as DC and FACS analysis showed between 70% and 90% DC as assessed by staining with mAb N418.

Unfractionated splenocytes: Pools of DBA/2 splenocytes were washed twice in medium containing 0.5% NMS then counted and incubated with the specific tumor peptide and used in in vivo or in vitro studies.

LPS blasts: In this case spleen cell suspensions ($10 \times 10^6$/ ml) were cultured for 48 hours at 37° C. in 10 cm² tissue culture dishes in medium containing 0.5% NMS in the presence of LPS (25 µg/ml). Living cells were then harvested washed 3 times to remove excess of LPS. FACS analysis with an anti-B220 mAb and anti-IgM showed approximately 80% of the cells were activated B cells.

Resting B cells: Splenocytes were washed twice in medium containing 0.5% NMS and allowed to adhere for two hours at 37° C.; non-adherent cells were removed and washed twice and incubated for 30 min. at 4° C. with anti-Thy-1 and anti-MAC-1 (M170) mAb. After washing, the antibody-bounded cells were lysed by treatment with rabbit complement at 37° C. for 30 min. The cells were washed again and the remaining cells were recovered after sedimentation over Ficoll-Hypaque. Greater than 98% of the recovered cells were B cells based on FACS analysis with anti-B220 and anti-IgM antibodies.

Peripheral blood mononuclear cells (PBMC): Approximately 1 ml of blood was obtained retroorbitally from several DBA/2 mice, red blood cells were lysed with ACK lysis buffer, and the mononuclear cell fraction was recovered after Ficoll-gradient purification.

FACS analysis. $1 \times 10^6$ cells in 100 µl of FACS buffer (PBS containing 3% FCS and 0.02% sodium azide) were stained in v-bottom microtiter plates with FITC-conjugated mAbs specific for MHC-class I (30-5-7S), I-A$^d$ (MKD6), B7-1 (16-10A1), B7-2 (GL1), CD11c (N418), or B220 (RA3-6B2) at 4° C. for 30 min. The cells were then washed with FACS buffer and analyzed on a FACS can flow cytometer (Becton Dickinson, San Jose, Calif.). 10,000 cells were collected for each sample and the data were analyzed by using Lysis II software.

In vitro pulsing with peptide and immunization with tumor peptide pulsed APC. All peptide pulsing was done in the absence of FCS or other proteins, in DPBS only. APC were washed twice in DPBS (GIBCO) and resuspended in PBS at $5-10 \times 10^6$ cells/ml in 50 ml polypropylene tubes (Falcon). Cells were incubated with either the P198 or P1A peptide (1 µM or 10 µM) in a total volume of 5–10 ml at 37° C. with occasional agitation for 1–2 hours. The cells were then washed, irradiated (2000 rad), and resuspended so that the indicated number of pulsed cells for each study could be delivered in 100 µl DPBS. DBA/2 mice were immunized weekly with the indicated cell number (or DPBS alone) in 100 ml in both hind footpads. In some studies, the same cells were co-administered with rmIL-12 (10 ng in 50 µl per footpad) followed by additional rmIL-12 injections in each footpad on days 1 and 2.

Mixed lymphocyte-tumor culture (MLTC). MLTCs were performed using either spleen cells or PBMC as a source of responding lymphocytes. Spleen cells ($5 \times 10^6$) were stimulated with $2 \times 10^5$ irradiated (10,000 rad) P198 or L1210.P1A cells, or the same cells transfected with B7-1. The cells were incubated in 2 ml per well in 24 well plates, and CTL activity was measured 6–7 days later. Stimulation of peripheral blood lymphocytes was performed by mixing $3 \times 10^5$ Ficoll-purified PBMC with $10^5$ irradiated stimulating cells (10,000 rad) and $2 \times 10^6$ irradiated (2000 rad) normal syngeneic spleen cells 1 ml per well of 48-well plates. CTL activity was assessed after 6–7 days.

Chromium-release assay. Effector cells were diluted in duplicate in v-bottom microtiter plates and mixed with 2000 $^{51}$Cr-labeled target cells in a final volume of 200 μl of complete medium. In some studies, $10^5$ cold competitor cells were mixed with the labeled target cells before addition to the effector cells. Supernatants were collected after incubation for 4 hours at 37° C. and radioactivity was measured using a 96-well plate counter (Packard Instruments). The percentage of $^{51}$Cr-specific release was calculated as described.

In vivo tumor protection assays. Two weeks following the last immunization, mice were challenged by s.c. injection in the left flank with $1 \times 10^6$ P1.HTR tumor cells in 100 μl of DPBS. The size of the tumors was assessed twice per week by measuring the largest and smallest diameters. Data are reported as the average of the tumor diameters at each time point. All studies included five mice per group and were repeated at least twice.

RESULTS

Figure 2:
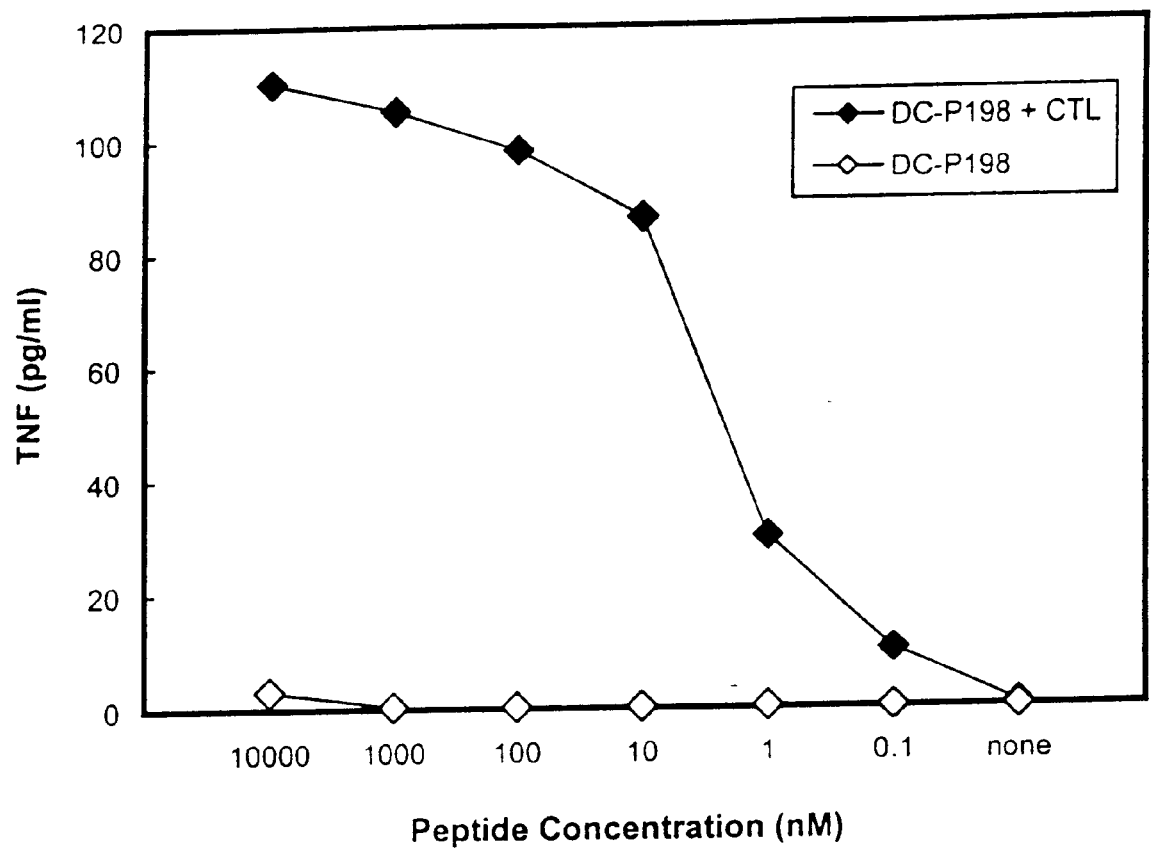
FIG. 2. Production of TNF by CTL P198.6 clone stimulated with sDC pulsed with various doses of P198 tumor peptide. sDC were pulsed with the indicated concentrations of P198 peptide, washed, and co-cultured with (solid symbols) or without (open symbols) the P198-specific CTL clone P198.6 for 24 hours. The TNF content of the supernatant was evaluated by determining its toxicity on WEHI-164 cells.
Figure 3:
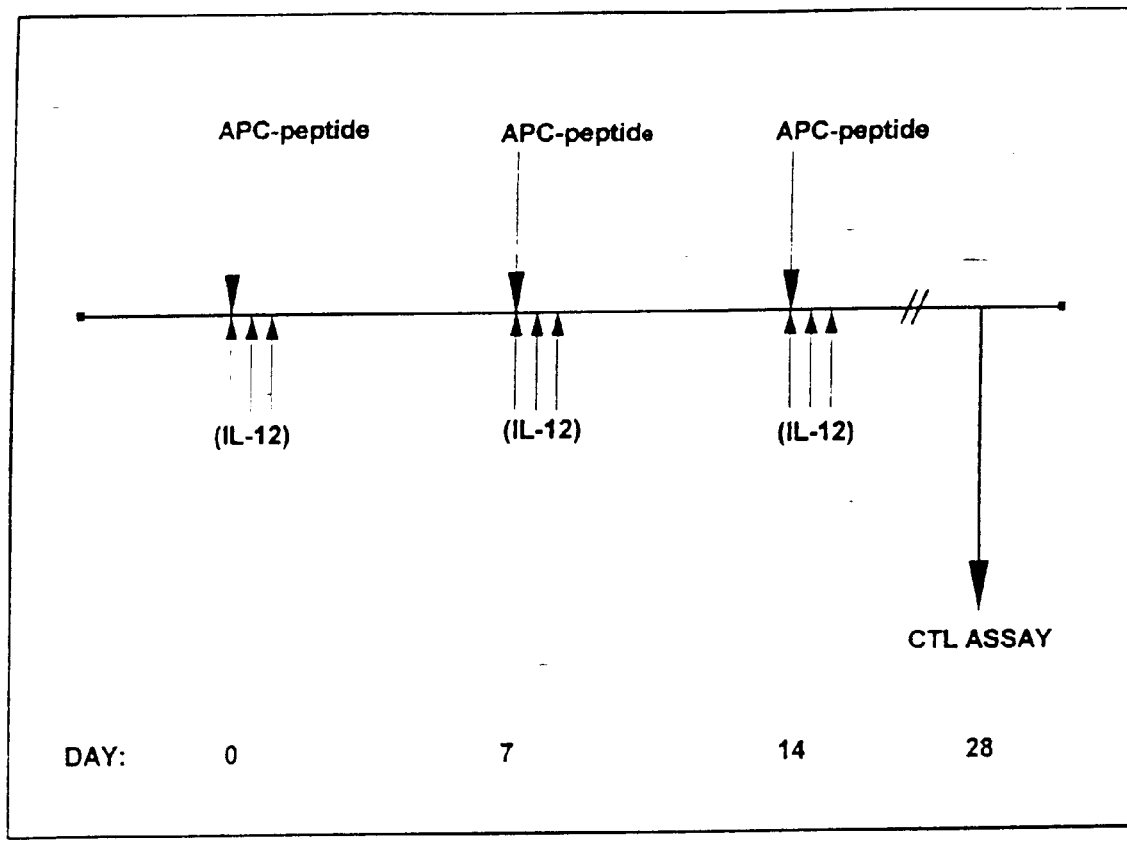
FIG. 3. Scheme of immunization with P198-peptide loaded APCs. In all immunization studies, DBA/2 mice (usually 5 per group) were injected weekly for three consecutive weeks with various peptide-loaded APCs. rmIL-12 also was administered in some studies, and was injected along with peptide-pulsed APC on the day of each immunization on day 0, and again on days 1 and 2 as shown. Two weeks following the last immunization, spleen cells or PBMC were restimulated with the appropriate tumor cells and the specific cytolytic activity was determined after 6–7 days of culture.
Figure 4:
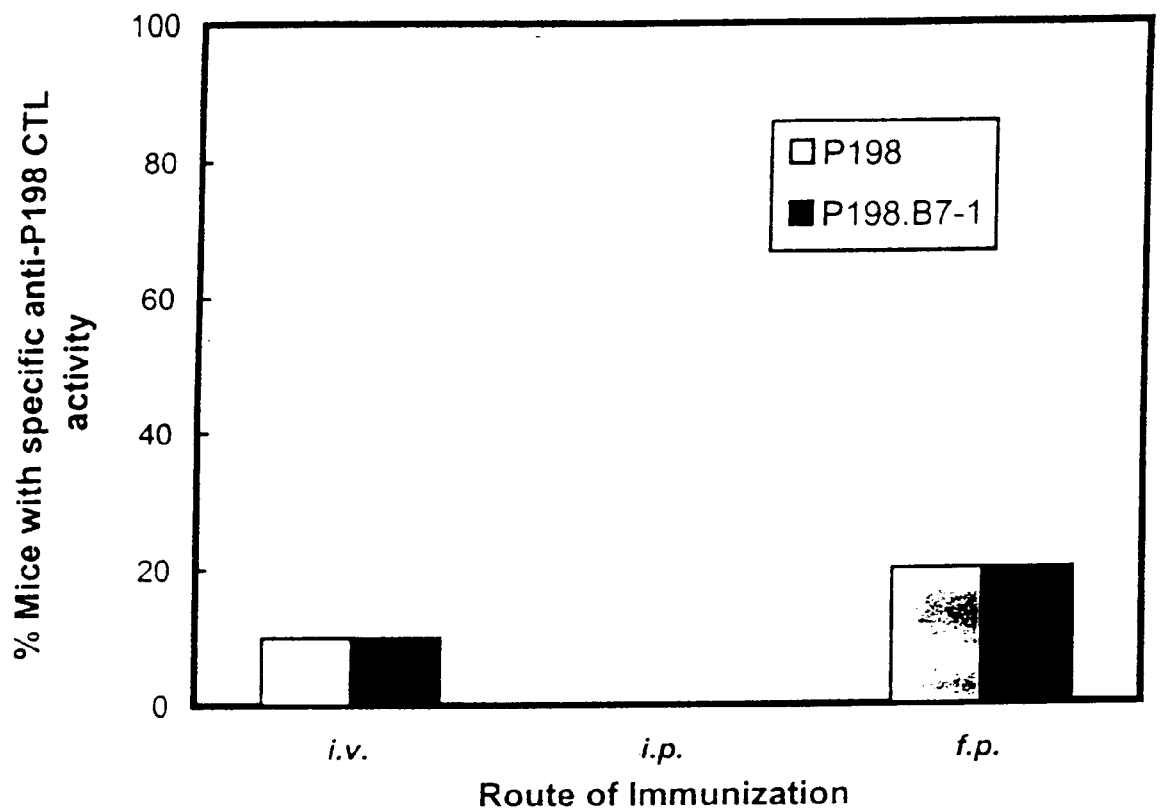
FIG. 4. Proportion of mice with specific CTL activity after immunization with P198 peptide-pulsed sDC. DBA/2 mice (5 group) were immunized weekly for three consecutive weeks with $5\times10^5$ P198-pulsed sDC in DPBS either i.v, i.p, or divided between both hind footpads (f.p.). Two weeks after the last immunization, an MLTC was performed with P198 cells (open bars), or P198.B7-1 cells (filled bars) as stimulators. Cytolytic activity was analyzed at day 6 against P198 or P511 in the presence of unlabeled P511 as a cold target. Control mice received sDC alone or PBS, neither of which induced detectable CTL. Mice were considered to be positive if the specific lysis at E:T ratio 100:1 was greater than 25 and if the difference between lysis of P198 and P511 was greater than 15. Similar results were observed in two studies.

P198-peptide pulsed spleen-derived dendritic cells are recognized by a P198-specific CTL clone but are unable to prime efficiently a P198-specific T cell response in vivo. In order to work toward a tumor antigen peptide-based immunization approach that could be applied to human cancer patients, vaccination strategies employing peptide-pulsed dendritic cells were explored in the P815 murine tumor model. Several tumor antigen genes have been cloned from P815 and its "tub" variants, and the specific antigenic peptides recognized by CTL have been characterized. The $K^d$-restricted antigen P198 and the $L^d$-restricted antigen P1A (Uyttenhove et al, 1980) were studied in detail. Dendritic cells were purified from DBA spleen using the adherence/de-adherence method first described by Steinman (Steinman et al., 1979). DC isolated in this way were >90% N418$^+$ and expressed high levels of B7-1, B7-2, and class I and II MHC molecules (FIG. 1). They also were very effective at stimulating in a primary allogeneic mixed-lymphocyte reaction. To assess the ability of sDC to present functional peptide/MHC complexes on the cell surface, they were pulsed with various doses of the P198 peptide and then cultured in the presence of the specific CTL clone CTL P198.6. sDC pulsed with the specific P198 peptide stimulated the secretion of TNF by CTL P198.6 in a dose-dependent fashion, at concentrations as low as 0.1 nM (FIG. 2). Plateau stimulation occurred at approximately 100 nM of peptide. sDC incubated in the absence of P 198 peptide or in the absence of the CTL clone did not result in specific cytokine production (FIG. 2).

sDC pulsed with P198 peptide were next used to immunized syngeneic DBA mice in vivo. Naive DBA/2 mice were inoculated weekly for three consecutive weeks with $5 \times 10^5$ sDC that had been pulsed in vitro with 1 μM P198 peptide. This concentration was chosen to ensure that the plateau levels of stimulation observed with the CTL clone in vitro could be maintained in vivo, but to avoid too high a peptide concentration that might preferentially generate T cells with low-affinity TCRs. Pulsed cells were injected either i.v., i.p., or intra-footpad (f.p.); control groups were injected with PBS or with sDC incubated only in PBS during the peptide pulsing period. Two weeks after the third immunization, spleen cells were harvested and stimulated in vitro in a 6 day MLTC. The general scheme for the immunization schedule is depicted in FIG. 3. Since it was shown previously that the presence of the costimulatory molecule B7-1 on the stimulator cells can improve the detection of anti-tumor CTL responses (Gajewski et al., 1996), two different stimulation conditions were used in the MLTC, either control- or B7-1-transfected P198 tumor cells. Lytic activity was tested on P198 and on the negative control cell line P511. As shown in FIG. 4, specific CTL induction was detected in only 10–20% of mice, using either the footpad or i.v. routes of immunization. Specific CTL were not detected when the P198 peptide-pulsed sDC were administered i.p. The magnitude of CTL activity and the number of mice with specific cytotoxicity were the same when the stimulation in vitro was performed with or without tumor cells expressing the costimulatory molecule B7-1 (FIG. 4). These results demonstrate that sDC pulsed with P198 peptide were able to present correctly the peptide to a differentiated CTL clone in vitro, but were unable to prime mice effectively to generate detectable CTL activity in the majority of mice in vivo.

CTL responses in mice immunized with P198-pulsed sDC in combination with rmIL-12. Because the importance of IL-12 during rejection of immunogenic P815 tumor variants in vivo was demonstrated previously (Fallarino et al., 1996), and because of the ability of this cytokine to promote a lytic Th1/Tc1 phenotype, exogenous rmIL-12 was administered along with the P198-pulsed sDC during the immunization protocol. All subsequent immunizations were performed via the footpad route. Naive DBA/2 mice were immunized weekly for three consecutive weeks with sDC pulsed with 1 μM P198 peptide as before. In addition, rmIL-12 (10 ng per footpad per day), was injected in the same sites on the day of immunization and on the subsequent two days (FIG. 3). Control mice received sDC incubated with no peptide, sDC plus rmIL-12, or just PBS. As shown in Table 1, co-administration of rmIL-12 along with the peptide-pulsed sDC generated specific anti-P198 cytolytic activity in 100% of the mice while injection of P198 peptide-pulsed sDC did not elicit specific CTL activity. As observed previously, the ability to detect specific CTL was not improved by using P198.B7-1 cells to stimulate in the MLTC. Furthermore, in these studies comparable levels of lytic activity were detected when using spleen or PBMC as a source of primed T cells (Table 1). The use of PBMC as a source of T cells to assess for specific CTL generation brought the system closer to clinical application, and also allowed the mice to live in order to determine the duration of anti-tumor immunity and the capability of immunized mice to reject a tumor challenge. All subsequent CTL determinations were assessed using PBMC. The rationale for administering a low dose of rmIL-12 on days 0, 1, and 2 rather than a single large dose on day 0 only, was to bias the effect of IL-12 toward the local draining lymph nodes rather than try to distribute it systemically, and to ensure that the IL-12 would be bathing the local lymph node or nodes at the time T cells were expected to make contact with APCs. In fact, when rmIL-12 was administered on day 0 of each immunization only, specific CTL activity was detected in a smaller fraction of mice (Table 1). In other studies, no CTL activity was detected when IL-12 was given on day 0 only. Collectively, these results demonstrate that immunization with P198 peptide-pulsed sDC was far more effective at eliciting CTL responses when exogenous IL-12 was co-administered as well.

TABLE 1

Proportion of DBA/2 mice with specific CTL activity after immunization with P198 tumor peptide loaded DC plus rmIL-12
FRACTION WITH P198 SPECIFIC CTL DETECTED IN:

| IMMUNIZATION* | SPLEEN | PERIPHERAL BLOOD |
|---|---|---|
| DC-P198 | 0/6 | 0/6 |
| DC-P198 + rmIL-12 (day 0) | 3/6 | 3/6 |
| DC-P198 + rmIL-12 (days 0, 1 and 2) | 6/6 | 6/6 |
| DC-IL-12 | 0/3 | 0/3 |
| PBS | 0/3 | 0/3 |

*DBA/2 mice (6 per group) were immunized with 5 × 10⁵ sDC pulsed with 1 μM P198 peptide as indicated in FIG. 3. rmIL-12 was injected either on day 0 only, or on days 0, 1, and 2 of each immunization. Cytolytic activity was analyzed 2 weeks after the third immunization using either spleen cells (column 1) or PBMC (column 2) as a source of responding cells. Mice were considered to be positive if the specific lysis at an E:T ratio of 100:1 was greater than 25 and if the difference between lysis of P198 and P511 was greater than 15.

Immunization with P198 peptide-pulsed splenocytes, B cells, or PBMC induces CTL activity in vivo, provided rmIL-12 is co-administered. The ability of IL-12 to augment the ability of pulsed sDC to immunize in vivo prompted examination of other sources of APC that might be simpler to obtain, thus being easier to apply to human immunization protocols. It was also desirable to examine cell types that normally are poor APC or even tolerogenic when used alone. The inventors' reasoning was that provision of IL-12 might make any class I⁺ cell capable of initiating a CTL response upon re-injection in vivo. To this end, unfractionated splenocytes, PBMC, resting B cells, or LPS-activated B cells were prepared from naive DBA/2 mice. FIG. 1 shows the level of expression of class I and class II MHC molecules on these cell populations, as well as the levels of costimulatory molecules B7-1 or B7-2.

Figure 5A:
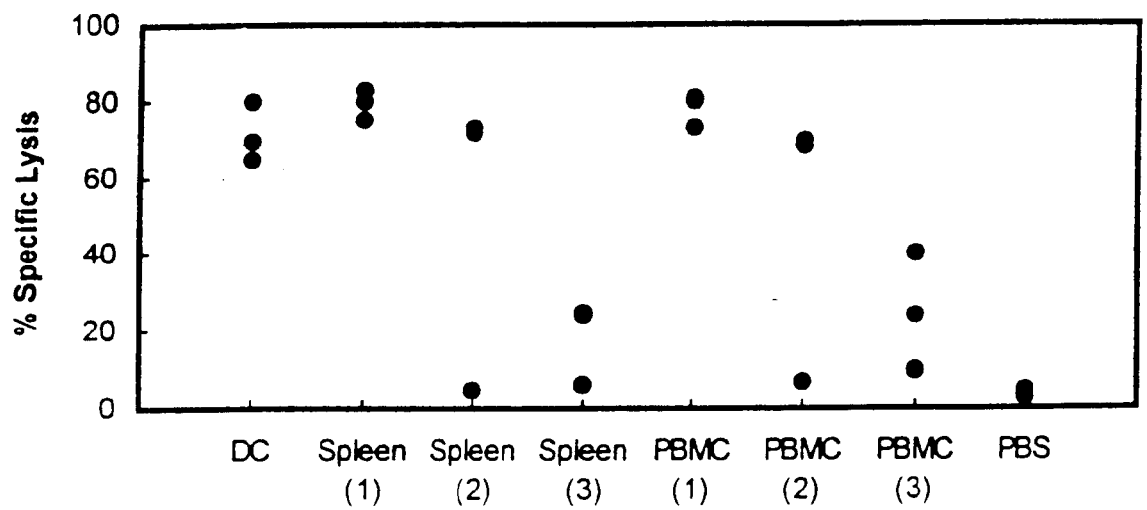
FIG. 5A and FIG. 5B. Immunization of naive mice with various APCs pulsed with P198 peptide in combination with rmIL-12. Naive DBA/2 mice were immunized with P198 peptide-pulsed sDC, splenocytes, or PBMC with (FIG. 5A) or without (FIG. 5B) rmIL-12 as described in Example and in FIG. 3. Peptide (1 $\mu$M) peptide was used for pulsing of each APC type. sDC ($5\times10^5$) were used per injection; for splenocytes. either $20\times10^6$ (spleen 1), $2\times10^6$ (spleen 2) or $5\times10^5$ (spleen 3) cells were used; for PBMC, either $2\times10^6$ (PBMC 1), $1\times10^6$ (PBMC 2), or $5\times10^5$ (PBMC 3) cells were used. Two weeks following the last immunization, PBMC were isolated and stimulated in a 6 day MLTC using P198 cells as stimulators. Similar results were obtained using P198.B7-1 cells as stimulators. Lysis from individual mice was assessed against the antigen-positive target P198 and against P511 as a negative target. Unlabeled P511 cells were added as competitor cells to eliminate non-specific activity. Each filled circle represents lytic activity obtained from an individual mouse at the E:T ratio of 30:1. Lysis against P511 was less than 10% at the same E:T ratio.
Figure 5B:
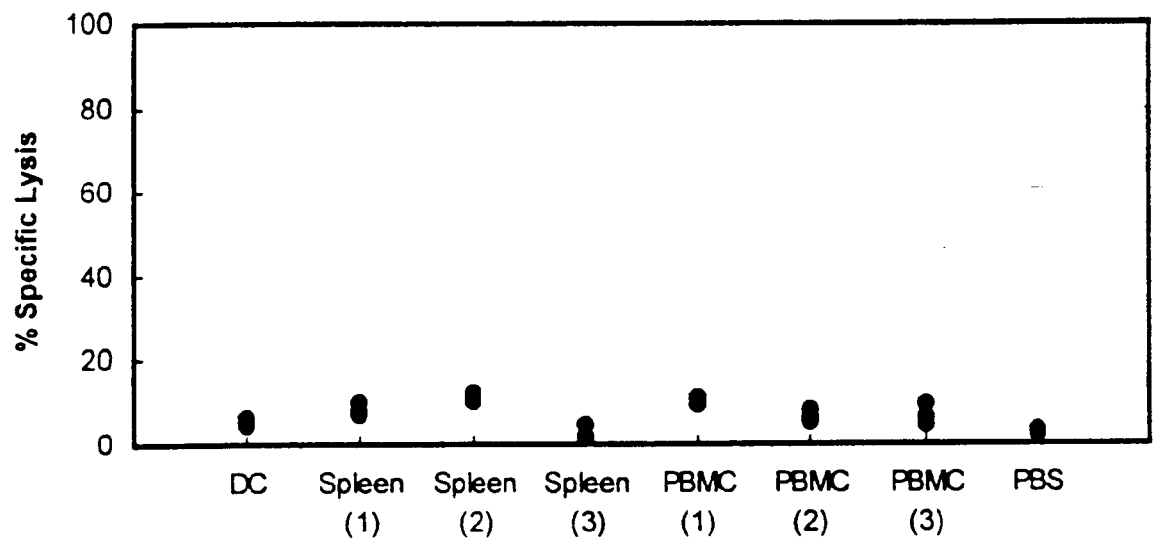

Non-fractionated splenocytes and PBMC were examined first, compared to sDC. In these studies, each APC population was pulsed with an equal concentration of the PI198 peptide (1 μM), but mice were injected with varying numbers of the peptide-loaded APCs. The results in FIG. 5 confirm that three weekly immunizations with pulsed sDC alone failed to induce detectable CTL, whereas the additional administration of rmIL-12 resulted in CTL activity in 100% of mice. Interestingly, immunization with P198 peptide-pulsed total splenocytes or PBMC also successfully induced CTL activity, but only when rmIL-12 was included in the immunization protocol (FIG. 5). However, specific CTL activity was induced only when mice were injected with higher numbers of splenocytes or PBMC (1–20×10⁶) but only in few mice immunized with an equivalent number of cells to that used in the case of sDC (5×10⁵).

Figure 6:
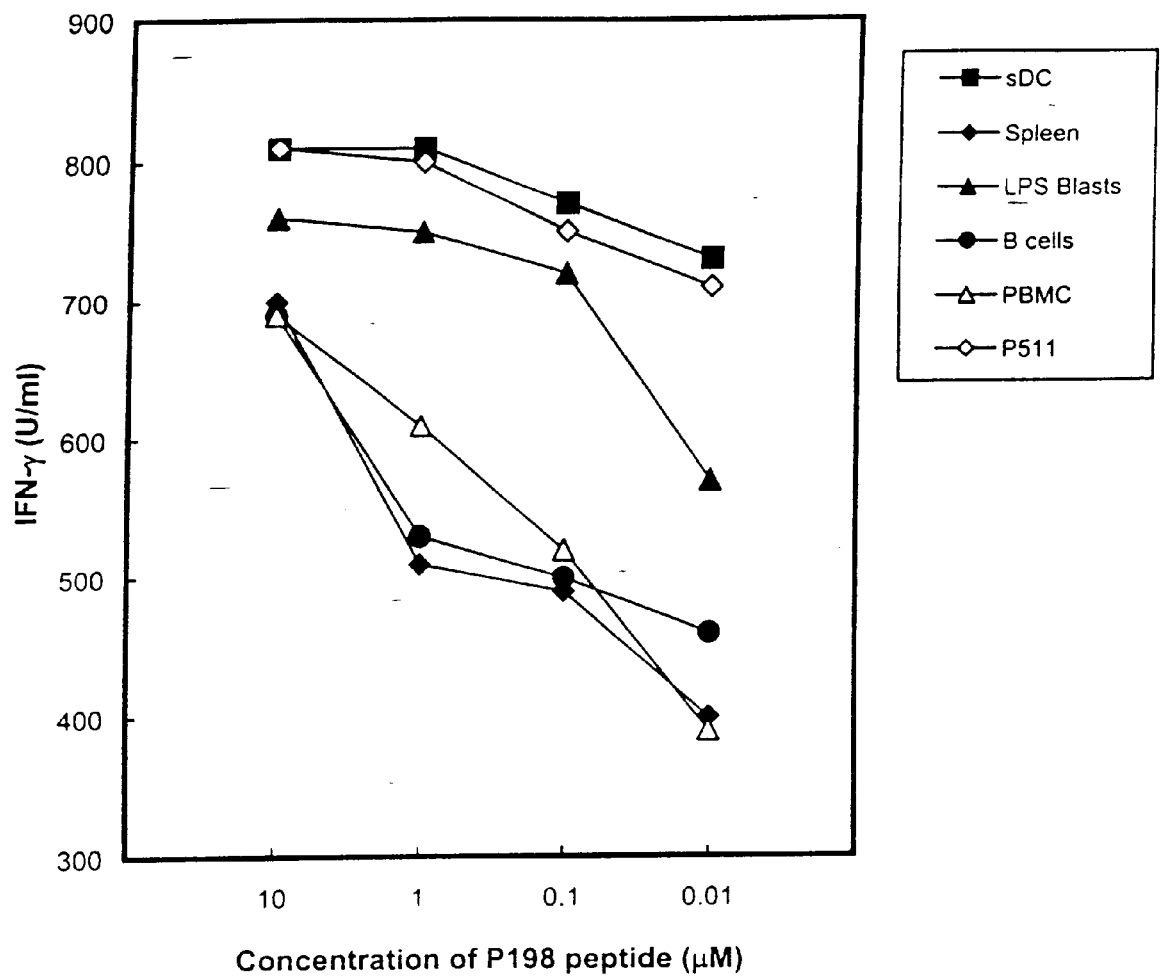
FIG. 6. Production of IFN-γ by CTL P198.6 clone stimulated with different types of APCs pulsed with the P198 peptide. DBA-derived sDC, unfractionated splenocytes, resting B cells, LPS-activated spleen cells, PBMC, or P511 tumor cells were pulsed with varying concentrations of the P198 peptide, washed, then co-cultured with the CTL P198.6 clone for 48 hours. The IFN-γ content of the supernatants was evaluated using a specific ELISA. Production of IFN-γ by the CTL P198.6 in the absence of any APC was less than 20 U/ml, and the IFN-γ production of the same CTL clone cultured in the presence of irradiated P198 tumor cells was approximately 800 U/ml.

It was conceivable that the bulk splenocytes and PBMC were quantitatively less effective than sDC because they bound peptide less well or were otherwise inferior at interacting with T cells, or because they contained among them small numbers of DC that were actually doing the T cell priming. To begin to address these points, the ability of these various APCs pulsed with P198 peptide to stimulate cytokine release by the specific anti-P198 CTL clone in vitro was examined. In addition, splenic B cells were purified to eliminate the majority of contaminating DC, and LPS blasts were compared as well. The same number (1×10⁴) of each APC type was pulsed with increasing concentrations of P198 peptide, irradiated and washed, and cultured with the CTL clone P198.6. IFN-γ content was tested after 48 hours in the supernatants. As shown in FIG. 6, each APC type was capable of stimulating the CTL clone P198.6. However, it was clear that a higher peptide concentration was needed when using splenocytes, PBMC or resting B cells compared to sDC in order to obtain a comparable response. These results show that sDC as well as other types of APC were able to present the tumor peptide P198 to the specific P198.6 CTL clone, but that the non-DC APC were less effective on a per-cell basis at interacting with the T cells. This deficiency could be overcome by using a greater peptide concentration with the non-DC APC.

Figure 7:
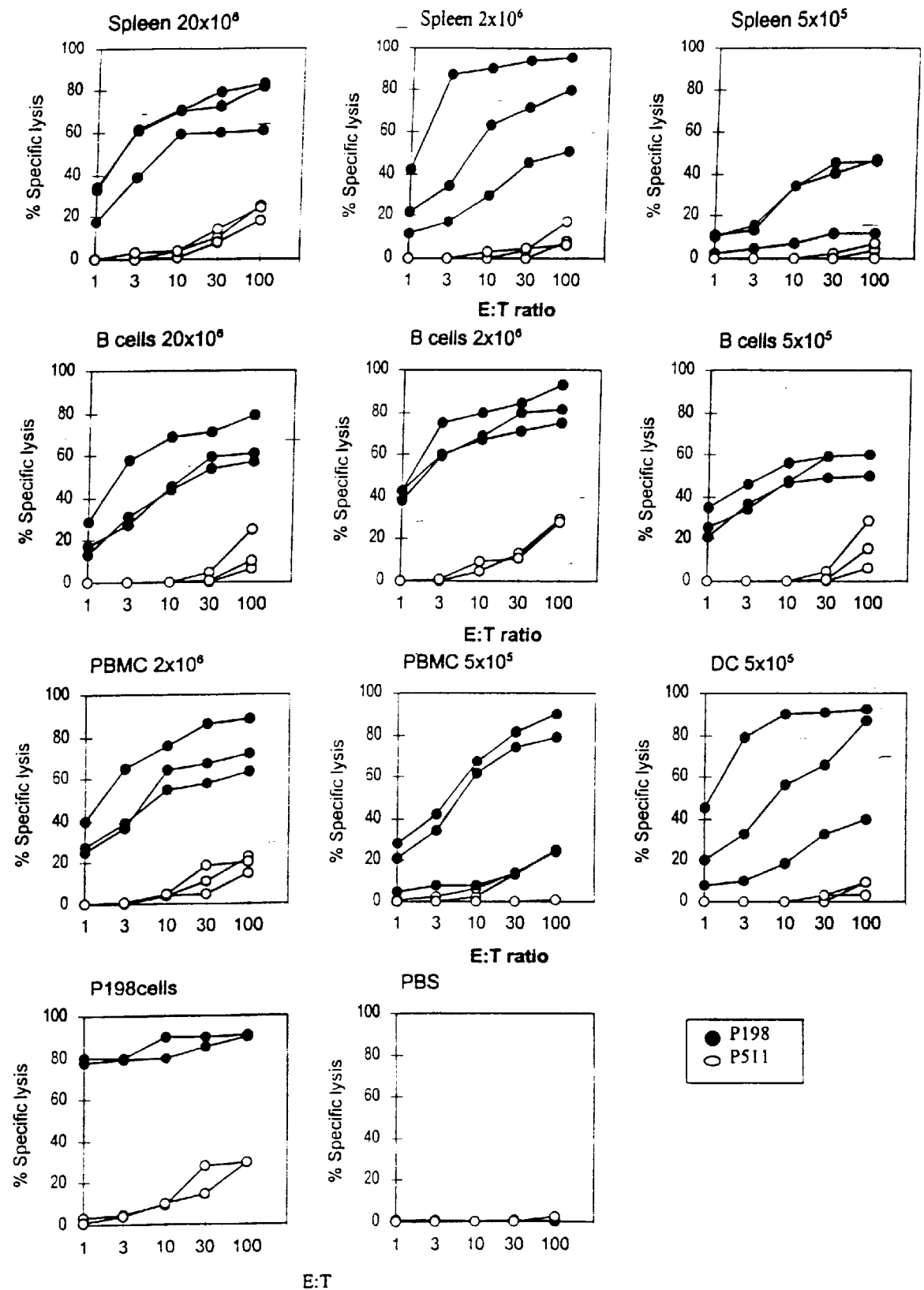
FIG. 7. Lysis of P198 target cells by CTL from mice immunized with P198-peptide-pulsed APCs plus rmIL-12. DBA/2 mice were injected weekly for 3 weeks with P198 peptide-pulsed sDC ($5\times10^5$), B cells ($0.5–20\times10^6$), spleen cells ($0.5–20\times10^6$), or PBMC ($0.5–2\times10^6$) along with rmEL-12 as described previously. The sDC were pulsed with 1 μM peptide, whereas the other cells were pulsed with 10 μM peptide. Two weeks following the last immunization, PBMC were isolated and stimulated in vitro for 7 days in the presence of irradiated P198 cells. Lytic activity against $^{51}$Cr-labeled P198 cells (solid circles) and P511 cells (open circles) was then assessed.
Figure 8A:
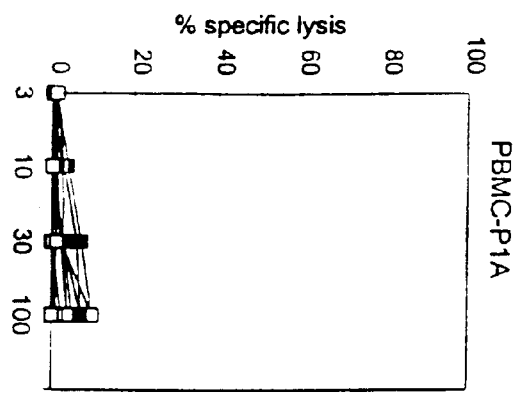
FIG. 8A–8D. CTL activity obtained from individual DBA/2 mice immunized with PIA peptide-pulsed PBMC with or without rmIL-12. Naive DBA/2 mice (5 per group) were immunized weekly for 3 weeks with $2\times10^6$ irradiated PBMC pulsed with P1A peptide (10 μM) alone (FIG. 8A) or in combination with rmIL-12 (FIG. 8B). Control mice were injected with non-pulsed PBMC plus rmIL-12 (FIG. 8C) or with DPBS (FIG. 8D). Two weeks following the last immunization, PBMC were isolated and stimulated with LI210.P1A.B7-1 cells, and cytolytic activity was assessed at day 6 against P511 and P1204 target cells.
Figure 8B:
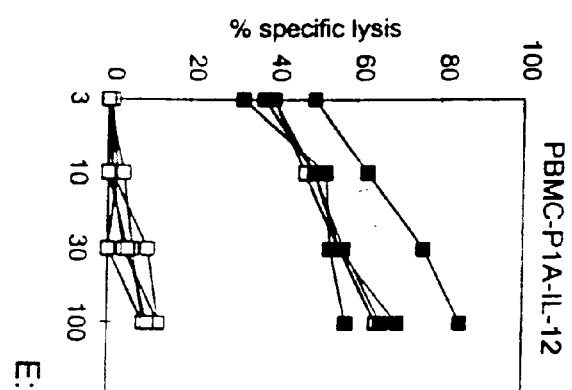
Figure 8C:
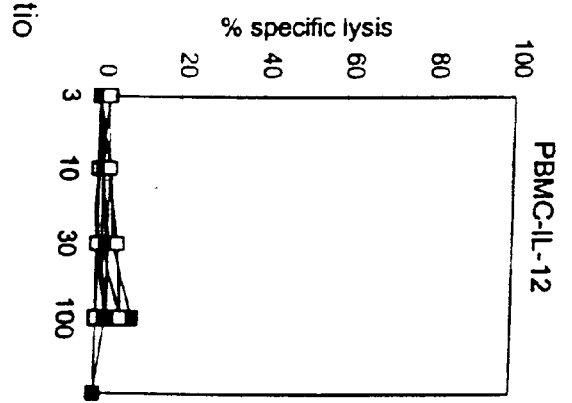
Figure 8D:
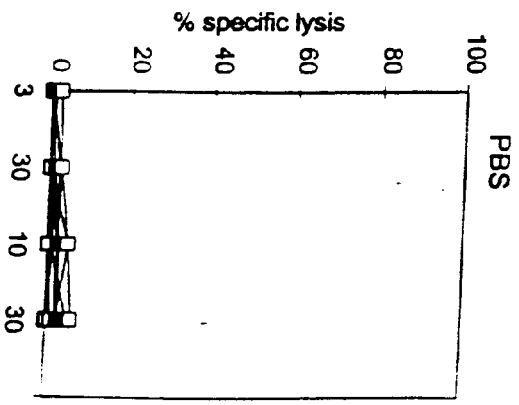

The effect of using a higher peptide concentration was then explored during immunization in vivo. Mice were immunized with various numbers of P198 peptide-pulsed B cells, splenocytes, or PBMC along with rmEL-12 on days 0, 1, and 2 as before. However, the non-DC APC were loaded with 10 μM peptide whereas the sDC were loaded with 1 μM peptide prior to immunization. As shown in FIG. 7, comparable levels of CTL activity were induced on a per-cell basis when 10-fold greater peptide concentration was used for the pulsing of non-DC APC populations. The fact that purified B cells effectively immunized argues against the possibility that contaminating DC in the APC populations are responsible for the actual priming. Thus, the relative inefficiency of non-DC as APC to immunize in vivo could be overcome either by increasing the number of pulsed cells or by increasing the concentration of the peptide used for pulsing.

Immunization with PBMC pulsed with a P815-A peptide and IL-12 induces protection against living tumor challenge. The ease by which PBMC can be obtained from human patients makes peptide-loaded PBMC plus IL-12 an attractive approach for clinical application. This potential prompted investigation of whether the generation of specific CTL induced by administration of PBMC pulsed with a tumor peptide plus IL-12 correlates also with the capability to reject challenge with a tumor expressing the epitope used for immunization. In order to analyze this possibility, another P815-associated peptide needed to be used since the cell line expressing the P198 epitope in association $K^d$ is a tum-regressor cell line that is naturally rejected in vivo. The nonamer P815A peptide which corresponds to residues 35–43 of the protein P1A presented by $L^d$ (Lehe el al., 1992) was chosen. In fact, P1A is a good model antigen because the P1A gene, like the MAGE gene family in human tumors (De Plaen et al, 1994), is expressed in several murine mastocytoma cell lines, but is silent in adult tissues except for the testis and placenta (Uyttenhove et al, 1997).

As for P198, sDC, total spleen cells, B cells, or PBMC loaded in vitro with the P815A peptide all were able to present correctly this epitope to a specific anti-P815 CTL (designated P1:5) in vitro. Using the same pulsing and immunization scheme that had been effective for P198, PBMC were loaded with P815A peptide (10 μM) and were administered in vivo along with rmIL-12. Control mice received PBMC incubated with no peptide plus IL-12, PBMC plus peptide but without IL-12, or just the vehicle PBS. Two weeks after the last immunization, all the mice were tested for specific anti-P815A CTL activity in the peripheral blood following a 6 day MLTC. Also in this case the 2 different stimulator cells were used for the in vitro MLTC. The first was the syngeneic tumor L1210 transfected to express the gene P1A (L1210.P1A), and the second was L1210.P1A.B71 cell line, a double transfectant expressing P1A and B7-1. Lytic activity was tested against P815, which expresses antigen P815A, and on the negative control cell line P1204, a P815 variant that had lost the expression of gene P1A (Uyttenhove et al., 1983). To eliminate non-specific lytic activity, assays were performed in the presence of a 50-fold excess of P1204 cold (i.e. nonradioactive) competitor target cells. As shown in FIG. 8, effective CTL induction was obtained in 100% of mice only when the mice were immunized with peptide-loaded PBMC along with rmIL-12. In contrast with what had been seen with the P198 peptide, B7-1 expression on the stimulator cells did in fact increase the sensitivity of the MLTC, resulting in greater detectable CTL activity. In addition to PBMC, P1A peptide-pulsed splenocytes or sDC also successfully induced CTL activity in vivo.

Figure 9:
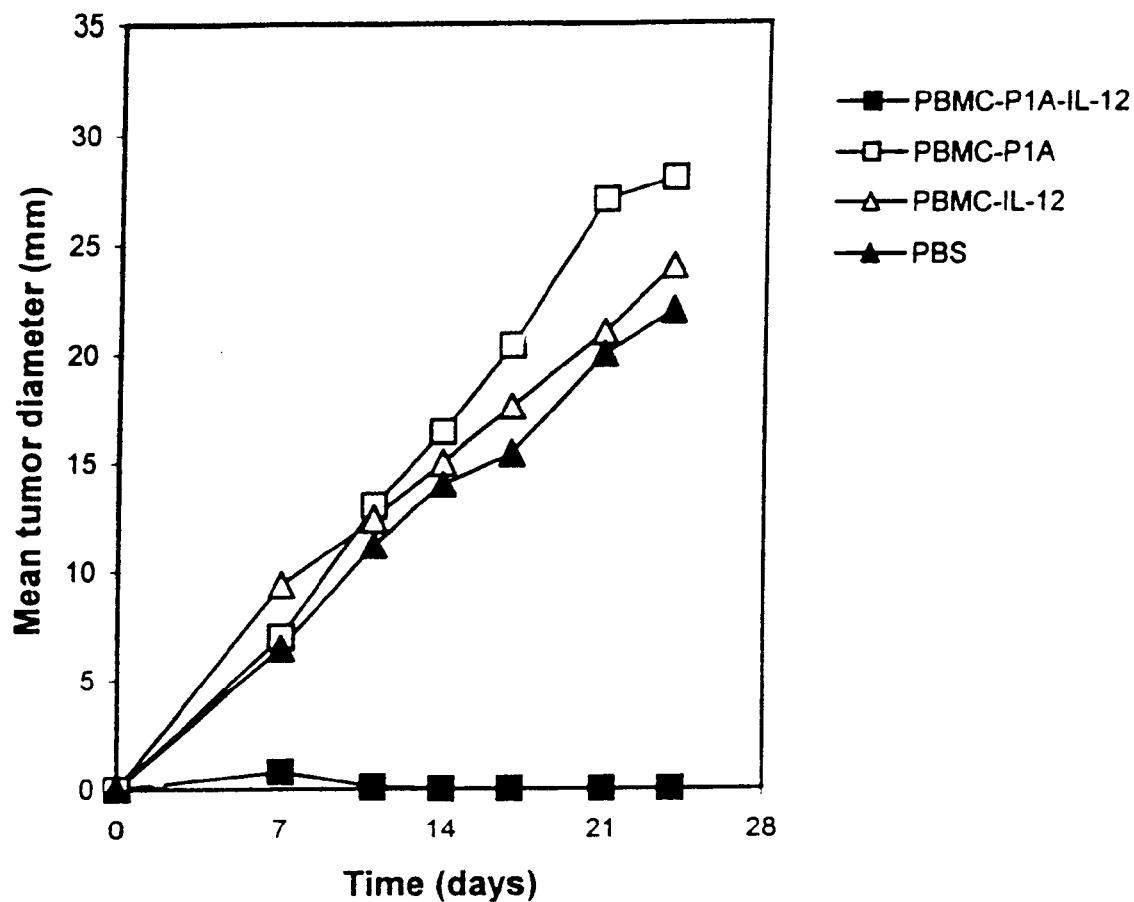
FIG. 9. Protection against living P1.HTR tumor challenge in mice immunized with P1A-loaded PBMC plus rmIL-12. Naive DBA/2 mice (5 per group) were immunized weekly for 3 weeks with DPBS (closed triangles), PBMC plus rmIL-12 (open triangles), PBMC loaded with P1A (open squares) or with PBMC-P1A in combination with rmIL-12 (closed squares) according to the schedule depicted in FIG. 3. Ten days following the CTL assay (shown in FIG. 8), all the mice were challenged s.c. in the left flank with $1\times10^6$ living P1 .HTR tumor cells. Bidimensional measurements were recorded at the indicated times. Similar results were obtained in at least two studies.

As mentioned previously, measuring CTL activity from the peripheral blood allowed the same mice to be challenged with living tumor to assess for protection. Ten days following the CTL assay, treated mice received P1.HTR tumor cells ($1 \times 10^6$) subcutaneously on the flank. P1.HTR is a highly transfectable variant of P815 that expresses the P815A epitope and grows as a solid tumor in vivo, growing progressively in about 90% of naive syngeneic DBA/2 mice (Gajewski et al., 1996). The results in FIG. 9 show that mice immunized with P815A-pulsed PBMC plus rmIL-12 not only acquired specific anti-P815A CTL but also were protected against challenge with a tumor expressing the same antigen. In parallel studies, immunized mice did not reject the P1A-negative variant of P815, P1204, demonstrating antigen specificity. In contrast, mice injected with PBMC loaded with P815A peptide but not given rmIL-12 or with empty PBMC and rmIL-12 were not protected against tumor challenge (FIG. 9). Thus, a good correlation was evident between the ability of peptide-pulsed PBMC plus IL-12 to induce CTL activity and to protect against a tumor challenge. In fact, immunization with peptide-loaded PBMC in the absence of IL-12 failed to induce protective immunity in vivo just as it was unable to facilitate the generation of specific anti-tumor CTL.

EXAMPLE 2

Surrogate Assay for Effective Tumor Antigen-Specific Immunization for Patients with Metastatic Melanoma Tissue culture techniques. The general methods of Cerottini et al. (1974) with some modifications (Glasebrook and Fitch, 1980) are used to culture mouse lymphoid cells. All cell lines are screened periodically for mycoplasma, and precautions are taken to maintain a mycoplasma-free laboratory. The base medium used for murine cells is DMEM, and that for human cells is RPMI.

Isolation of APC subpopulations. Spleens are surgically removed from mice that have been anesthetized and cervically dislocated. Cell suspensions are prepared by homogenization with a ground glass tissue grinder, and connective tissue debris is removed by slow centrifiigation for 30 sec. Dendritic cells are prepared by culturing fresh splendcytes on tissue culture dishes for 1.5 h, rinsing away the non-adherent cells, and culturing overnight at 37° C. in culture medium. The non-adherent cells are isolated by gentle rinsing; these are predominantly dendritic cells (Inaba et al., 1987). B cells are purified by removal of adherent cells, depletion of T cells with anti-Thy-1 mAb and complement, and Percoll density centrifugation (Stack et al, 1994).

In vivo tumor studies in mice. For immunizations, 2–10× $10^5$ peptide-pulsed APC of various sorts are prepared in a volume of 50 µl DPBS. They are injected via a 1 cc syringe through a 23 gauge needle. Locations to inject include subcutaneously in the hind footpads or flanks, or intravenously through the tail vein. Inoculation with living tumor cells is usually performed subcutaneously on the flank. For P1.HTR and the other P815 variants, $5 \times 10^5$ cells has been used to generate tumor growth in the majority of mice. Tumor size is measured in the largest and shortest dimensions, and a mean is calculated for each data point. Every effort is made to minimize discomfort to the animals.

Cytolysis assay. Cytolysis is measured using a $^{51}$Cr-release assay. Effector cells are collected, counted, and resuspended at a concentration of $2 \times 10^6$/ml. Targets to be assayed are loaded with $Na_2^{51}CrO_4$, washed, and resuspended at $2 \times 10^5$/ml. Serial dilutions of effector cells are made in V-bottom microtiter plates in a volume of 100 µl, and an equal volume of labeled targets is added. For cold target inhibition, a 20- to 50-fold excess of unlabeled targets is added per well. The plate is briefly centrifuged, incubated at 37° C. for 4–5 hours, and $^{51}$Cr-release is measured from supernatants using a 96-well plate gamma counter. Spontaneous release is measured from target cells alone, and maximal release is measured from target cells lysed with Triton X-100. Percent maximal $^{51}$Cr-release is calculated as described (Lancki et al., 1987).

Cytokine assays by ELISA. Several cytokines are assayed by standard ELISA techniques. The principal cytokines examined are IFN-γ, TNF-α, IL-2, and IL-4. Briefly, 96-well plates are coated with the relevant anti-cytokine mAb, washed, and blocked with a protein-containing buffer to prevent non-specific binding. They are washed, and serial dilutions of the test supernatants or a standard (usually a recombinant version of the cytokine) are prepared in duplicate. After incubating and washing again, a second anti-cytokine Ab is added and the plates are incubated. After washing, the plates are developed using a horseradish peroxidase-coupled third Ab followed by a substrate that generates a colored product. The plates are read on an ELISA reader, and the half-maximal dilutions are compared to the standard and converted to pg/ml or U/ml.

PCR™ for MAGE-3 or Melan-A gene expression. PCR™ analysis of tumor samples for expression of the MAGE-3 or Melan-A genes are performed as part of the clinical immunization protocol using techniques well known to those of skill in the art. Briefly, messenger RNA (mRNA) from frozen or fresh tumor samples is isolated using the guanidine/cesium chloride method. cDNA are synthesized using oligo(dT)$_{15}$ as a primer according to standard methods.

RT-PCR™ analysis of tumor samples for expression of the MAGE-3 and Melan-A genes is performed using the following oligonucleotides and program. The oligonucleotide primers to be used for MAGE-3 PCR™ are:

Sense: 5'-TGGAGGACCAGAGGCCCCC-3' (SEQ IS NO:3).

Antisense: 5'-GGACGATTATCAGGAGGCCTGC-3' (SEQ IS NO:4).

The oligonucleotide primers to be used for Melan-A PCR™ are:

Sense: 5'-CTGACCCTACAAGATGCCAAGAG-3' (SEQ IS NO:5).

Antisense: 5'-ATCATGCATTOCAACATTTATTGATGG-3' (SEQ IS NO:6).

The oligonucleotide primers to be used for β-actin control are:

Sense: 5'-GGCATCGTGATGGACTCCG-3' (SEQ IS NO:7).

Antisense: 5'-GCTGGAAGGTGGACAGCGA-3' (SEQ IS NO:8).

PCR™ is performed for 40 cycles at an annealing temperature of 58° C. PCR™ products are visualized using 1.5% EtBr-stained agarose gels. The expected size of the PCR™ products are 725 bp for MAGE-3, 605 bp for Melan-A, and 615 bp for β-actin. No attempt at quantitation is made.

For cases in which very small amounts of tissue are available (e. g. a CT-guided core biopsy), a second round of nested PCRT is performed with a set of primers internal to the first as described in Example 6.

HLA typing. HLA typing for class I MHC only is performed by using standard methods well known to the skilled artisan.

Isolation of human PBMC. Peripheral blood (approximately 100–150 cc) is collected with heparin from each patient prior to each scheduled immunization, and three weeks after the final immunization. The cells are diluted 2:1 in DPBS, placed over a Ficoll-Hypaque or Lymphoprep gradient, and centrifuged at 3000 rpm for 15 minutes at room temperature. The mononuclear cells are collected from the interface, washed with DPBS, and counted. They then are prepared for the vaccine or for cryopreservation as indicated in the clinical protocol.

Cryopreservation of cells. Approximately $10 \times 10^6$ cells are resuspended in 1 ml of medium consisting of 50% fetal bovine serum, 10% DMSO, and 45% either DMEM (for murine cells ) or RPMI (for human cells). The labeled vials are placed in an insulated chamber overnight at <70° C., and transferred to liquid nitrogen for long-term storage. For measurement of MAGE-3-specific CTL activity from the melanoma patients being treated, a single vial of stored cells is thawed and the cells are washed and counted. They are then stimulated and expanded in vitro as indicated in the protocol.

Statistical methods. Descriptive statistics are generated to describe the frequency of observed toxicities and immunologic changes induced by the treatment within each of the small dose cohorts. At the determined phase II dose, however, more formal statistical inferences should be possible. The immunologic responses observed before treatment are compared to those following each immunization using paired t-tests. Varying baseline levels are expected between patients, so a log transformation is employed and 95% confidence intervals are generated for the mean ratio between post-treatment and baseline responses. In addition, data are analyzed from the baseline and each of the post-immunization studies using repeated measures analysis of variance to determine the pattern in the response over multiple treatment cycles.

EXAMPLE 3

Immunization of Humans with Peptide-pulsed PBMC plus IL-12

Methods

This example outlines a general protocol for a non-randomized study of immunization with Mage3 or MelanA peptide-pulsed autologous PBMC plus escalating doses of rhIL-12 in selected patients with metastatic melanoma. The protocol consists of immunization with a mixture containing the patient's own blood cells with a peptide of Mage3 or MelanA, depending on which the patient's own cancer cells are producing. Varying doses of recombinant human interleukin-12 (rhIL-12) are also given. Mage3 and MelanA are proteins produced by the majority of melanoma tumors examined. Cancer cells producing one of these proteins, break it down into smaller peptide fragments which stick to the surface of the cell via HLA antigens. Cytotoxic T lymphocytes (CTL) can then recognize the peptide/HLA combination and kill the tumor cells that express it. Therefore, the design of the protocol in this example is to stimulate the body to produce CTL that will specifically kill tumor cells.

Treatment: Patient therapy is initially consists of 3 cycles. Each treatment cycle is 21 days in length, consisting of immunization (peptide-pulsed PBMC) and rhIL-12 injection on the first day, rhIL-12 injection on the third and fifth day, and a 16 day rest period. An initial cohort of 3–6 patients receives the MAGE-3- or Melan-A-pulsed PBMC alone. No placebo in place of rhIL-12 is given. If a patient has an objective response or stable disease, therapy may continue for additional sets of 3 cycles.

Duration: Patients may remain on study for up to 1 year.

Number of Patients: Cohorts of 3–6 patients are treated without rhIL-12, and at the 30, 100, and 300 ng/kg/day dose levels of rhIL-12. Up to 10 additional patients are treated at the recommended phase II dose of rhIL-12. Up to 34 patients are enrolled in this study. The number of patients at each dose level is totaled (those receiving MAGE-3 and those receiving Melan-A), and patients are enrolled sequentially irrespective of whether they are receiving MAGE-3 or Melan-A.

Dose Escalation: Dose of rhIL-12 are escalated in cohorts of $\geq 3$ patients unless a dose limiting toxicity (DLT) is encountered. If DLT occurs in one of the first 3 patients at a dose level, then three additional patients are treated at that dose level to determine if the maximally tolerated dose (MTD) has been exceeded. If none of the first three patients at a dose level experience DLT after 2 cycles, then dose escalation may proceed to the next level. The MTD is defined as the dose level at which at least 2 of 3 or 2 of 6 patients experience DLT. The recommended phase II dose is one dose level below the MTD, or the dose that gives optimal immunization as measured by T cell responses, whichever is lower. In the unlikely scenario that a DLT is seen only with one peptide and not the other, then immunization with that peptide is explored further as an independent cohort.

Patient Eligibility

Inclusion criteria comprises:
1. Histologically-confirmed metastatic melanoma.
2. Life expectancy of at least 12 wk.
3. Karnofsky performance status index $\geq 70$.
4. Written informed consent.
5. Adequate hematopoietic, renal, and hepatic function, defined as:

| | |
|---|---|
| Absolute neutrophil count | $\geq 1500/\mu l$ |
| Hemoglobin | $\geq 9$ g/dl |
| Platelet count | $\geq 100,000/\mu l$ |
| Creatinine | $\leq 1.5$ x ULN |
| SGPT | $\leq 2$ x ULN |
| Bilirubin | $\leq 1.5$ x ULN |
| Calcium | $\leq 11$ mg/dl |

6. HLA typing: patient must express HLA-A2.
7. MAGE-3 or Melan-A expression: tumor must express MAGE-3 or Melan-A by RT-PCR™ analysis.

Exclusion criteria comprises:
1. Significant cardiovascular disease, or cardiac arrhythmia requiring medical intervention.

2. Pregnant or nursing women.
3. Biological therapy in the 4 wk prior to the start of dosing,
4. Seropositive for hepatitis B surface antigen. Patient should be tested if clinically indicated.
5. Seropositive for HIV antibody. Patient should be tested if risk factors are identified.
6. Serious concurrent infection.
7. Concurrent systemic corticosteroids (except physiologic replacement doses) or other immunosuppressive drugs (e. g. cyclosporin A).
8. Psychiatric illness that may make compliance to the clinical protocol unmanageable or may compromise the ability of the patient to give informed consent.
9. Clinically significant autoimmune disease.
10. Active gastrointestinal bleeding or uncontrolled peptic ulcer disease.
11. History of inflammatory bowel disease.
12. Untreated brain metastases. Patients with treated brain metastases must be weaned from corticosteroids and be clinically stable prior to enrolling on this study.

Exceptions to eligibility criteria are considered on a case-by-case basis, if in the opinion of the attending physician such exception will not unduly increase risk to the patient. Inasmuch as the toxicity of the peptide-pulsed PBMC without rhIL-12 is expected to be minimal, it is preferred that such exceptional patients be treated in the cohort not receiving rhIL-12.

Test Schedule

| Tests and Procedures | 14 days prior to registration | Day 1 and 7 of each cycle | Follow-up q 8 wk until PROG, then q 8–12 wk |
|---|---|---|---|
| History and exam, tumor meas., Height, Weight, KPS | X | X | X[5] |
| Vital signs | X | X | X |
| WBC, Hgb, Plt | X | X | X |
| Chem 17, Mg, SGPT | X | X | X |
| PT, PTT | X | | |
| EKG | X[1] | | |
| CXR | X[1] | | |
| CT scans[2] | X | | X |
| HLA typing | X[1] | | |
| Tumor biopsy and PCR ™ | X[1] | | |
| DTH for PPD and recall antigens | X[1] | | X[6] |
| HBSAg, HIV (if clinically indicated) | X[1] | | |
| Urine preg. test | X | | |
| Assay for serum cytokines | | X[3] | |
| Assay for cytotoxic T cells | | X[4] | |

[1]May be done up to 28 days prior to registration.
[2]CT scans will be done as necessary for tumor staging and until PD is documented.
[3]Approximately 10 ml of clotted blood will be collected for serum storage.
[4]An aliquot of PBMC prepared on day 1 of each cycle will be cryopreserved for future assessment of CTL.
[5]Follow-up will be life-long.
[6]DTH for PPD and recall antigens will be performed again when therapy is complete.

Drug Information/Study Methods

The MAGE-3 and Melan-A peptides are produced according to GMP standards by Multiple Peptide Systems, San Diego, Calif. The following MAGE-3 peptide (using single letter amino acid designations) is used for patients expressing HLA-A2 and with MAGE-3+ tumors: FLWGPRALV (SEQ ID NO:9) The following Melan-A peptide is used for patients expressing HLA-A2 and with Melan-A+ tumors: AAGIGILTV (SEQ ID NO: 10)

Each peptide is provided in lyophilized vials containing 1 g each. A single vial of MAGE-3 peptide is reconstituted at a concentration of 20 μM in Dulbecco's PBS (DPBS; Gibco/BRL), stored in 5 ml aliquots at −80° C. The Melan-A peptide is reconstituted in DMSO, then diluted in DPBS. This volume is added to an equal volume of autologous PBMC for incubation (peptide-pulsing) at the time of preparing each vaccine.

rhIL-12 is manufactured and provided by the Genetics Institute (Cambridge, Mass.). The rhIL-12 drug product is supplied as a lyophilized powder in 5 ml vials under mild vacuum. Each vial contains 50 μg of rhIL-12. Vials are intended for single use only. Sterile water for injection (WFI) is supplied to reconstitute the product. Bacteriostatic WFI should not be used. The lyophilized rhIL-12 must be stored in a secured refrigerated facility at 2–8° C. The WFI may be stored at room temperature. After reconstitution, doses are stable for 2 h at 2–8° C. Unit doses prepared in a syringe may be kept at room temperature and must be used within 4 h of preparation. Lyophilized rhIL-12 is reconstituted with either 5 or 1 ml of sterile WFI. Reconstitution is complete in approximately 1 minute.

Once all screening and other pre-study tests are completed, the patient is admitted for the first immunization and rhIL-12 injection.

PBMC is prepared according to standard methods. Approximately 100–150 ml of peripheral blood is collected using standard phlebotomy technique, directly into 2–3 60 cc syringes containing 0.6 cc preservative-free heparin. An aliquot of the peripheral blood sample (at least $10 \times 10^6$ cells) is cryopreserved for future assessment of baseline immunologic studies. PBMC is isolated by centrifugation over a Lymphoprep gradient (Gibco/BRL), counted, washed in DPBS, and resuspended in DPBS at a concentration of $40 \times 10^6$ cells/ml. An equal volume of the relevant peptide solution (prepared at 20 μM in DPBS) is added, and the suspension is incubated for 1 h at 37° C. with gentle rocking. The cells are then lethally irradiated (2000 cGy), washed once with DPBS, and resuspended in DPBS at a concentration of $50 \times 10^6$ in 0.5 ml. The suspension of peptide-loaded PBMC is injected subcutaneously using a 1 cc syringe and 21 g needle, divided evenly into 2 sites. The preferred sites of injection are near draining lymph node locations but not near a tumor mass. Examples of appropriate sites would be the proximal thigh, the upper arm, or the lower abdominal wall. tumor mass. Examples of appropriate sites would be the proximal thigh, the upper arm, or the lower abdominal wall.

rhIL-12 at the dose level assigned to the patient is injected subcutaneously using a 3 cc syringe and 25 g needle as soon as possible after pulsed PBMC inoculation, immediately adjacent to 1 of the 2 immunization sites. If the patient is to receive the vaccination alone without rhIL-12, then no placebo injection is given.

The appearance of each injection site is recorded just before, 1 h after, and 24 h after immunization. In some instances, photographs are taken with a metric ruler in view to document inflammation.

Blood samples (10 cc in a red top Vaccutainer tube) are taken just before, then 12 h, 24 h, and 6 days after immunization. Serum are isolated and stored at −20° C. for subsequent measurement of cytokine levels.

rhIL-12 (if assigned to the patient) is injected subcutaneously in approximately the same location as the first injection on days 3 and 5 as an outpatient.

The entire immunization scheme is repeated every 21 days. One course will consist of 3 cycles. Injections of peptide-pulsed PBMC and IL-12 for subsequent cycles should be made in approximately the same sites as for the first cycle, unless local signs of inflammation prohibit.

Assays will be performed to measure peptide-specific CTL activity and cytokine levels once a practical number of samples have been collected.

Treatment Modification Based on Toxicity

The National Cancer Institute Common Toxicity Criteria Scale are used to grade toxicities. Dose-limiting toxicities is defined as Grade 3 or greater, with the following modifications:

| Toxicity | Dose Reduction |
| --- | --- |
| 1. Grade 3 elevation of SGOT, SGPT, or alk phos | Hold 1 wk; if return to eligibility level then continue at same dose; if 1–3 wk to return to eligibility level, then decrease 1 dose level; if no return to eligibility level in 3 wk then withdraw. |
| 2. Grade 4 neutropenia or thrombocytopenia | See item 1 |
| 3. Grade 3 nausea/vomiting | None |
| 4. Grade 3 hyperglycemia | None |
| 5. Grade 3 fever without infection | None |
| 6. Grade 2 or greater hemorrhage | Dose-limiting (withdraw from study) |
| 7. Grade 2 or greater neurotoxicity | Dose-limiting (withdraw) |
| 8. Capillary leak syndrome (At least 1 of the following): acute weight gain > 10% orthostatic hypotension on at least 2 occasions new pleural effusions drop in blood pressure requiring pressors without obvious cause pulmonary edema without obvious cause | Dose-limiting (withdraw) |

Two treatment interruptions are allowed. If a patient requires a third interruption for toxicity, or if any toxicity does not return to eligibility criteria within 3 wk, then the patient is removed from the study. Dose reduction for the first dose level is allowed, and consists of immunization with peptide-pulsed autologous PBMC alone.

Toxicities greater than grade 3 or satisfying numbers 6, 7, or 8 from the above table are reported as adverse experiences to the FDA and to the Genetics Institute.

In the unlikely circumstance that unusual or dose-limiting toxicities are observed with only the MAGE-3 or the Melan-A peptide, then treatment with that peptide is explored as an independent cohort.

Ancillary Treatment

Symptomatic care may be given as required with medications such as antiemetics and analgesics. However, administration of corticosteroids requires that the patient be removed from the study.

Toxicity Monitoring

Patients are monitored and questioned at every visit (see test schedule) regarding the occurrence and nature of any adverse experiences. An event is defined as any change in the physiologic or psychologic state other than the primary condition that qualifies the patient for the study.

Treatment Evaluation

Patients are evaluated at least every 2 wk (usually day 1 and day 7 of a cycle) while receiving treatment, every 8 wk until there is evidence of tumor progression, then at 8–12 wk intervals so long as the patient is able to return. Patients are observed for 1 h after each rhIL-12 injection to monitor for immediate toxicity.

Evaluation of tumor regression is a secondary endpoint in this study. Tumor masses are characterized carefully with bidimensional measurements.

Criteria for a Partial Response (PR): 50% reduction in the sum of the product of the largest perpendicular diameters of the indicator lesions identified prior to therapy.

Criteria for a Complete Response (CR): total disappearance of all evidence of tumor without appearance of new lesions.

Criteria for Progressive Disease (PD): appearance of new lesions; and/or fifty percent increase in the sum of the product of the largest perpendicular diameters of the indicator lesions. This cutoff has been chosen because initial increases in tumor size followed by tumor shrinkage have been observed in the first MAGE-3 peptide immunization experience; and/or reappearance of any tumor.

Criteria for Stable Disease (SD): Failure to meet the criteria for a Partial Response, Complete Response, or Progressive Disease.

Treatment/Follow-Up Decision at Evaluation of Patient

Patients meeting the criteria for a PR or SD may be retreated for additional courses of 3 cycles. Patients with a CR may be treated with I additional course of 3 cycles and then treatment ceases.

Molecular/Immunologic Studies

HLA typing is performed using standard methods.

Serum levels of IFN-$\gamma$ and TNF-$\alpha$ are assessed by standard ELISA technique.

The presence of circulating MAGE-3- or Melan-A-specific CTL is analyzed. Briefly, $CD8^+$ PBL are isolated using magnetic beads. The $CD8^-$ population is pulsed with the relevant MAGE-3 or Melan-A peptide, irradiated (2000 cGy), and added as stimulator cells along with IL-2. After 1 wk the responding cells are restimulated again in the same fashion. After another wk, cytolytic activity is measured by chromium-release against a peptide-pulsed B cell line expressing HLA-A2 (T2 cells). Negative controls include non-pulsed T2 cells and the NK-sensitive target K562. Cold competition may be performed with unlabeled K562 cells to eliminate non-specific NK activity.

Statistical Considerations

Descriptive statistics are generated to describe the frequency of observed toxicities and immunologic changes induced by each of the small dose cohorts. At the determined phase II dose, there are sufficient numbers of patients (13–16) studied to allow more formal statistical inferences to be made. Immunologic responses before treatment are compared to those following each immunization using paired t-tests. Varying baselines are expected between patients, so a log transformation is employed and 95% confidence intervals generated for the mean ratio between post-treatment and baseline responses. In addition, the baseline values and each of the post-immunization results are analyzed using repeated measures analysis of variance to determine the pattern of response over multiple treatment cycles.

Pathology Considerations

Patients entering this trial already have histologically-confirmed malignant melanoma. Biopsy of tumor is a required part of this protocol in order to examine expression of the MAGE-3 or Melan-A genes by RT-PCR™. Standard histology are performed to verify the pathologic diagnosis of the specimen.

EXAMPLE 4

Outline of a Human Vaccination Study

This example provides results for patients immunized with PBMC incubated with Mage3 peptide or MelanA peptide plus assigned doses of rhIL-12 ranging from 0–100 ng/kg. Patients were treated with peptide-pulsed PBMC alone, using either Mage3 or MelanA peptide as indicated, or with rhIL-12 administered subcutaneously near the immunization site. Following immunization, assays for peptide specific CTL activity and cytokine production, in particular IFN-γ were conducted. Data for clinical responses are also presented. Abbreviations, definitions and methods have been previously set forth in Example 3.

Patient Eligibility:

General inclusion criteria have been set for in Example 3. Additional criteria are as follows:

1. KPS 0–1, intact organ function to receive rhIL-12, HLA-A2-positive; multiple prior therapies allowed, life expectancy 12 wk.
2. Tumor biopsied or obtained surgically, and expression of Mage3 and MelanA assessed by RT-PCR™. Nested PCR™ done for small biopsy material. Only antigen-expressing patients allowed. Priority given to Mage3.

Vaccination Preparation

For each vaccination, 100 cc heparinized blood was obtained and PBMC isolated by Lymphoprep centrifugation. A portion of cells was set aside and separated into CD8+ and CD8-fractions for cryopreservation.

PBMC were incubated with Mage3 peptide (10 μM) or MelanA peptide (50 μM) in DPBS for 1 h at 37° C. Peptide concentrations were chosen based on lowest optimal dose for stabilization of HLA-A2 expression on T2 cells.

Pulsed PBMC were irradiated (2000 rad), centrifuged, and resuspended in 2 cc DPBS for injection.

Injection of pulsed PBMC was performed subcutaneously, divided between 2 sites, either in upper arms or proximal legs.

rhIL-12, at the assigned dose level (ng/kg), was injected subcutaneously near one of the two vaccine sites.

The entire procedure was repeated every 3 weeks, with clinical reevaluation every 3 cycles.

Analysis

T cell functional analysis was performed in batch fashion, with all samples from a given patient thawed and restimulated in vitro simultaneously.

In vitro expansion of CD8+ T cells for testing was performed using minimal activation conditions: peptide-pulsed CD8-negative cells as APCs, only 10 U/ml rIL-2 added on day 2 of each stimulation, with one 6-day stimulation followed by a second 4–5 day stimulation.

When possible for progressing patients, a follow-up biopsy was obtained to investigate for growth of antigen-negative tumor cells.

A summary of the vaccine trial are presented as follows:

SUMMARY OF MAGE3/MELANA VACCINE TRIAL

| Patient | IL-12 Dose | Antigen | Evidence Immunized? | Clinical Outcome | Comments |
|---|---|---|---|---|---|
| 1. AB | 0 | Mage3 | No | SD | |
| 2. DP | 0 | Mage3 | No | PD | PR with IL2 |
| 3. LC | 0 | MelanA | Yes | PR | Congenital ITP (plts ≈ OK) |
| 4. RD | 30 | Mage3 | Yes | MR | |
| 5. RH | 30 | MelanA | Yes | PD (mixed) | Documented antigen-loss |
| 6. JH | 30 | Mage3 | Yes | PD | PD in CNS |
| 7. GC | 100 | Mage3 | | PD (mixed) | Documented antigen-loss |
| 8. PC | 100 | Mage3 | | PD (mixed) | |
| 9. KS | 100 | MelanA | | PD | PD in CNS |

Results

Vaccination of melanoma patients with refractory metastatic disease was demonstrated using tumor antigen peptide-pulsed autologous PBMC plus rhIL-12. This approach is faster and easier than dendritic cell expansion.

Figure 12:
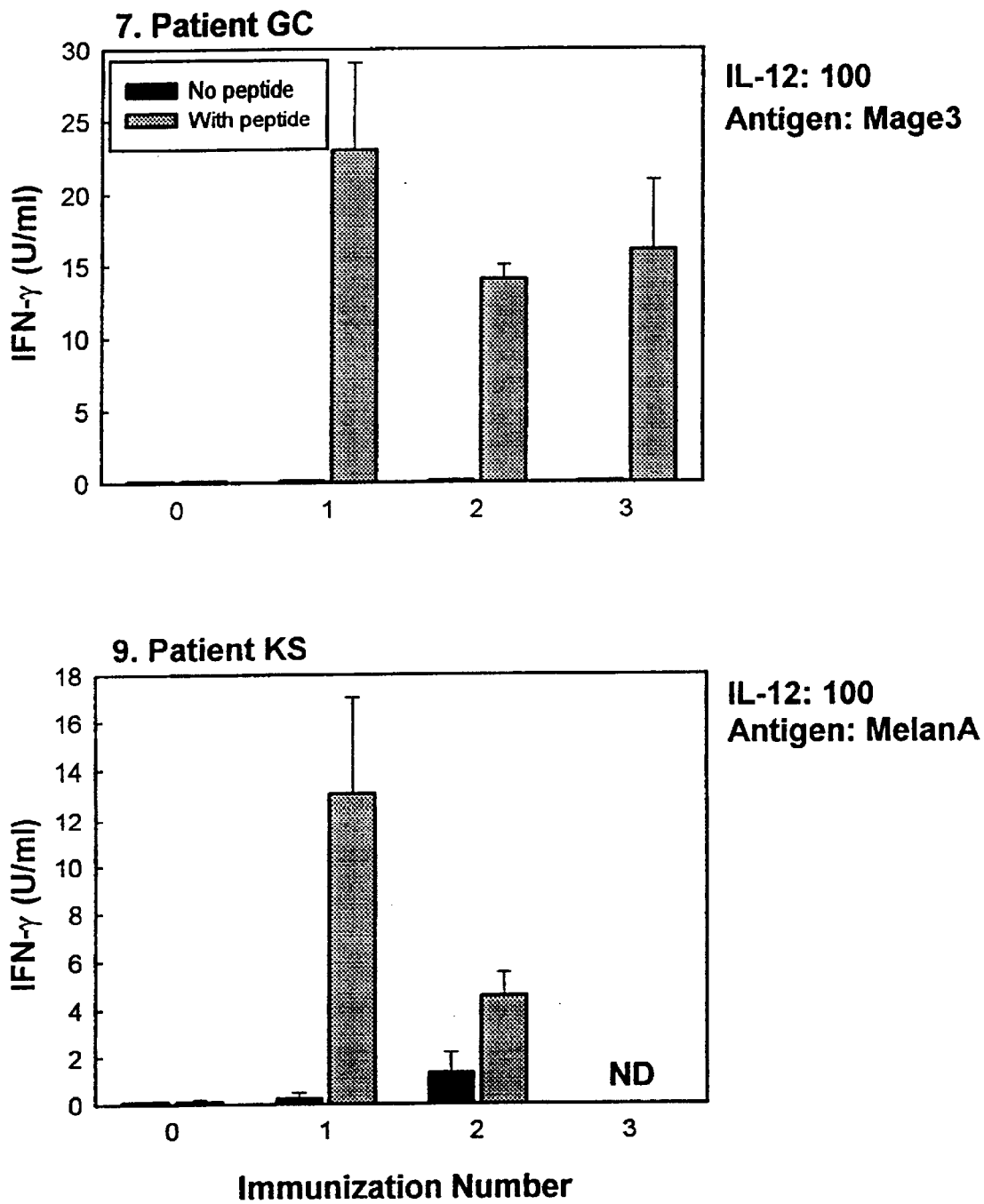
FIG. 12. Vaccination of melanoma patients with refractory metastatic disease was demonstrated using tumor antigen peptide-pulsed autologous PBMC with 30 ng/kg rhEL-12. Generation of peptide-specific, IFN-γ-producing $CD8^+$ T cells was detected after 1 to 3 immunizations with Mage3 (10 μm) or MelanA (50 μm).

Generation of peptide-specific, IFN-γ-producing CD8+ T cells was detected after 1 to 3 immunizations as shown in FIG. 10, FIG. 11. and FIG. 12. MelanA-specific responses appeared to be detected earlier than Mage3-specific responses.

Partial clinical responses and documented selection for antigen-loss tumor variants indicate that T cells primed against each of these antigens can exert an anti-tumor effect.

EXAMPLE 5

Manufacture of GMP grade MPS-38 peptide, Part No. 600038, Lot No. 96020, at MPS Peptide Sequence:

FLWGPRALV (SEQ ID NO:9); MolecularWeight= 1058.3, where a hydroxyl group is attached to the valine at the carboxyl end.

Synthesis of the Peptide on Resin (MD-14 Rev. 5):

The procedure used for the synthesis is the general procedure described in the original paper of Merrifield (1963) with minor modifications. Synthesis was performed in a 1000 mL reaction vessel equipped with a fritted funnel at the bottom for easy solvent wash and filtration of the solid support. Synthesis was started with 30 grams (batch size) of Boc-L-Valine Merrifield resin, substitution 1.04 meq/g. Boc chemistry was used throughout the peptide chain assembly. Calculation of all solvent washes, except for the TFA deprotection step, was based on 10 mL/g of starting resin. For the TFA deprotection step, the washes were based on 15 mL/g of starting resin, as a precaution to ensure complete Boc removal. All amino acids were coupled using DIC or DIC/HOBt as the activating agent. Calculations of amino acid, diisopropylcarbodiimide (DIC) and hydroxybenzotriazole (HOBt) were based on 3 fold excess of the substitution and starting quantity of resin used.

Every coupling was monitored by Ninhydrin test twice. Mixing of resin and solvent was achieved by bubbling Nitrogen.

Amino Acid Recoupling (MD-I.IA):

Recoupling was performed with three equivalents of amino acids and DIC for those coupling steps that indicated a positive Ninhydrin test result. These include Phe[1] and Leu[2]. As a precaution due to coupling onto proline, Gly[4] was recoupled.

After complete chain assembly, final Boc removal was performed. The resulting peptide on resin was dried with nitrogen and weighed. The yield was ~68.1 grams, or 104% of theoretical resin weight gain.

Precleavage Formyl Removal (MD-19 Rev. 1):

The formyl protecting group on the tryptophan residue was removed using a 20% piperidine/DMF solution. As a precaution, this step was performed twice to ensure the removal of the protecting group. Final yield of the resin was 61.6 grams corresponding to 92% of theoretical yield.

HF Cleavage and Side-Chain Deprotection of the Peptide (MD-2 Rev. 4):

After the completion of the formyl group removal, 40 grams of the peptide on resin were cleaved from the resin while deprotecting the amino acid side chains with a condensed HF/anisole mixture (175 mL/35 mL). The reaction was conducted at 0° C. for 60 minutes, after which the HF and anisole were evaporated with nitrogen in ~3 hr. The cleaved peptide was washed with three 200 mL portions of ethyl ether to remove any remaining anisole. The peptide was extracted from the resin with three 200 mL portions of 10% aqueous HOAc. The 10% HOAc/peptide solutions were combined, placed in 1200 mL lyophilization flasks and lyophilized for ~17 hours to dryness on a Virtis FM25EL lyophilizer. The yield was 101% of the theoretical value resulting in 20 g of crude peptide.

Additional washes of the cleaved peptide resin with 50% ACN/50% (10%HOAc/H20) solution provided a negligible amount of additional material and appeared of lower quality. The yield from these washes was discarded.

The crude peptide was analyzed by HPLC and the purity was determined to be ~63%. Under the conditions described, the peptide eluted at ~9 min.

| Analysis of the Crude Peptide: | |
|---|---|
| HPLC System: | Beckman Gold, Shimadzu CR4A Integrator |
| Column: | Vydac $C_{18}$ 4.6 mm x 250 mm, $5\mu$, 300 Å |
| Solvent A: | 0.1% TFA/$H_2O$ |
| Solvent B: | 0.1% TFA/ACN |
| Gradient: | 30–60% B in 30 min. |
| Flow rate: | 1.0 mL/min. |
| Data-Wavelength: | 215 nm |

(See FIG. 2 for a representative HPLC chromatogram of the crude product.)

Purification of the Crude Peptide:

The peptide was purified using Reverse Phase High Performance Liquid Chromatography (HIPLC), with CIs resin as the stationary phase. A single step purification using TFA as the buffer resulted in the desired purity. This resulted in the TFA salt of the purified peptide.

TFA Purification (MD-18 Rev. 3):

A total of 1–2 grams were dissolved in 50–100 mL of 10% acetic acid. The solution was loaded on a dedicated preparative column at 80 mL/min.

| Purification Parameters | |
|---|---|
| HPLC System: | Waters Delta Prep |
| Column: | $C_{18}$ 300 Å, $15\mu$ 7.5 x 39 cm (asset tag #000308 |
| Solvent A: | 0.1% TFA/$H_2O$ |
| Solvent B: | ACN |
| Gradient: | 0–18% B in 10 min. (0–20% B in 10 min.) |
| Flow rate: | 18–38% in 60 min. (20–40% in 60 min.) 80 mL/min. |
| Wavelength: | 215 nm |

Gradient parameters in parentheses were used for the initial rims: G0304 and G0305. A slower gradient was later adopted to increase separation of peptide from impurities.

(See FIG. 3 for a representative preparative HPLC chromatogram and peptide elution pattern.)

Ten micoliters of each fraction believed to contain pure peptide were mixed and analyzed by HPLC. Fractions were eliminated or added until the maximum number of fractions show a trace with a single peak of the desired purity.

| Analysis of Collected Fractions by Analytical HPLC | |
|---|---|
| Column: | Vydac $C_{18}$ 4.6 mm x 250 mm, $5\mu$ 100 Å |
| Solvent A: | 0.1% TFA/$H_2O$ |
| Solvent B: | 0.1% TFA/ACN |
| Gradient: | 25–45% B in 20 min. |
| Flow rate: | 1.0 mL/min. |
| Data-Wavelength: | 215 nm |
| Criteria: | Pooled collections ≥ 95% pure |

(See FIG. 4 for a representative analytical HPLC chromatogram of purified peptide TFA salt)

Each lot of purified peptide TFA' salt was individually shell frozen in a 1200 mL Virtis lyophilization flask and lyophilized to dryness on a Virtis FM25EL lyophilizer. Side fractions from purification were not collected.

Pooling of Purified Peptide, TFA Salt (MD-SRev. 2):

A total of 9.8 g of pure peptide, TFA salt was obtained from purification of 20 g of crude peptide, a yield of 49%. All 13 lots were prepared for exchange to the acetate. salt. As an in-process check, samples from each lot were pooled together, 1 mg for every 417 rag, dissolved in 90% HOAc/ Milli Q water at 5 mg/ ML and analyzed by HPLC. The purity of this "mini-pool" was ~99%. Each purification lot was individually dissolved in 10% HOAc/WFI.

Peptide Exchange of Trifuoroacetate to Acetate Salts on Dowex (MD-21 Rev 0):

A total of 9.8 g of peptide was dissolved in –500 mL 10% HOAc/WFI. An approximately 3 fold excess of Dowex 1×2–100 (1-chloride ion exchange rosin) to equivalents of basic sites in the peptide and quantity exchanged was used to achieve the conversion to the acetate salt. A total of 53 g of Dowex was used to pack the column. The Dowex in the column was washed sequentially with WFI, 1 M NaOH/ WFI, WFI, and 25% Acetic Acid/WFI prior to loading the peptide on the dedicated column. The peptide was eluted from the column with 3 column volumes of 10% HOAc/ WFI. The peptide solution was shell frozen in 1200 mL Virtis lyophilization flasks and lyophilized to dryness on a Virtis FM25EL lyophilizer for ~66 hours. The product was weighed and resulted in a yield of 8.2 grams of peptide acetate salt, 91% of theoretical value.

Packaging and Labeling (MD-9 Rev. 2):

The product was packaged in low density polyethylene containers with polypropylene closures, blanketed with argon and sealed with parafilm. Two containers of 1 g were labeled according to RMS 300043 Rev. 0-a. (See Attachment 2 for labeling information).

| HPLC System Suitability: | |
|---|---|
| A solution of 0.3 rag/ml, of MPS-38 in 10% acetic acid was analyzed by HPLC using the following conditions: | |
| Instrument: | Hitachi D-7000 |
| Column: | Vydac $C_{18}$ 4.6 mm x 250 mm, $5\mu$, 300 Å |
| Solvent A: | 0.1% TFA/$H_2O$ |
| Solvent B: | 0.1% TFA/ACN |
| Gradient: | 20–50% B in 30 min. |

-continued

HPLC System Suitability:
A solution of 0.3 rag/ml, of MPS-38 in 10% acetic acid was analyzed by HPLC using the following conditions:

| Flow rate: | 1.0 mL/min. |
| Data-Wavelength: | 215 nm |
| Injection: | 20 µL |

Six replicate injections resulted in an average Peak Area of 10267852 ±8 1840, with an RSD <1.0%. The purity was 99.4%±0.1%. The retention time of the Peptide A, peak was 16.7±0.1 min. The analysis is linear from 0.04 to 0.8 rag/mL. The data are summarized in Attachment 2.

Product Release and Shipping:

The product was released for distribution after the batch records had been reviewed and approved by QC, and the product had been tested and found to meet specifications. The peptide was shipped on dry ice.

Materials

Amino Acids and Resins: N-Boc-L-Valine Merrifield Resin, N-Boc-L-Arginine (tosyl), N-Boc-L-Leucine H20, N-Boc-L-Alanine, N-Boc-Glycine, N-Boc-L-Tryptophan (formyl), N-Boc-Phenylalanine, and N-Boc-L-Proline.

Reagents and Solvents:

| Reagent | Abbreviation | Reagent | Abbreviation |
|---|---|---|---|
| Dichloromethane | DCM | Anisole | |
| Dimethylformamide | DMF | Ethyl Ether | ET$_2$O |
| Trifluoroacetic Acid | TFA | Acetic Acid | HOAc |
| 2-Propanol | IPA | Argon | Ar |
| Diisopropyl-ethylamine | DIEA | Helium | He |
| Diisopropyl-carbodiimide | DIC | Acetonitrile | ACN |
| 1-Hydroxybenzo-triazole Hydrate | HOBt | MilliQ Water | H$_2$O |
| Nitrogen | N$_2$ | Water for Injection | WFI |
| Hydrogen Fluoride | HF | Piperidine | |

EXAMPLE 6

Preparation of MAGE-3/A2 peptide-pulsed Human PBMC for Immunization

Illuminate UV light in the flow hood for 15 min, then turn off. Turn on hood and clean interior with Roccal then with 70% ETOH. Gather reagents and place in hood (Lymphoprep, DPBS, 50 ml tubes, 250 ml tube, 3 cc syringe, 16 g needle, tubes for cell counting, trypan blue, freezing vials, heparin, red disposal bag). Label tubes (one 50 ml tube per 15 ml of blood; typically 6–8 total), freezing vials (2), and a 3 cc syringe with patient ID and date. Wash hands; put on gown and sterile gloves.

Aliquot 10 ml Lymphoprep into each 50 ml tube. Obtain the heparinized peripheral blood sample that has been isolated from the patient, and estimate the volume. Add 1 blood volume of DPBS to a 250 ml tube, and add in 1/100 volume of sterile heparin (10,000 U/ml stock). Transfer the heparinized peripheral blood to the tube containing DPBS, and gently mix. Layer 30–35 ml diluted heparinized blood over the Lymphoprep in each 50 ml tube. Centrifuge 20 min. at 1000 rpm, 20° C. Remove about 80% of upper phase and discard (to eliminate platelets). Centrifuge 20 min at 2500 rpm, 20° C. (setting #5 on Sorvall RT600B). Remove cells from interface, transferring them to 2 new 50 ml tubes.

Bring volume up to 45 ml with DPBS in each tube, and resuspend with pipette. Centrifuge 5 min at 2000 rpm. Aspirate supernatant; resuspend the pellets in 5 ml DPBS total, pooling into one tube. Count cells with trypan blue (40:1 dilution). Expected yield is 1–2×10$^6$ cells per ml of blood. Set aside 20×10$^6$ cells for separation of CD8 cells and freezing, keeping 80–100×10$^6$ cells for the vaccine. Thaw a tube of MAGE-3 or Melan-A peptide (5 ml at 20 µM in DPBS) by heating in 37° incubator. Transfer cells to tube containing peptide and mix with a pipette. Place in 37° incubator for 1 h; mix by inversion at 30 min.

During incubation, prepare CD8 fractionation and freezing of saved cell aliquot. Remove cells from incubator, and irradiate sample 2000 rads (12.8 min). Mix by inversion, centrifuge 5 min at 2000 rpm. Aspirate supernatant; resuspend pellet in 1 ml DPBS. Count cells with trypan blue and record viability.

Remove 50 µl of final cell suspension and of peptide/DPBS solution for sterility test and endotoxin assay. Also take 1 ml each of the DPBS and the Lymphoprep used and transfer into individual culture tubes. Submit these with patient ID to microbiology lab to assess for contamination. Endotoxin assay is performed and results recorded.

Resuspend cell suspension by tapping. Draw up sample into the 3 cc syringe using a 16 g needle; remove needle and cap the syringe. Place syringe into a Ziploc bag labeled with the patient ID. The vaccine is ready for subcutaneous injection, using a ⅝ inch, 23 g needle.

EXAMPLE 7

Analysis of Melanoma Antigens from Solid Tumor Samples Harvesting Tumor Samples

Tumor samples are obtained in the OR, radiology suite, or clinic and placed into sterile isotonic solution (PBS or Isotonic saline) on ice and brought directly to the lab. All the information about the patients (name, MR#, tumor site) is written in the tumor log book.

Processing of the Tumor Samples

Depending on the quantity of tumor available the inventors try to make: guanidine homogenate to extract RNA; freeze some vials in liquid nitrogen and keeping a record of it in the freezer log book; homogenyze some in a solution of Hyaluronidase (85 U/ml) and Collagenase (1 U/ml) in DMEM to grow cell lines and possibly clone. The tumor is left in the hyalurondase/collagenase until as much of the tumor has separated into a cell suspension as possible (usually a few hours are needed). If the tumor is too big it is cut into smaller pieces using sterile instruments and technique, always keeping the tumor sample on ice.

Briefly, to prepare guanidine homogenate (use RNAase free reagents and keep samples on ice as much as possible), weigh the tissue which is to be homogenized in guanidine. Add the guanidine solution directly to the sample. If sample <50 mg, add 0.5 cc of guanidine. If sample >50 mg, add 3.2 cc of guanidine. Homogenize sample, on ice, using the electric homogenizer (powergen 125; Fisher). Use disposable sterile generators for each separate tumor sample. Always clean homogenizer with SDS 1% and ethanol 70% for each sample. Homogenize samples until as much of solid tumor has been homogenized as possible. Centrifuge the homogenate at 3,000 rpm for 10 min at 4° C. Aspirate supernatant which can now be stored at −70° C. for long-term storage.

Briefly for cesium chloride RNA extraction, carefully load the guanidine lysate onto the top of the CsCl solution.

If original sample was <50 mg, then use 0.8 cc ultraclear centrifuge tubes (Beckman). Note that there is 0.5 cc guanidine lysate/.17 cc CsCI. If original sample was >50 mg, then use 5 ml ultraclear centrifuge tubes (Beckman) and use 3.2 cc guanidine/1.1 cc CsCI. Ultracentrifuge at 35,000 rpm for 18 h at 20° C. in SW 50.1 rotor (overnight)—maximal acceleration and no brake. After ultracentrifugation remove most of supernatant by hand pipette (RNA pellets at bottom of tube and is often not visible). Place tubes upside down in an appropriate carrier to drain any remaining liquid. Cut ultracentrifuge tubes ~0.5–1 cm. from bottom depending on the tube size (cut the smaller centrifuge tube shorted and turn the tube upright.

Dissolve the RNA pellet by pipetting RNAase-free water (100 μl) into the cup and transferring to an Eppendorf tube on ice, appropriately labeled. Rinse the cup with an additional 100 μl of RNAase-free water and add it to the Eppendorf tube.

Add 20 μl of sodium acetate 3M (NaAc) and 250 μl of phenol/Chloroform/isoamyl alcohol and vortex. Keep samples on ice as much as possible during this part of the procedure.

Spin tube using fixed angle rotor (12,000 rpm) for 5 min at 4° C. Transfer aqueous phase to new Eppendorf tube and add 250 μl of chloroform. Mix by vortexing. Spin again as above and remove upper aqueous phase to new Eppendorf tube. Add 600 μl of absolute ethanol and mix gently by inverting. Leave at −20° C. for 30 min. Spin now for 15 min. using fixed angle rotor (12,000 rpm) at 4° C. Discard supernatant and add 150 μl of 70% ethanol. Mix by vortexing. Spin again for 5 min using fixed angle rotor (12,000 rpm) at 4° C. Discard supernatant and allow RNA to dry leaving tube open in hood.

Dissolve RNA in 7 μl RNAase-free water by gentle pipetting. Quantitate yield using Invitrogen DNA dipstick method. Add 1 μl RNAasin to each sample. The sample may be stored at −70° C. at this stage.

For removal of contaminating DNA from RNA preparation (using Gibco amplification grade DNAase), add the following to a small microcentrifuge tube on ice: up to 1 μg RNA per μg DNAase to clean-up reaction; 1 μl of 10× DNAase buffer (Gibco); 1 μl DNAase amplification grade (Gibco); and RNAase free water to bring volume up to 10 μl.

Incubate sample at room temperature for 15 min. Add 1 μl of 25 mM EDTA (Gibco) and heat at 65° C. in water bath for 10 min. The sample is ready for cDNA synthesis.

cDNA Synthesis

Use up to 1 μg of RNA per 20 ul reaction, if possible. Make up a master mix in an Eppendorf tube for reverse transcriptase reactions comprising:

a. 1 μl of dNTP (10 mM; Gibco) per 20 μl reaction
b. 4 μl of 5×1$^{st}$ strand buffer (Gibco) per 20 μl reaction
c. 2 μl of DTT (0.1M; Gibco) per 20 μl reaction
d. 1 μl of RNAasin (40 U/ul; Promega) per 20 μl reaction
e. 1 μl of Reverse Transcriptase (200 U/ul; Gibco) per 20 μl reaction In separately labeled Eppendorfs add 1 μl of Oligo dT primer (0.5 ug/μl) and add 10 μl of each RNA sample into the appropriately labeled tube. Add 9 μl of master mix (from above) to each sample. Vortex and place into water bath at 37° C. for 1 h. Add 30 μl of sterile water to each sample after incubation and place in −20° C. freezer in appropriately labeled box.

PCRTh Conditions for Determining Presence of Melanoma Antigens (MAGE 1, MAGE 3, Tyrosinase, and Melan-A)

Make up master mix in Eppendorf for 50 ul reactions by adding:

a. 1 μl of dNTP (10 mM; Gibco) per reaction
b. 5 μl of 10× PCR buffer (Gibco) per reaction
c. 1.5 μl of $MgCl_2$ (50 mM; Gibco) per reaction
d. 0.3 μl of Taq DNA polymerase (Gibco) per reaction Mix up cDNA samples, primers, and master mix as follows:

a. 7.8 μl of master mix
b. 3 μl of cDNA sample
c. 2 μl of each primer (5' and 3'); total of 4 ul
d. 35.2 μl of sterile water Add drop of mineral oil at end. Run PCR™ for all antigenic primers using the same following conditions and 40 cycles:

a. Pre-dwell at 94° C. for 4 min.
b. Then 94° C. for 1 min.
c. Then 58° C. for 2 min.
d. Then 72° C. for 3 min.
e. Extend at 72° C. for 5 min.

Nested PCR™ reactions are done using the same above PCR™ conditions and for 40 cycles. The product from the primary PCR™ reaction is diluted 1:10 by adding 2 μl of the primary PCR™ product to 18 μl of sterile water. 2 μl of this dilution is then used for the nested reaction. Primers are all reconstituted in 1 ml of sterile water on arrival and then diluted to a concentration of about 100 μg/ml prior to use. Primary primer templates are as follows:

B-actin (5' primer) GGCATCGTGATGGACTCCG (SEQ ID NO: 11);

B-actin (3' primer) GCTGGAAGGTGGACAGCGA (SEQ ID NO:12);

MAGE-1 (5' primer) CGGCCGAAGGAACCTGAC-CCAG (SEQ ID NO: 13);

MAGE-1 (3' primer) GCTCCGACCCTCACTGGGT-TGCC (SEQ ID NO:14);

MAGE-3 (5' primer) TGGAGGACCAGAGGCCCCC (SEQ ID NO: 15);

MAGE-3 (3' primer) GGACGATTATCAGGAGGC-CTGC (SEQ ID NO:16);

Tyrosinase (5' primer) GGATAGCGGATGCCTCT-CAAAG (SEQ ID NO: 17);

Tyrosinase (3' primer) CCCAAGGAGCCATGACCA-GAT (SEQ ID NO:18);

Melan-A (5' primer) CTGACCCTACAAGATGCCAA-GAG (SEQ ID NO: 19); and

Melan-A (3' primer) ATCATGCATTGCAACATTTAT-TGA TGG AG (SEQ ID NO:20).

Nested primer templates are as follows:

MAGE-1 (5' primer) CTTCAGGTTTTCAGGGGACAG-GCC (SEQ ID NO:21);

MAGE-1 (3' primer) CTGTCGAGTGAAGTTGATGG-TAGTGG (SEQ ID NO:22);

MAGE-3 (5' primer) TCACATGCTCCCTCTCTC-CCAGGCC (SEQ ID NO:23);

MAGE-3 (3' primer) ATCTGATTGTCACCCAGCAG-GCCATC (SEQ ID NO:24);

Tyrosinase (5' primer) GCATGCACAATGCCTTGCA-CATCTATA (SEQ ID NO:25);

Tyrosinase (3' primer) TGTAGTCTTGAAAA-GAGTCTGGGTCTG (SEQ ID NO:26);

Melan-A (5' primer) TCTTACACCACGGCTGAAGAG-GCC (SEQ ID NO:27); and

Melan-A (3' primer) CCTCACATGATTAGT-GCTAGCGGA (SEQ ID NO:28).

All PCRT products are run on 1.5% agarose gels with ethidium bromide. Sizes of tumor antigen bands for primary PCR™ are shown below:

| Tumor antigen | Amplified cDNA | Contaminating DNA |
|---|---|---|
| B-actin | 615 bp | 615 bp and 830 bp (weak) |
| Mage-1 | 421 bp | none |
| Mage-3 | 725 bp | 805 bp |
| Tyrosinase | 383 bp | |
| Melan-A | 605 bp | |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Balch, Houghton, Peters, "Cutaneous Melanoma," In: *Cancer: Principals and Practice of Oncology,"* 4th ed, V. T. DeVita, S. Hellman and S. A. Rosenberg, eds. J. B. Lippincott, Philadelphia, 1612, 1993.

Berd, Maguire, McCue, Mastrangelo, "Treatment of metastatic melanoma with an autologous tumor-cell vaccine: clinical and immunologic results in 64 patients," *J. Clin. Oncol.,* 8:1858, 1990.

Boon, Cerottini, Van den Eynde, Van der Bruggen, Van Pel, "Tumor antigens recognized by T lymphocytes," *Ann. Rev. Immunol,* 12:337, 1994.

Boon, Gajewski, Coulie, "From defined human tumor antigens to effective immunization?," *Immunol. Today,* 16:334, 1995.

Brichard, Wariier, Van Pel, Morlighem, Lucas, Boon, "Individual differences in the orientation of the cytolytic T cell responses against mouse tumor P815," *Eur. J. Immunol,* 25:664, 1995.

Brunda, Luistro, Warrier, Wright, Hubbard, Murphy, Wolf, Gately, "Antitumor and antimetastatic activity of interleukin 12 against murine tumors," *J. Exp. Med.,* 178:1223, 1993.

Cerottini, Engers, MacDonald, Brunner, "Generation of cytotoxic T lymphocytes in vitro. I. Response of normal and immune mouse spleen cells in mixed leukocyte cultures, *J. Exp. Med.,* 140:703–717, 1974.

Chen, Linsley, Hellstrom. "Costimulation of T cells for tumor immunity," *Immunol Today,* 14:483, 1993.

Chen, McGowan, Ashe, Johnston, Li, Hellstrom, Hellstrom, "Tumor immunogenicity determines the effect of B7 costimulation on T cell-mediated tumor immunity," *J. Exp. Med.,* 179:523, 1994.

Cormier, Salgaller, Prevette, Barracchini, Rivoltini, Restifo, Rosenberg, Marincola, "Enhancement of cellular immunity in melanoma patients immunized with a peptide from MART-1/Melan-A," *Cancer J. Sci. Am.,* 3:37, 1997.

Coulie, Brichard, Van Pel, Wolfel, Schneider, Traversari, Matiei, De Plaen, Lurquin, Szikora, Renauld, Boon, "A new gene coding for a differentiation antigen recognized by autologous cytolytic T lymphocytes on HLA-A2 melanomas," *J. Exp. Med.,* 180:35, 1994.

Coulie, Lehmann, Lethe, Herman, Lurquin, Andrawiss, Boon, "A mutated intron sequence codes for an antigenic peptide recognized by cytolytic T lymphocytes on a human melanoma," *Proc. Natl. Acad. Sci. USA:* 92(17):7976–80, 1995.

Cronin, Stack, Fitch, "IL-4-producing $CD8^+$ T cell clones can provide B cell help," *J. Immunol,* 154:3118–3127, 1995.

De Plaen, Arden, Traversari, Gaforio, Szikora, De Smet, Brasseur, Van der Bruggen, Lethe, Lurquin, Brasseur, Chomez, De Backer, Cavenee, Boon, "Structure, chromosomal location, and expression of 12 genes of the MAGE family," *Immunogenetics,* 40:360–369, 1994.

De Plaen, Lurquin, Van Pel, Mariame, Szikora, Wolfel, Sibille, Chomez, Boon, "Immunogenic ($tum^-$) variants of mouse tumor P815: Cloning of the gene of $tum^-$ antigen P91A and identification of the tumn mutation," *Proc. Natl. Acad. Sci. USA,* 85:2274–2278, 1988.

Eilber, Morton, Holmes, Sparks, Ramming, "Adjuvant immunotherapy with BCG in treatment of regional-lymph-node metastases from malignant melanoma," *N. Engl. J. Med.,* 294:237, 1976.

Fallarino, Ashikari, Boon, Gajewski, "Antigen-specific regression of established tumors induced by active immunization with irradiated IL-12-but not B7-1-transfected tumor cells," *Inter. Immunol.,* 1997.

Fallarino, Uyttenhove, Boon, Gajewski, "Endogenous IL-12 is necessary for rejection of P815 tumor variants in vivo," *J. Immunol.,* 156:1095–1100, 1996.

Fitch, McKisic, Lancki, Gajewski, "Differential regulation of murine T IVmphocyte subsets," *Annul. Rev. Immunol.,* 11:29–48, 1993.

Gajewski, Renauld, Van Pel, Boon, "Costimulation with B7-1, IL-6, and IL-12 is sufficient for primary generation of murine anti-tumor cytolytic T lymphocytes in vitro," *J. Immunol.,* 154:5637, 1995.

Gajewski, "B7-1 but not B7-2 efficiently costimulates $CD8^+$ T lymphocytes in the P815 tumor system in vitro," *J. Immunol.,* 156: 465–472, 1996.

Gajewski, Uyttenhove, Fallarino, Boon. "Tumor rejection requires a CTLA4 ligand provided by the host or expressed on the tumor: Superiority of B7-1 over B7-2 for active tumor immunization," *J. Immunol.* 156:2909–2917, 1996.

Gimmi, Freeman, Gribben, Gray, Nadler, "Human T-cell clonal anergy is induced by antigen presentation in the absence of B7 costimulation," *Proc. Natl. Acad. Sci. USA,* 90:6586–6590, 1993.

Glasebrook and Fitch, "Alloreactive cloned T cell lines. I. Interactions between cloned amplifier and cytolytic T cell lines," *J. Exp. Med.,* 151:876–895, 1980.

Harding, McArthur, Gross, Raulet, Allison, "CD28-mediated signalling co-stimulates murine T cells and prevents induction of anergy in T-cell clones," *Nature,* 356:607–609, 1992.

Hawkins, "Immunotherapy with high-dose interleukin 2," In: *Comprehensive textbook of genitourinary oncology*, N.J. Vogelzang, P.T. Scardino, W. U. Shopley and D. S. Coffey, eds. Williams and Wilkins, Baltimore, 242, 1996.

Inaba, Young, Steinman, "Direct activation of CD8+ cytotoxic T lymphocytes by dendritic cells," *J. Exp. Med.*, 166:182–194, 1987.

Koh, "Cutaneous melanoma," *N. Engl. J Med*, 325:171–182, 1991.

Kubin, Kamoun, Trinchieri. "Interleukin 12 synergizes with BT/CD28 interaction in inducing efficient proliferation and cytokine production of human T cells," *J. Exp. Med.*, 180:211, 1994.

Lancki, Weiss, Fitch, "Requirements for triggering of lysis by cytolytic T lymphocyte clones," *J. Immunol.*, 138:3646–3653, 1987.

Legha and Buzaid, "Role of recombinant interleukin-2 in combination with interferon-alpha and chemotherapy in the treatment of advanced melanoma," *Semin. Oncol.*, 20:27, 1993.

Lethe, Van den Eynde, Van Pel, Corradin and Boon, "Mouse tumor rejection antigens P815A and P815B: two epitopes carried by a single peptide." *Eur. J. Immunol.* 22:2283–2288, 1992.

Linsley, Brady, Grosmaire, Aruffo, Damle, Ledbetter, "Binding of the B cell activation antigen B7 to CD28 costimulates T cell proliferation and Interleukin 2 mRNA accumulation," *J. Exp. Med.*, 173:721, 1991.

Manetti, Gerosa, Giudizi, Biagiotti, Parronchi, Piccinni, Sampognaro, Maggi, Romagnani, Trinchieri, "Interleukin 12 induces stable priming for interferon gamma (IFN-$\gamma$) production during differentiation of human T helper (Th) cells and transient IFN-$\gamma$ production in established Th2 clones," *J. Exp. Med*, 179:1273, 1994.

Marchand, Weynants, Rankin, Arienti, Belli, Parmiani, Cascinelli, Bourlond, Vanwijck, Humblet, Canon, Laurent, Naeyaert, Plagne, Deraemaeker, Knuth, Jager, Brasseur, Herman, Coulie, Boon, "Tumor regression responses in melanoma patients treated with a peptide encoded by gene MAGE-3," Int. *J. Cancer*, 63:883, 1995.

Mehrotra, Wu, Crim, Mostowski, Siegel, "Effects of IL-12 on the generation of cytotoxic activity in human CD8+ T lymphocytes," *J. Immunol.*, 151:2444, 1993.

Mukheiji, Chakraborty, Yamasaki, Okino, Yamase, Sporn, S. K. Kurtzman, Ergin, Ozols, Meehan, "Induction of antigen-specific cytolytic T cells in situ in human melanoma by immunization with synthetic peptide-pulsed autologous antigen presenting cells," *Proc. Natl Acad. Sci. USA*, 92:8078, 1995

Old, Boon, Cerottini, Finn, Knoth, Nathan, Pardoil, Srivastava, Takahashi, Unanue," "*Cancer Vaccines,* Abstract, S01, 1996.

Sad, Marcotte, Mosmann, "Cytokine-induced differentiation of precursor-mouse CD8+ T cells into cytotoxic CD8+ T cells secreting Th1 or Th2 cytokines," *Immunity*, 2:271–279, 1995.

Schwartz, "A cell culture model for T lymphocyte clonal anergy," *Science*, 248:1349, 1990.

Sibille, Chomez, Wildmann, Van Pel, De Plaen, Maryanski, de Bergeyck, Boon, "Structure of the gene of tum transplantation antigen P198: a point mutation generates a new antigenic peptide," *J. Exp. Med*, 172:35–45, 1990.

Stack, Lenschow, Gray, Bluestone, Fitch, "IL-4 treatment of small splenic B cells induces costimulatory molecules B7-1 and B7-2, *J. Immunol.*, 152:5723–5733, 1994.

Steinman, Kaplan, Witmer and Cohn, "Identification of a novel cell type in peripheral lymphoid organs of mice. V. Purification of splenic dendritic cells, new surface markers, and maintenance in vitro., *J. Exp. Med.* 149:1–16, 1979.

Tan, Anasetti, Hansen, Melrose, Brunvand, Bradshaw, Ledbetter, Linsley, "Induction of alloantigen-specific hyporesponsiveness in human T lymphocytes by blocking interaction of CD28 with its natural ligand BT/BB1," *J. Exp. Med.*, 177:165, 1993.

Townsend and Allison, "Tumor rejection after direct costimulation of CD8+ T cells by B7-transfected melanoma cells," *Science*, 259:368, 1993.

Uyttenhove, Godfraind, Lethe, Amar-Costesec, Renauld, Gajewski, Duffour, Warnier, Boon and Van den Eynde, "The expression of mouse gene P1A in testis does not prevent safe induction of cytolytic T cells against a P1A-encoded tumor antigen." *Int. J. Cancer.* 70:349–356, 1997.

Uyttenhove, Maryanski and Boon, "Escape of mouse mastocytomna P815 after nearly complete rejection is due to antigen-loss variants rather than immunosuppression, *aJ. Exp. Med.* 157:1040–1052, 1983.

Uyttenhove, Van Snick, Boon, "Immunogenic variants obtained by mutagenesis of mouse mastocytoma P815. I. Rejection by syngeneic mice," *J. Exp. Med.*, 152:1175–1183, 1980.

Van den Eynde, Lethe, Van Pel, De Plaen, Boon, "The gene coding for a major tumor rejection antigen of tumor P815 is identical to the normal gene of syngeneic DBA/2 mice," *J. Exp. Med*, 173:1373, 1991.

Van der Bruggen, Bastin, Gajewski, Coulie, Boel, De Smet, Traversari, Townsend, Boon, "A peptide encoded by human gene MAGE-3 and presented by HLA-A2 induces cytolytic T lymphocytes that recognize tumor cells expressing MAGE-3," *Eur. J. Immunol.*, 24:3038, 1994

Van der Bruggen, Traversari, Chomez, Lurquin, De Plaen, Van den Eynde, Knuth, Boon, "A gene encoding an antigen recognized by cytolytic T lymphocytes on a human melanoma," *Science*, 254:1643, 1991.

Van Pel, De Plaen, Boon, "Selection of a highly transfectable variant from mouse mastocytoma P815," *Somat/c. Cell Mol. Genet.*, 11:467, 1985.

Van Pel, Van der. Bruggen, Coulie, Brichard, Lethe, Van den Eynde, Uyttenhove, Renauld, Boon, "Genes coding for tumor antigens recognized by cytolytic T lymphocytes," *Immunol Rev.*, 145:229, 1995.

Wolfel, Van Pel, De Plaen, Lurquin, Maryanski, Boon, "Immunogenic (tum⁻) variants obtained by mutagenesis of mouse mastocytoma P815. VIII. Detection of stable transfectants expressing a tum antigen with a cytolytic T cell stimulation assay," *Immunogenetics*, 26:178–187, 1987.

What is claimed is:

1. A method of inducing a therapeutic immune response comprising:
   a) providing a composition comprising IL-12;
   b) providing a composition comprising antigen-presenting cells pulsed with peptide, wherein said antigen-presenting cells are not purified dendritic cells; and
   c) administering said composition comprising IL-12 and said composition comprising antigen-presenting cells pulsed with peptide to a mammal in an amount effective to induce an immune response.

2. The method of claim 1, wherein said antigen-presenting cells are autologous.

3. The method of claim 2, wherein said antigen-presenting cells are selected from the group consisting of B cells activated by lipopolysaccharide, non-fractionated spleen cells, fibroblasts and non-fractionated peripheral blood mononuclear cells.

4. The method of claim 1, wherein said peptide is expressed on the surface of said antigen-presenting cells in the context of class I MHC molecules or class II MHC molecules.

5. The method of claim 4, wherein said peptide is melanoma antigen.

6. The method of claim 4, wherein said peptide is virus antigen.

7. The method of claim 5, wherein said melanoma antigen is selected from the group consisting of MAGE-1, MGE-3, Melan-A, P198, P1A, gp100, and tyrosinase.

8. The method of claim 5, wherein said melanoma antigen is MAGE-1.

9. The method of claim 5, wherein said melanoma antigen is MAGE-3.

10. The method of claim 5, wherein said melanoma antigen is Melan-A.

11. The method of claim 5, wherein said melanoma antigen is P198.

12. The method of claim 5, wherein said melanoma antigen is P1A.

13. The method of claim 5, wherein said melanoma antigen is gp100.

14. The method of claim 5, wherein said melanoma antigen is tyrosinase.

15. The method of claim 5, wherein said melanoma antigen comprises a combination of antigens wherein at least one antigen is selected from the group consisting of MAGE-1, MAGE-3, Melan-A, P198, P1A, gp100, and tyrosinase.

16. The method of claim 1, wherein said antigen-presenting cells are pulsed with peptide at a concentration of from 0.1 $\mu$M–1 mM.

17. The method of claim 16, wherein said concentration is 10–50 $\mu$M.

18. The method of claim 1, wherein said immune response results in the production of said peptide specific cytolytic T lymphocytes.

19. The method of claim 1, wherein said administration comprises a single dose of antigen-presenting cells and one or more doses of IL-12.

20. The method of claim 19, wherein said dose of antigen-presenting cells is administered in an amount from $1 \times 10^6$–$1 \times 10^9$.

21. The method of claim 20, wherein said dose of antigen-presenting cells is about $1 \times 10^8$.

22. The method of claim 19, wherein said dose of IL-12 is administered in an amount from 1 ng/kg–1000 ng/kg.

23. The method of claim 22, wherein said dose of L-12 is 30–500 ng/kg.

24. The method of claim 1, wherein said mammal is a human.

25. The method of claim 1, wherein said mammal has a disease selected from the group consisting of cancer, viral infection, and parasitic infection.

26. The method of claim 25, wherein said disease is a melanoma.

27. The method of claim 25, wherein said disease is a viral infection.

28. A method of treating a mammal with a disease selected from the group consisting of cancer, viral infection, and parasitic infection comprising administering a composition comprising antigen-presenting cells pulsed with peptide and a composition comprising IL-12, wherein said antigen presenting cells are not purified dendritic cells and wherein a therapeutic immune response is induced in the mammal.

29. The method of claim 28, wherein said disease is a melanoma.

30. The method of claim 28, wherein said disease is a viral infection.

31. The method of claim 28, wherein said antigen-presenting cells are autologous.

32. The method of claim 31, wherein said antigen-presenting cells are selected from the group consisting of B cells activated by lipopolysaccharide, non-fractionated spleen cells, fibroblasts and non-fractionated peripheral blood mononuclear cells.

33. The method of claim 28, wherein said peptide is expressed on the surface of said antigen-presenting cells in the context of class I MHC molecules or class II MHC molecules.

34. The method of claim 33, wherein said peptide is a viral antigen.

35. The method of claim 33, wherein said peptide is a melanoma antigen.

36. The method of claim 35, wherein said melanoma antigen is selected from the group consisting of MAGE-1, MAGE-3, Melan-A, P198, P1A, gp100, and tyrosinase.

37. The method of claim 28, wherein said antigen-presenting cells are pulsed with peptide at a concentration of from 0.1 $\mu$M–1 mM.

38. The method of claim 37, wherein said concentration is 10–50 $\mu$M.

39. The method of claim 28, wherein said administration comprises a single dose of peptide-pulsed antigen-presenting cells combined with a single dose of IL-12 followed by multiple doses of IL-12.

40. The method of claim 41, wherein said dose of antigen-presenting cells is administered in an amount from $1 \times 10^6$–$1 \times 10^9$.

41. The method of claim 40, wherein said dose of antigen-presenting cells is about $1 \times 10^8$.

42. The method of claim 39, wherein said dose of IL-12 is administered in an amount from 1 ng/kg–1000 ng/kg.

43. The method of claim 42, wherein said dose of IL-12 is 30–500 ng/kg.

* * * * *

UNITED STATES PATENT AND TRADEMARK OFFICE
CERTIFICATE OF CORRECTION

PATENT NO.     : 6,716,422 B1
DATED          : April 6, 2004
INVENTOR(S)    : Gajewski et al.

It is certified that error appears in the above-identified patent and that said Letters Patent is hereby corrected as shown below:

<u>Title page,</u>
Item [75], after "(IT)", insert -- ; Matthew L. Sherman, Newton, MA (US) -- therefor.
Item [73], delete "Institute" and insert -- Institute, -- therefor.

<u>Column 66,</u>
Line 64, delete "MGE-3" and insert -- MAGE-3 -- therefor.

<u>Column 67,</u>
Line 35, delete "L-12" and insert -- IL-12 -- therefor.

Signed and Sealed this

Tenth Day of August, 2004

JON W. DUDAS
*Acting Director of the United States Patent and Trademark Office*

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS:
      (D) TOPOLOGY: linear (xi) SEQUENCE DESCRIPTION: SEQ ID NO:1:

Lys Tyr Gln Ala Val Thr Thr Thr Leu
1          5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS:
      (D) TOPOLOGY: linear (xi) SEQUENCE DESCRIPTION: SEQ ID NO:2:

Leu Pro Tyr Leu Gly Trp Leu Val Phe
1          5

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (xi) SEQUENCE DESCRIPTION: SEQ ID NO:3:

TGGAGGACCA GAGGCCCCC                                      19

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (xi) SEQUENCE DESCRIPTION: SEQ ID NO:4:

GGACGATTAT CAGGAGGCCT GC                               22

(2) INFORMATION FOR SEQ ID NO:5:

(i) SEQUENCE CHARACTERISTICS:
      (A) LENGTH: 23 base pairs
      (B) TYPE: nucleic acid
      (C) STRANDEDNESS: double
      (D) TOPOLOGY: linear (xi) SEQUENCE DESCRIPTION: SEQ ID NO:5:

CTGACCCTAC AAGATGCCAA GAG                             23

(2) INFORMATION FOR SEQ ID NO:6:

(i) SEQUENCE CHARACTERISTICS:
      (A) LENGTH: 27 base pairs (B) TYPE: nucleic acid
        (C) STRANDEDNESS: double
        (D) TOPOLOGY: linear (xi) SEQUENCE DESCRIPTION: SEQ ID NO:6:

ATCATGCATT GCAACATTTA TTGATGG                    27

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:7:

GGCATCGTGA TGGACTCCG                    19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:8:

GCTGGAAGGT GGACAGCGA                    19

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:9:

Phe Leu Trp Gly Pro Arg Ala Leu Val
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:10:

Ala Ala Gly Ile Gly Ile Leu Thr Val
1               5

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:11:

GGCATCGTGA TGGACTCCG                    19

(2) INFORMATION FOR SEQ ID NO:12:

(i) SEQUENCE CHARACTERISTICS:

```
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:12:

GCTGGAAGGT GGACAGCGA                                               19

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:13:

CGGCCGAAGG AACCTGACCC AG                                           22

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:14:

GCTCCGACCC TCACTGGGTT GCC                                          23

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:15:

TGGAGGACCA GAGGCCCCC                                               19

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:16:

GGACGATTAT CAGGAGGCCT GC                                           22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:17:

GGATAGCGGA TGCCTCTCAA AG                                           22

(2) INFORMATION FOR SEQ ID NO:18:

(i) SEQUENCE CHARACTERISTICS:
        (A) LENGTH: 21 base pairs
```

(B) TYPE: nucleic acid
        (C) STRANDEDNESS: double
        (D) TOPOLOGY: linear (xi) SEQUENCE DESCRIPTION: SEQ ID NO:18:

CCCAAGGAGC CATGACCAGA T                                             21

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:19:

CTGACCCTAC AAGATGCCAA GAG                                           23

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (xi) SEQUENCE DESCRIPTION: SEQ ID NO:20:

ATCATGCATT GCAACATTTA TTGATGGAG                                     29

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:21:

CTTCAGGTTT TCAGGGGACA GGCC                                          24

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO:22:

CTGTCGAGTG AAGTTGATGG TAGTGG                                        26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO:23:

TCACATGCTC CCTCTCTCCC CAGGCC                                        26

(2) INFORMATION FOR SEQ ID NO:24:

(i) SEQUENCE CHARACTERISTICS:
        (A) LENGTH: 26 base pairs
        (B) TYPE: nucleic acid -continued

```
        (C) STRANDEDNESS: double
        (D) TOPOLOGY: linear (xi) SEQUENCE DESCRIPTION: SEQ ID NO:24:

ATCTGATTGT CACCCAGCAG GCCATC                                            26

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO:25:

GCATGCACAA TGCCTTGCAC ATCTATA                                           27

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO:26:

TGTAGTCTTG AAAAGAGTCT GGGTCTG                                           27

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:27:

TCTTACACCA CGGCTGAAGA GGCC                                              24

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:28:

CCTCACATGA TTAGTGCTAG CGGA                                              24
```